(12) United States Patent
Colby

(10) Patent No.: US 11,173,012 B2
(45) Date of Patent: *Nov. 16, 2021

(54) THERAPEUTIC TOOTH BUD ABLATION

(71) Applicant: TriAgenics, Inc., Eugene, OR (US)

(72) Inventor: Leigh E. Colby, Eugene, OR (US)

(73) Assignee: TRIAGENICS, INC., Eugene, OR (US)

(*) Notice: Subject to any disclaimer, the term of this patent is extended or adjusted under 35 U.S.C. 154(b) by 0 days.

This patent is subject to a terminal disclaimer.

(21) Appl. No.: 17/006,697

(22) Filed: Aug. 28, 2020

(65) Prior Publication Data

US 2021/0007829 A1 Jan. 14, 2021

Related U.S. Application Data

(63) Continuation of application No. 16/418,944, filed on May 21, 2019, which is a continuation of application
(Continued)

(51) Int. Cl.
*A61C 1/08* (2006.01)
*A61B 18/14* (2006.01)
(Continued)

(52) U.S. Cl.
CPC .......... *A61C 1/082* (2013.01); *A61B 18/1477* (2013.01); *A61B 34/10* (2016.02);
(Continued)

(58) Field of Classification Search
CPC ............ A61B 18/1477; A61B 14/1402; A61B 2018/1405–1497; A61B 8/4254; A61B 8/4245; A61B 34/20; A61B 34/10; A61B 2034/2046; A61B 2034/2048; A61B 2034/2051; A61B 2034/2053; A61B 2034/2055; A61B 2034/2057; A61B 2034/2059; A61B 2034/2063; A61B 2034/2065; A61B 2034/2068;
(Continued)

(56) References Cited

U.S. PATENT DOCUMENTS 610,355 A 9/1898 Kinne et al.
752,378 A 2/1904 Dailey
(Continued)

FOREIGN PATENT DOCUMENTS

AU 2010247874 11/2010
AU 2015213338 9/2015
(Continued)

OTHER PUBLICATIONS

Aaoms, "Evidence Based Third Molar Surgery," American Association of Oral and Maxillofacial Surgeons, USA, Nov. 10, 2011, 5 pages.
(Continued)

*Primary Examiner* — Yogesh P Patel
(74) *Attorney, Agent, or Firm* — Law Office of Karen Dana Oster, LLC

(57) ABSTRACT

Ablation probe tips (108, 148, 320, 360) and physical and virtual stents (110) for use in tooth bud ablation procedures that result in tooth agenesis as well as tooth bud ablation methods are described herein.

11 Claims, 33 Drawing Sheets

Related U.S. Application Data

No. 16/036,904, filed on Jul. 16, 2018, now Pat. No. 10,765,490, which is a continuation of application No. 14/849,431, filed on Sep. 9, 2015, now Pat. No. 10,022,202, which is a continuation of application No. PCT/US2013/032357, filed on Mar. 15, 2013, said application No. 16/418,944 is a continuation of application No. 15/829,874, filed on Dec. 2, 2017, now Pat. No. 10,298,255, which is a continuation of application No. 14/849,464, filed on Sep. 9, 2015, now Pat. No. 9,855,112, which is a continuation of application No. PCT/US2013/032357, filed on Mar. 15, 2013, application No. 16/418,944, which is a continuation of application No. 15/215,020, filed on Jul. 20, 2016, now Pat. No. 10,335,248.

(51) Int. Cl.
*A61C 3/14* (2006.01)
*A61B 34/10* (2016.01)
*A61B 34/20* (2016.01)
*A61B 18/00* (2006.01)
*A61B 17/00* (2006.01)
*A61C 9/00* (2006.01)

(52) U.S. Cl.
CPC .............. *A61B 34/20* (2016.02); *A61C 3/14* (2013.01); *A61B 2017/00115* (2013.01); *A61B 2018/00321* (2013.01); *A61B 2018/00565* (2013.01); *A61B 2018/00577* (2013.01); *A61C 9/004* (2013.01); *A61C 9/0006* (2013.01)

(58) Field of Classification Search
CPC .... A61B 2034/107; A61B 2018/00577; A61C 1/082; G09B 23/28; G09B 23/285
See application file for complete search history.

(56) References Cited

U.S. PATENT DOCUMENTS

| | | | |
|---|---|---|---|
| 1,713,971 A | 5/1929 | Lowry et al. | |
| 2,317,648 A | 4/1943 | Siqveland | |
| 4,672,963 A | 6/1987 | Barken | |
| 4,895,517 A | 1/1990 | Fischer | |
| 4,925,523 A | 5/1990 | Braren et al. | |
| 5,009,595 A | 4/1991 | Osborn | |
| 5,015,183 A | 5/1991 | Fenick | |
| 5,133,660 A | 7/1992 | Fenick | |
| 5,500,012 A | 3/1996 | Brucker et al. | |
| 5,556,278 A | 9/1996 | Meitner | |
| 5,613,852 A | 3/1997 | Bavitz | |
| 5,623,931 A | 4/1997 | Wung et al. | |
| 5,642,997 A | 7/1997 | Gregg, II et al. | |
| 5,688,118 A | 11/1997 | Hayka et al. | |
| 5,725,376 A | 3/1998 | Poirier | |
| 5,768,134 A | 6/1998 | Swaelens et al. | |
| 5,792,140 A | 8/1998 | Tu et al. | |
| 5,800,168 A | 9/1998 | Cascione et al. | |
| 5,816,814 A | 10/1998 | Venta et al. | |
| 5,843,021 A | 12/1998 | Edwards et al. | |
| 5,851,112 A | 12/1998 | Daikuzono et al. | |
| 5,906,609 A | 5/1999 | Assa et al. | |
| 5,916,213 A | 6/1999 | Haissaguerre et al. | |
| 5,941,845 A | 8/1999 | Tu et al. | |
| 5,941,889 A | 8/1999 | Cermak | |
| 5,943,719 A | 8/1999 | Feldman et al. | |
| 5,967,777 A | 10/1999 | Klein et al. | |
| 6,027,497 A | 2/2000 | Daniel et al. | |
| 6,162,052 A | 12/2000 | Kokubu | |
| 6,179,803 B1 | 1/2001 | Edwards et al. | |
| 6,179,830 B1 | 1/2001 | Kokubu | |
| 6,203,499 B1 | 3/2001 | Imling et al. | |
| 6,210,355 B1 | 4/2001 | Edwards et al. | |
| 6,241,725 B1 | 6/2001 | Cosman | |
| 6,245,062 B1 | 6/2001 | Berube et al. | |
| 6,270,476 B1 | 8/2001 | Santoianni et al. | |
| 6,319,006 B1 | 11/2001 | Scherer et al. | |
| 6,386,869 B1 | 5/2002 | Zegarelli | |
| 6,607,524 B1 | 8/2003 | LaBudde et al. | |
| 6,621,491 B1 | 9/2003 | Baumrind et al. | |
| 6,622,731 B2 | 9/2003 | Daniel et al. | |
| 6,913,463 B2 | 7/2005 | Blacklock | |
| 6,936,046 B2 | 8/2005 | Hissong et al. | |
| 6,971,877 B2 | 12/2005 | Harter | |
| 7,014,461 B2 | 3/2006 | Weinstein | |
| 7,044,735 B2 | 5/2006 | Malin | |
| 7,097,451 B2 | 8/2006 | Tang | |
| 7,169,155 B2 | 1/2007 | Chu et al. | |
| 7,226,288 B2 | 6/2007 | Schoeffel | |
| 7,249,952 B2 | 7/2007 | Ranta et al. | |
| 7,346,417 B2 | 3/2008 | Luth et al. | |
| 7,457,443 B2 | 11/2008 | Persky | |
| 7,467,015 B2 | 12/2008 | Weide | |
| 7,492,987 B2 | 2/2009 | Yeik et al. | |
| 7,553,309 B2 | 6/2009 | Buysse et al. | |
| 7,615,047 B2 | 11/2009 | Berna et al. | |
| 7,776,035 B2 | 8/2010 | Rick et al. | |
| 7,787,132 B2 | 8/2010 | Körner et al. | |
| 7,812,815 B2 | 10/2010 | Banerjee et al. | |
| 7,819,591 B2 | 10/2010 | Rohaly et al. | |
| 7,959,441 B2 | 6/2011 | Glover et al. | |
| 7,976,469 B2 | 7/2011 | Bonde et al. | |
| 7,990,548 B2 | 8/2011 | Babayoff et al. | |
| 8,013,853 B1 | 9/2011 | Douglas et al. | |
| 8,048,067 B2 | 11/2011 | Davalos et al. | |
| 8,057,487 B2 | 11/2011 | Chu et al. | |
| 8,211,099 B2 | 7/2012 | Buysse et al. | |
| 8,221,121 B2 | 7/2012 | Berckmans et al. | |
| 8,257,341 B2 | 9/2012 | Fletcher | |
| 8,310,683 B2 | 11/2012 | Babayoff et al. | |
| 8,363,228 B2 | 1/2013 | Babayoff | |
| 8,372,061 B2 | 2/2013 | Berna et al. | |
| 8,377,057 B2 | 2/2013 | Rick et al. | |
| 8,480,666 B2 | 7/2013 | Buysse et al. | |
| 8,626,317 B2 | 1/2014 | Higgins | |
| 8,670,816 B2 | 3/2014 | Green et al. | |
| 8,834,409 B2 | 9/2014 | Manley | |
| 8,892,235 B2 | 11/2014 | Choi et al. | |
| 8,945,144 B2 | 2/2015 | Cunningham | |
| 8,979,871 B2 | 3/2015 | Tyc et al. | |
| 9,028,252 B1 | 5/2015 | Shabat | |
| 9,066,712 B2 | 6/2015 | Fourkas et al. | |
| 9,113,912 B1 | 8/2015 | Mehta et al. | |
| 9,119,628 B1 | 9/2015 | Mehta et al. | |
| 9,168,091 B2 | 10/2015 | Janssen et al. | |
| 9,271,796 B2 | 3/2016 | Buysse et al. | |
| 9,402,691 B2 | 8/2016 | Merritt et al. | |
| 9,402,693 B2 | 8/2016 | Colby | |
| 9,415,194 B2 | 8/2016 | Wolf et al. | |
| 9,622,813 B2 | 4/2017 | Krugman et al. | |
| 9,724,236 B2 | 8/2017 | Abe | |
| 9,827,068 B2 | 11/2017 | Colby | |
| 9,844,324 B2 | 12/2017 | Merritt et al. | |
| 9,855,112 B2 * | 1/2018 | Colby ................. A61C 3/14 |
| 9,943,374 B2 | 4/2018 | Merritt et al. | |
| 10,022,202 B2 * | 7/2018 | Colby ................. A61C 1/082 |
| 10,265,140 B2 | 4/2019 | Colby | |
| 10,285,778 B2 | 5/2019 | Colby | |
| 10,298,255 B2 * | 5/2019 | Colby ................. A61C 3/14 |
| 10,299,885 B2 | 5/2019 | Colby | |
| 10,350,008 B2 | 7/2019 | Gibbs et al. | |
| 2002/0058872 A1 | 5/2002 | Steininger et al. | |
| 2002/0128642 A1 | 9/2002 | Berube et al. | |
| 2002/0160337 A1 | 10/2002 | Klein et al. | |
| 2003/0130575 A1 | 7/2003 | Desai | |
| 2004/0097805 A1 * | 5/2004 | Verard ............... A61B 1/00071 600/428 |
| 2004/0102767 A1 | 5/2004 | Stingl et al. | |
| 2004/0157188 A1 | 8/2004 | Luth et al. | |
| 2004/0158194 A1 | 8/2004 | Wolff et al. | |
| 2004/0215186 A1 | 10/2004 | Cornelius et al. | |
| 2004/0219482 A1 | 11/2004 | Bina et al. | |

(56) References Cited

U.S. PATENT DOCUMENTS

| | | |
|---|---|---|
| 2004/0249370 A1 | 12/2004 | Berna et al. |
| 2005/0090820 A1 | 4/2005 | Cornelius et al. |
| 2005/0170312 A1 | 8/2005 | Pond |
| 2005/0177074 A1 | 8/2005 | Becker et al. |
| 2005/0186533 A1 | 8/2005 | Cohen |
| 2005/0245817 A1* | 11/2005 | Clayton ............ A61B 5/06 600/424 |
| 2005/0283148 A1 | 12/2005 | Janssen et al. |
| 2006/0009404 A1 | 1/2006 | Williams |
| 2006/0074413 A1 | 4/2006 | Behzadian |
| 2006/0084958 A1 | 4/2006 | Raif et al. |
| 2006/0111705 A1 | 5/2006 | Janzen et al. |
| 2006/0115782 A1 | 6/2006 | Li et al. |
| 2006/0127859 A1 | 6/2006 | Wen |
| 2006/0195169 A1 | 8/2006 | Gross et al. |
| 2006/0240378 A1 | 10/2006 | Weinstein et al. |
| 2007/0016183 A1 | 1/2007 | Lee et al. |
| 2007/0135707 A1 | 6/2007 | Redel et al. |
| 2007/0179485 A1 | 8/2007 | Yeik et al. |
| 2007/0224570 A1 | 9/2007 | West et al. |
| 2007/0265628 A1 | 11/2007 | Kraus et al. |
| 2007/0293756 A1 | 12/2007 | Jung et al. |
| 2007/0294280 A1 | 12/2007 | Jung et al. |
| 2008/0009747 A1 | 1/2008 | Saadat et al. |
| 2008/0039709 A1 | 2/2008 | Karmarkar |
| 2008/0138761 A1 | 6/2008 | Pond |
| 2008/0176187 A1 | 7/2008 | Stumpel |
| 2008/0182218 A1 | 7/2008 | Chen et al. |
| 2008/0199829 A1 | 8/2008 | Paley et al. |
| 2009/0011382 A1 | 1/2009 | Bavar |
| 2009/0062790 A1 | 3/2009 | Malchano et al. |
| 2009/0076498 A1 | 3/2009 | Saadat et al. |
| 2009/0088830 A1 | 4/2009 | Mohamed et al. |
| 2009/0136902 A1 | 5/2009 | Zundorf et al. |
| 2009/0253095 A1 | 10/2009 | Salcedo et al. |
| 2009/0258330 A1 | 10/2009 | Huber et al. |
| 2009/0263764 A1 | 10/2009 | Berckmans et al. |
| 2009/0306652 A1 | 12/2009 | Buysse et al. |
| 2010/0021866 A1 | 1/2010 | Tsuji et al. |
| 2010/0030061 A1* | 2/2010 | Canfield ............ A61B 6/032 600/413 |
| 2010/0035201 A1 | 2/2010 | Beck et al. |
| 2010/0082032 A1 | 4/2010 | Berna et al. |
| 2010/0100094 A1 | 4/2010 | Truckai |
| 2010/0114184 A1 | 5/2010 | Degtyar et al. |
| 2010/0129771 A1 | 5/2010 | Tsuji et al. |
| 2010/0203479 A1 | 8/2010 | Bulloch et al. |
| 2010/0298705 A1* | 11/2010 | Pelissier ............ A61B 8/42 600/443 |
| 2010/0311006 A1 | 12/2010 | Lancieux et al. |
| 2010/0311028 A1 | 12/2010 | Bell, III et al. |
| 2010/0316974 A1 | 12/2010 | Yau et al. |
| 2011/0098697 A1* | 4/2011 | Brannan ............ H04W 64/003 606/33 |
| 2011/0104632 A1 | 5/2011 | Colby |
| 2011/0130689 A1 | 6/2011 | Cohen et al. |
| 2011/0137156 A1 | 6/2011 | Razzaque et al. |
| 2011/0200960 A1 | 8/2011 | Colby |
| 2011/0200961 A1 | 8/2011 | Colby |
| 2011/0244417 A1 | 10/2011 | Hilsen et al. |
| 2012/0046536 A1 | 2/2012 | Cheung et al. |
| 2012/0100500 A1 | 4/2012 | Gao |
| 2013/0017507 A1 | 1/2013 | Son et al. |
| 2013/0150843 A1 | 6/2013 | Berna et al. |
| 2013/0172731 A1 | 7/2013 | Gole |
| 2013/0197355 A1 | 8/2013 | Lee et al. |
| 2014/0066917 A1 | 3/2014 | Cosman, Jr. et al. |
| 2014/0081260 A1 | 3/2014 | Cosman, Jr. et al. |
| 2014/0093838 A1 | 4/2014 | Carmichael et al. |
| 2014/0121658 A1 | 5/2014 | Cosman, Jr. et al. |
| 2014/0186796 A1 | 7/2014 | Suttin |
| 2014/0193771 A1 | 7/2014 | Dolfi et al. |
| 2014/0257272 A1 | 9/2014 | Clark, III et al. |
| 2014/0276033 A1 | 9/2014 | Brannan et al. |
| 2014/0378964 A1 | 12/2014 | Pearson |
| 2015/0018801 A1 | 1/2015 | Lazarof |
| 2015/0018822 A1 | 1/2015 | Racz |
| 2015/0147714 A1 | 5/2015 | Daon |
| 2015/0150631 A1 | 7/2015 | Lee |
| 2015/0265371 A1 | 9/2015 | Kim |
| 2015/0351831 A1 | 12/2015 | Janssen et al. |
| 2015/0374456 A1 | 12/2015 | Colby |
| 2015/0374457 A1 | 12/2015 | Colby |
| 2016/0106518 A1 | 4/2016 | Choi et al. |
| 2016/0151113 A1 | 6/2016 | Kim et al. |
| 2016/0157967 A1 | 6/2016 | Kim et al. |
| 2016/0324597 A1 | 11/2016 | Colby |
| 2017/0039489 A1 | 2/2017 | Reh et al. |
| 2017/0231718 A1 | 8/2017 | Wohrle et al. |
| 2017/0290554 A1 | 10/2017 | Merritt |
| 2017/0360528 A1 | 12/2017 | Colby |
| 2018/0014910 A1 | 1/2018 | Colby |
| 2018/0091169 A1 | 3/2018 | Colby |
| 2018/0153640 A1 | 6/2018 | Colby |
| 2018/0261922 A1 | 9/2018 | Behdad et al. |
| 2018/0318038 A1 | 11/2018 | Colby |
| 2019/0029751 A1 | 1/2019 | Hancock et al. |

FOREIGN PATENT DOCUMENTS

| | | |
|---|---|---|
| EP | 2301469 A1 | 3/2011 |
| EP | 2429444 | 3/2012 |
| FR | 2925289 | 1/2011 |
| GB | 2057888 | 4/1981 |
| MX | 357449 | 7/2018 |
| WO | 2004084748 A1 | 10/2004 |
| WO | WO 2006031317 | 6/2006 |
| WO | WO 2007057902 | 5/2007 |
| WO | WO 2007085719 | 8/2007 |
| WO | WO 2008067334 | 6/2008 |
| WO | WO 2008128720 | 10/2008 |
| WO | WO 2010132368 | 11/2010 |
| WO | 2011017168 A2 | 2/2011 |
| WO | 2017103209 A1 | 6/2017 |

OTHER PUBLICATIONS

Aaoms, "White Paper on Third Molar Data," Article published at www.aaoms.org, Mar. 2007, 25 pages.

Ahmad, et al., "Caries Experience and Periodontal Pathology in Erupting Third Molars," Abstract, Journal of Oral and Maxillofacial Surgery, 66(5):948-53 (ISSN: 1531-5053), Chapel Hill, NC 27599, USA, 2008.

Al-Khateeb, et al., "Pathology Associated with Impacted Mandibular Third Molars in a Group of Jordanians," Abstract, Journal of Oral and Maxillofacial Surgery, 64(11): 1598-602, Irbid, Jordan, 2006.

American Dental Association, "Growth in Dental Spending Expected to Slow in 2009," published at www.ada.org, Feb. 26, 2009, 1 page.

American Public Health Association, "Opposition to Prophylactic Removal of Third Molars (Wisdom Teeth)," Policy Statement Database, Policy No. 20085, Washington, DC 20001, USA, Oct. 28, 2008, 5 pages.

Askboots, "Removing Wisdom Teeth," BMJ Publishing Group Limited, published at www.askboots.com, Web Article, Sep. 21, 2007, 9 pages.

Australian Government, IP Australia, "Patent Examination Report No. 1 (2010247874)," Jan. 2, 2014, 3 pages.

Bataineh, A. B., "Sensory Nerve Impairment Following Mandibular Third Molar Surgery," Abstract, Journal of Oral and Maxillofacial Surgery, 59(9): 1012-7 (ISSN: 0278-2391), Irbid, Jordan, 2001.

Blakey, et al., "Impact of Removal of Asymptomatic Third Molars on Periodontal Pathology," Abstract, Journal of Oral and Maxillofacial Surgery, 67(2): 245-50, Chapel Hill, NC 27599, USA, Feb. 2009.

Blakey, et al., "Periodontal Pathology Associated with Asymptomatic Third Molars," Abstract, Journal of Oral and Maxillofacial Surgery, 60(11): 1227-33 (ISSN: 0278-2391), Chapel Hill, NC 27599, USA, 2002.

(56) References Cited

OTHER PUBLICATIONS

Blankenship, et al., "Third Molar Development in the Estimation of Chronologic Age in American Blacks as Compared with Whites," Journal of Forensic Science, 52(2): 428-33, Memphis, TN 38163, USA, 2007.

Blankenship, et al., "Third Molar Development in the Estimation of Chronologic Age in American Blacks as Compared with Whites," Abstract, Journal of Forensic Science, 52(2): 428-33, Memphis, TN 38163, USA, 2007.

Blondeau, et al., "Extraction of Impacted Mandibular Third Molars Postoperative Complications and Their Risk Factors," Abstract, Journal of the Canadian Dental Association, vol. 73, No. 4, (ISSN: 1488-2159), May 2007, 2 pages.

Brace, et al., "Pulmonary Thermal Ablation: Comparison of Radiofrequency and Microwave Devices by Using Gross Pathologic and CT Findings in a Swine Model," Abstract, Radiology, vol. 251, 705-11, Madison, WI 53792, USA, Jun. 2009.

Brace, C. L., "Microwave Ablation Technology Avoids Problems that Plague RFA, Offers Promise for New Applications," Diagnostic Imaging, Madison, WI 53792, USA, Mar. 13, 2006, 2 pages.

Bui, et al., "Types, Frequencies, and Risk Factors for Complications After Third Molar Extraction," Journal of Oral and Maxillofacial Surgery, 61:1379-1389, Chapel Hill, NC 27599, USA, 2003, 11 pages.

Christiaens, et al., "Complications After Third Molar Extractions Retrospective Analysis of 1,213 Teeth," Abstract, Rev Stomatol Chir Maxillofac, 103(5):269-74 (ISSN: 0035-1768), Belgique, France, 2002.

Dodson, et al., "Introduction," American Association of Oral and Maxillofacial Surgeons, http://dx.doi.org/10.1016/j.joms.2012.04.022, Journal of Oral and Maxillofacial Surgery, vol. 70, No. 9, Supplement 1, USA, Sep. 2012, pp. S2-S3.

Dodson, et al., "Summary of the Proceedings of the Third Molar Multidisciplinary Conference," © 2012 American Association of Oral and Maxillofacial Surgeons, Journal of Oral and Maxillofacial Surgery, http://dx.doi.org/10.1016/j-joms.2012.05.001, vol. 70, No. 9, Supplement 1, USA, Sep. 2012, pp. S66-S69.

Dodson, T. B., "Response to APHA C3: Opposition to Prophylactic Removal of Third Molars," Article, Massachusetts General Hospital, Boston, MA 02114, USA, Oct. 26, 2008, 3 pages.

Eklund, et al., "Third-Molar Removal Patterns in an Insured Population," Journal of the American Dental Association, vol. 132, No. 4, 469-475, 2001, 16 pages.

Elter, et al., "Third Molars Associated with Periodontal Pathology in Older Americans," Abstract, Journal of Oral and Maxillofacial Surgery, 63(2): 179-84, Chapel Hill, NC 27599, USA, Feb. 2005.

Elter, et al., "Third Molars Associated with Periodontal Pathology in the Third National Health and Nutrition Examination Survey," Abstract, Journal of Oral and Maxillofacial Surgery, 62(4):440-5, Chapel Hill, NC 27599, USA, 2004.

European Patent Office, European Search Report including the European Search Opinion and Supplementary European Search Report for Application No. EP 10775341.0, dated Jul. 11, 2014, 8 pages.

Fox, M., "Shots kill budding wisdom teeth, study suggests," ©NBCNews.com, http://vitals.nbcnews.com/_news/2013/04/03/17584797-shots-kill-budding-wisdom-teeth-studysuggests%0D%0A%0D%0ANBCNews.com, New York, NY, USA, Apr. 3, 2013, 13 pages.

Friedman, J. W., "Containing the Cost of Third-Molar Extractions: A Dilemma for Health Insurance," Public Health Reports, vol. 98, No. 4, Los Angeles, CA 90057, USA, Jul.-Aug. 1983, pp. 376-384.

Friedman, J. W., "Opposition to Prophylactic Removal of Third Molars," APHA Oral Health Section, Feb. 18, 2008, pp. 1-10.

Friedman, J. W., "The Prophylactic Extraction of Third Molars: A Public Health Hazard," American Journal of Public Health, vol. 97, No. 9, Los Angeles, Ca, USA, Sep. 2007, pp. 1554-1559.

Gordon, et al., "The effects of local hypothermia on odontogenesis," Journal of Oral Surgery, 37(4):235-44, PubMed—indexed for Medline, USA, Apr. 1979.

Gordon, et al., "The effects of local hypothermia on odontogenesis," Abstract, Journal of Oral Surgery, 37(4):235-44, PubMed—indexed for Medline, USA, Apr. 1979.

Guralnick, et al., "Removal of Third Molars," National Institutes of Health Consensus Development Conference Statement, NIH Consens Statement Online Nov. 28-30, 1979, 2(11):65-68, USA, Nov. 28-30, 1979.

Harrison, L., "Nerve Blocks in Children May Destroy Future Molars," © 2013 WebMD, LLC, Medscape Medical News, www.medscape.com, USA, Apr. 8, 2013, 2 pages.

Hicks, E. P., "Third Molar Management: A Case Against Routine Removal in Adolescent and Young Adult Orthodontic Patients," Abstract, Journal of Oral and Maxillofacial Surgery, 57(7):831-6, Lexington, KY, USA, 1999.

Huang, et al., "Third-Molar Extraction as a Risk Factor for Temporomandibular Disorder," Journal of the American Dental Association, vol. 137, No. 11, American Dental Association, 2006, pp. 1547-1554.

Itero, "OrthoCAD, A Digitally Perfect Orthodontic Impression," www.cadentic.com, © Cadent, Ltd, 2009, 7 pages.

Jiang, P., "Ten-Year Insurance Claims Data Study Reveals Increase in Utilization of Surgical Extraction Codes," Online Periodical, Delta Dental of Minnesota, Eagan, MN 55122, USA, Winter 2006/2007, 2 pages.

Kajii, et al., "Presence of Third Molar Germs in Orthodontic Patients in Japan," Abstract, American Journal of Orthodontics & Dentofacial Orthopedics, vol. 119, Issue 3, Mar. 2001, pp. 245-250.

Kaminishi, et al., "A 10-year Comparative Study of the Incidence of Third Molar Removal in the Aging Population," Abstract, Journal of Oral Maxillofacial Surgery, 64(2): 173-4 (ISSN: 0278-2391), Los Angeles, CA, USA, 2006.

Kaminishi, et al., "New Considerations in the Treatment of Compromised Third Molars," Abstract, Journal of the California Dental Association, 32(10):823-5 (ISSN: 1043-2256), Los Angeles, CA, USA, 2004.

Kan, et al., "Residual Periodontal Defects Distal to the Mandibular Second Molar 6-36 Months after Impacted Third Molar Extraction," Abstract, J. Clinical Periodontal, 29(11):1004-11, Hong Kong SAR, China, Nov. 2002.

Kiukkonen, "Toxicity of dioxin to developing teeth and salivary glands," Helsinki University Biomedical Dissertations No. 77, Jun. 16, 2006, 94 pages.

Knutsson, et al., "Dentists' Decision on Prophylactic Removal of Mandibular Third Molars: A 10-year Follow-Up Study," Abstract, Community Dental and Oral Epidemiology, 29(4):308-14, Malmo University, Sweden, 2001.

Kunkel, et al., "Guideline: Surgical Removal of Third Molars," ZZQ Agency for Quality in Dentistry, Cologne, Germany 50931, Apr. 2006, pp. 1-16.

Kunkel, et al., "Severe Third Molar Complications Including Death-Lessons from 100 Cases Requiring Hospitalization," Abstract, Journal of Oral Maxillofacial Surgery, 65(9):1700-6, Mainz, Germany, 2007.

Kunkel, et al., "Third Molar Complications Requiring Hospitalization," Abstract, Oral Surgery, Oral Medicine, Oral Pathology, Oral Radiology, and Endodontology, 102(3):300-6 (ISSN: 1528-395X), Mainz, Germany, 2006.

Kusek, K., "Researchers use light to coax stem cells to repair teeth," © 2013 President and Fellows of Harvard College, Harvard School of Engineering and Applied Sciences, Wyss Institute, http://www.seas.harvard.edu/news/2014/05/researchers-use-light-to-coax-stem-cells-to-repairteeth, Cambridge/Boston, MA, USA, May 28, 2014, pp. 1-6.

Langsten, et al., "The Impact of Retained Third Molars on the Deployed Airman," Abstract, Military Medicine, vol. 173, Supplement 1, pp. 27-28(2), AMSUS, Eglin Air Force Base, FL 32542, USA, Jan. 2008.

Levin, D., "Nipping Wisdom Teeth in the Bud: Childhood Anesthesia May Thwart the Development of Third Molars," © 2014 Tufts University, Tufts Dental Medicine, http://now.tufts.edu/articles/nipping-wisdom-teeth-bud, Boston, MA, USA, Fall 2013, 1 page.

McArdle, et al., "Distal Cervical Caries in the Mandibular Second Molar An Indication for the Prophylactic Removal of the Third

(56) References Cited

OTHER PUBLICATIONS

Molar?," Abstract, British Journal of Oral Maxillofacial Surgery, 44(1):42-5, London, UK, Feb. 2006.
Moss, et al., "Third Molar Periodontal Pathology and Caries in Senior Adults," Abstract, Journal of Oral Maxillofacial Surgery, 65(1):103-8 (ISSN 0278-2391), Chapel Hill, NC 27599, USA, 2007.
Nance, et al., "Change in Third Molar Angulation and Position in Young Adults and Follow-Up Periodontal Pathology," Abstract, Journal Oral Maxillofacial Surgery, 64(3):424-8, Chapel Hill, NC 27599, USA, Mar. 2006.
National Institutes of Health, "Removal of Third Molars," NIH Consensus Statement Online, 2(11):65-8, Nov. 28-30, 1979.
Park, et al., "Cortical Integrity of the Inferior Alveolar Canal as a Predictor of Paresthesia After Third-Molar Extraction," Journal of American Dental Association, vol. 141, No. 3, 271-8, 2010.
Patent Cooperation Treaty, International Preliminary Report on Patentability, PCT/US10/34259, dated Aug. 31, 2011, 31 pages.
Patent Cooperation Treaty, International Searching Authority, International Search Report and Written Opinion of PCT/US13/32357, dated Jun. 5, 2013, 24 pages.
Patent Cooperation Treaty, Notification of Transmittal of International Preliminary Report on Patentability, and "International Preliminary Report on Patentability," for PCT/US13/32357, at least as early as May 8, 2015, 14 pages.
Patent Cooperation Treaty, Written Opinion International Search Report, PCT/US10/34259, dated Sep. 14, 2010, 25 pages.
Pogrel, et al., "White Paper on Third Molar Data," American Association of Oral and Maxillofacial Surgeons, http://www.aaoms.org/docs/third_molar_white_paper.pdf, USA, Mar. 2007, pp. 1-25.
Pogrel, M. A., "What Is the Effect of Timing of Removal on the Incidence and Severity of Complications?," © 2012 American Association of Oral and Maxillofacial Surgeons, Journal of Oral and Maxillofacial Surgery, http://dx.doi.org/10.1016/j-joms.2012.04.028, vol. 70, No. 9, Supplement 1, USA, Sep. 2012, pp. S37-S40.
Pratt, et al., "Indications for Third Molar Surgery," J. R. Coll. Surg. Edinb, vol. 43, Portsmouth, UK, Apr. 1998, pp. 105-108.
Rakprasitkul, S., "Pathologic Changes in the Pericoronal Tissues of Unerupted Third Molars," Abstract, Quintessence International, 32(8):633-8 (ISSN: 0033-6572), Rajthevee, Bangkok, Thailand 10400, 2001.
Ricketts, et al., "Third Molar Enucleation: Diagnosis and Technique," Journal—California Dental Association, http://www.ncbi.nlm.nih.gov/pubmed/1074850, USA, Apr. 1976, pp. 52-57.
Sarnat, et al., "Developmental Stages of the Third Molar in Israeli Children," Abstract, Pediatric Dentistry, 25(4):373-7 (ISSN: 0164-1263) Tel Aviv, Israel, 2003.
Shugars, et al., "Incidence of Occlusal Dental Caries in Asymptomatic Third Molars," Abstract, Journal Oral Maxillofacial Surgery, 63(3):341-6 (ISSN: 0278-2391), Chapel Hill, NC 27599, USA, 2005.
Silvestri, et al., "Prevention of Third Molar Development in Dog with Long Pulse Diode Laser: A Preliminary Report," Lasers Surg. Med, 39(8):674-7 (ISSN: 0196-8092), Boston, MA 02111, USA, 2007.
Silvestri, et al., "Prevention of Third Molar Development in Dog with Long Pulse Diode Laser: A Preliminary Report," Abstract, Lasers Surg. Med, 39(8):674-7 (ISSN: 0196-8092), Boston, MA, USA, 2007.
Silvestri, et al., "Prevention of Third Molar Tooth Development in Neonate Rat with a Long Pulse Diode Laser," Lasers Surg. Med, 35(5):385-91 (ISSN: 0196-8092), Boston, MA 02111, USA, 2004.
Silvestri, et al., "Prevention of Third Molar Tooth Development in Neonate Rat with a Long Pulse Diode Laser," Abstract, Lasers Surg. Med, 35(5):385-91 (ISSN: 0196-8092), Boston, MA, USA, 2004.
Silvestri, et al., "Selectively Preventing Development of Third Molars in Rats Using Electrosurgical Energy," Journal of the American Dental Association, vol. 135, No. 10, Boston, MA 02111, USA, Oct. 2004, 1397-1405.
Silvestri, et al., "The Unresolved Problem of the Third Molar: Would People Be Better Off Without It?" Journal of the American Dental Association, vol. 134, No. 4, 450-5, Boston, MA 02111, USA, Apr. 2003, 450-5.
Song, et al., "The Effectiveness and Cost-Effectiveness of Prophylactic Removal of Wisdom Teeth, Executive Summary," Health Technology Assessment, vol. 4, No. 15, 2000, 4 pages.
Swee, et al., "Inferior alveolar nerve block and third-molar agenesis: a retrospective clinical study," © 2014 American Dental Association, JADA, 144(4):389-395, 10.14219/jada.archive.2013.0132, USA, 2013.
U. S. Department of Labor, "Dentists," Webpage, last modified Dec. 17, 2009, 3 pages.
University of York, The, "Prophylactic Removal of Impacted Third Molars: Is It Justified?" Effectiveness Matters, vol. 3, Issue 2, Heslington, York, UK, Oct. 1998, 4 pages.
Venta, et al., "Change in Clinical Status of Third Molars in Adults during 12 Years of Observation," Abstract, Journal Oral Maxillofacial Surgery, 5794):386-9 (ISSN: 0278-2391) Helsinki, Finland, 1999.
Venta, et al., "Malpractice Claims for Permanent Nerve Injuries Related to Third Molar Removals," Abstract, Acta. Odontol. Scand, 56(4):193-6 (ISSN: 0001-6357), Helsinki, Finland, 1998.
Voegelin, et al., "Complications during and after Surgical Removal of Mandibular Third Molars. Impact of Patient Related and Anatomical Factors," Abstract, Schweiz Monatsschr Zahnmed, 118(3):192-8 Bern, Switzerland, 2008.
Wealthy Dentist, The, "Dental Marketing: Dentists Refer Some Wisdom Tooth Extractions to Oral Surgeons," The Wealthy Dentist.com, at Teast as early as 2008, Tiburon, CA 94920, USA, 5 pages.
Wikipedia, "Third Molar," Wikipedia, Webpage, last modified Apr. 19, 2011, 9 pages.
Wikipedia, "Tooth Development," Wikipedia, Webpage, last modified Apr. 18, 2011, 16 pages.
X-Nav Technologies, "How It Works: X-Guide Dynamic 3D Navigation™ Workflow," http://www.x-navtech.com/x-guide/how-it-works, at least as early as 2020, 2 pages.
Patent Cooperation Treaty, International Search Report and Written Opinion for PCT/US2020/036508, dated Nov. 17, 2020, 18 pages.
Patent Cooperation Treaty, International Search Report and Written Opinion for PCT/US2020/036705, dated Nov. 17, 2020, 18 pages.
Patent Cooperation Treaty, "International Preliminary Report on Patentability" for PCT/US2020/036508, dated May 18, 2021, 7 pages.

\* cited by examiner

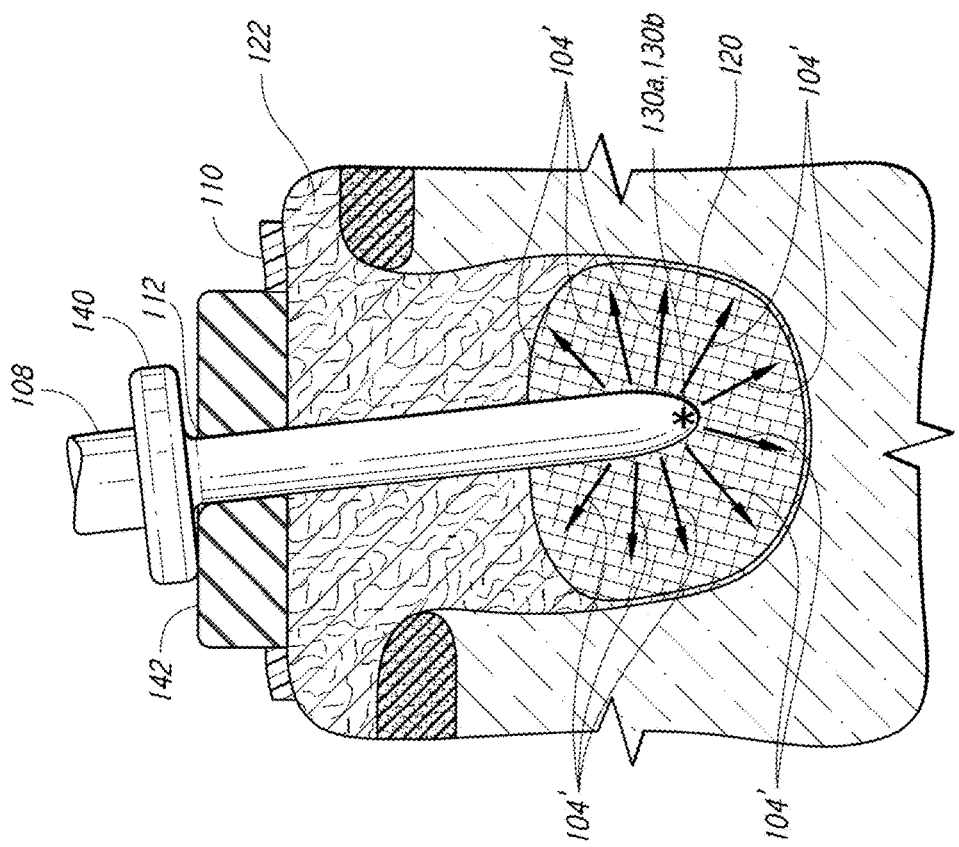
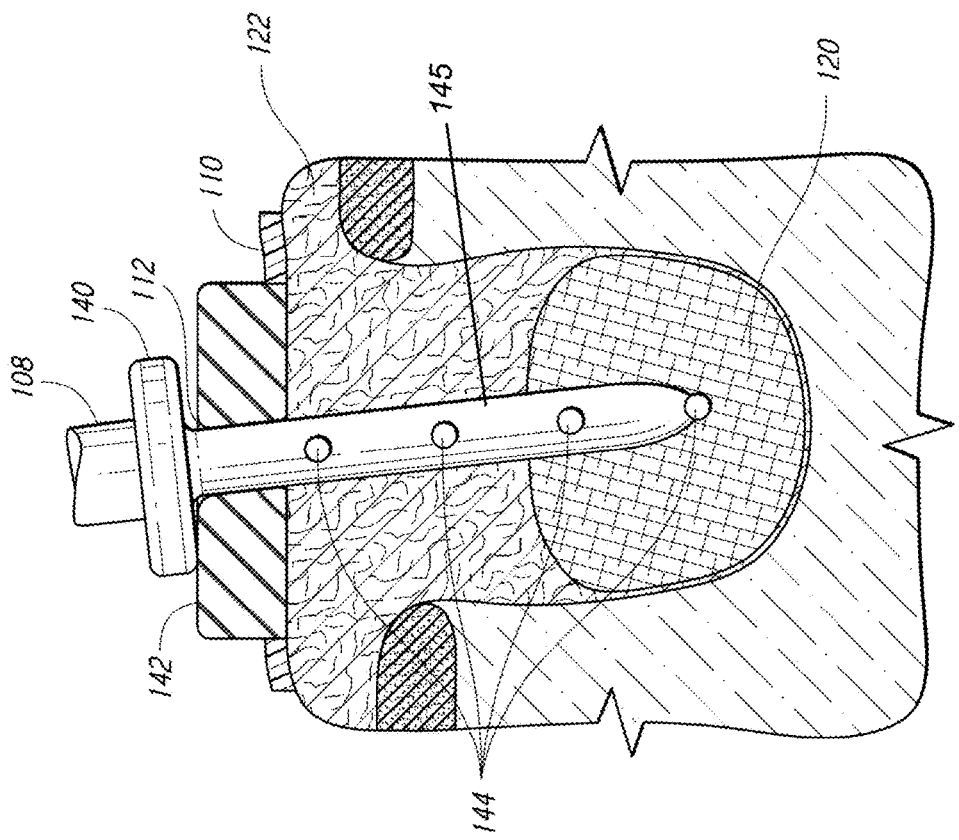

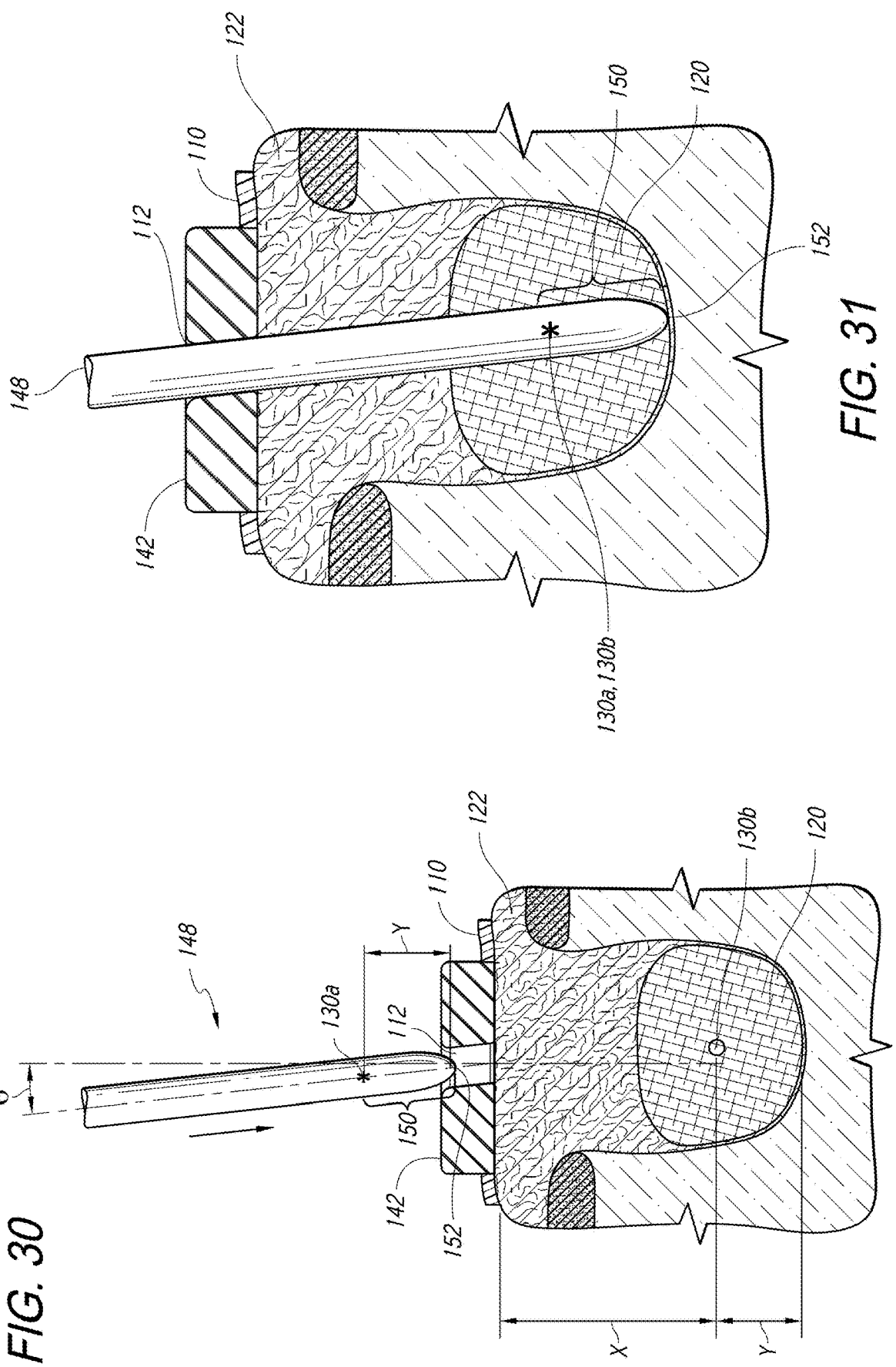

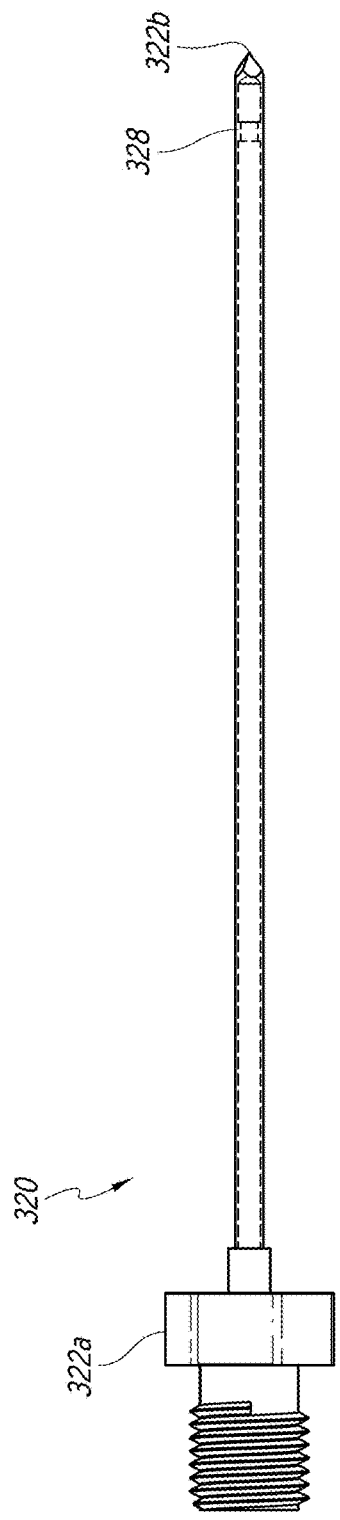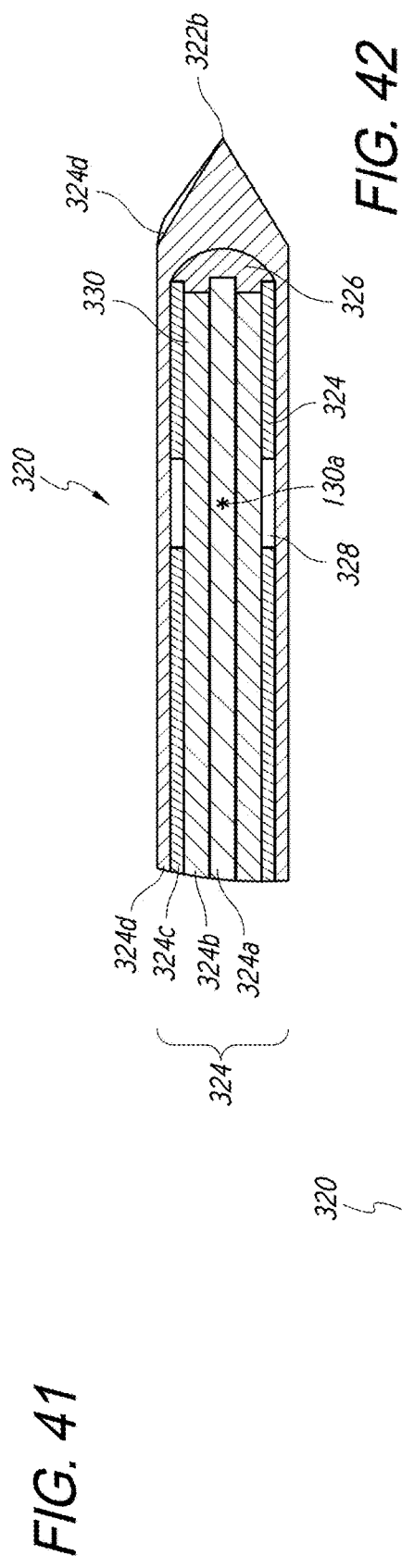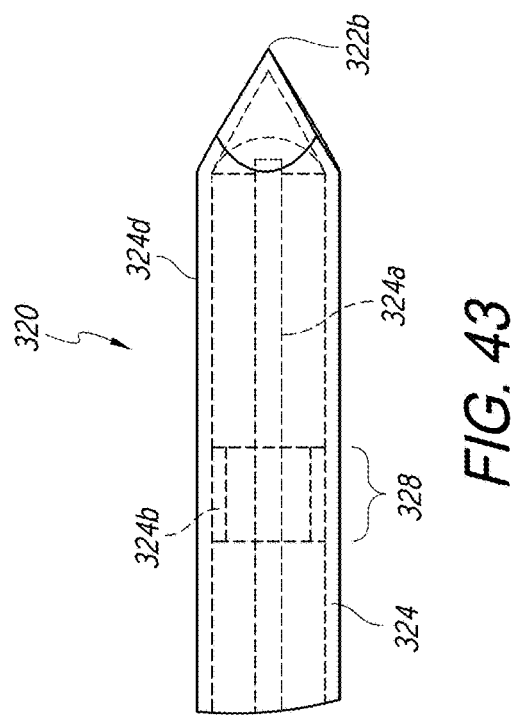

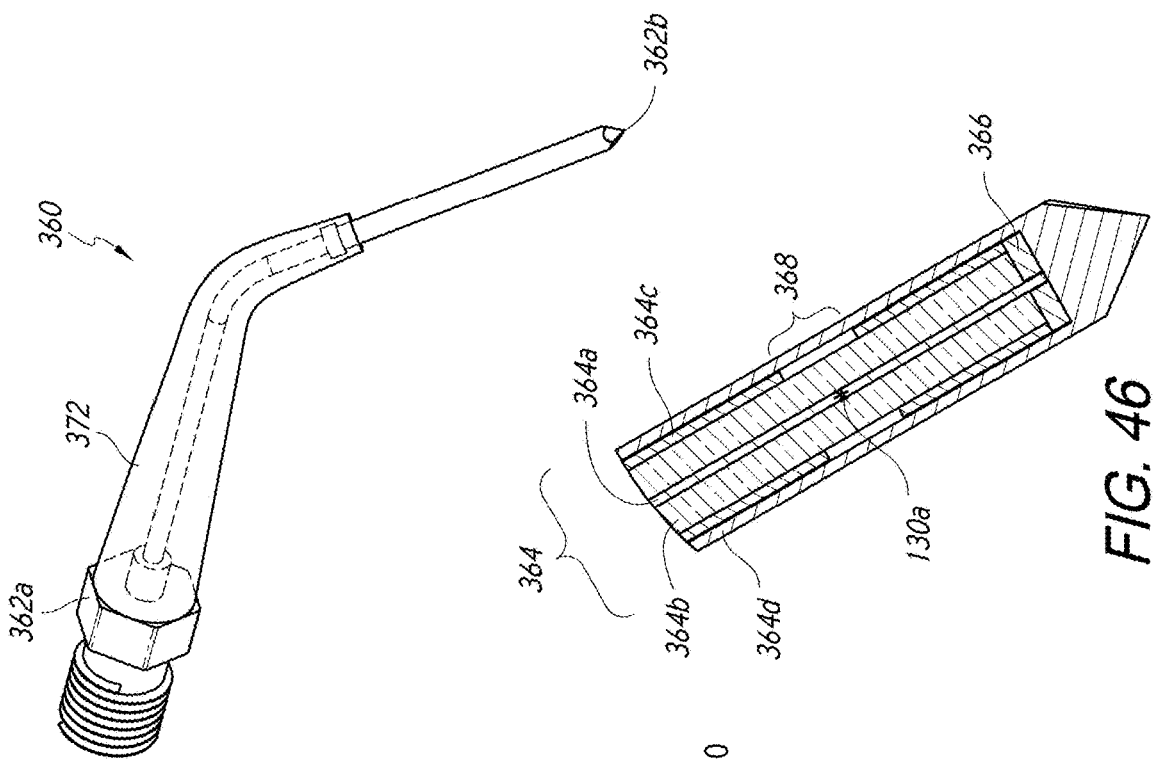
FIG. 44
FIG. 46
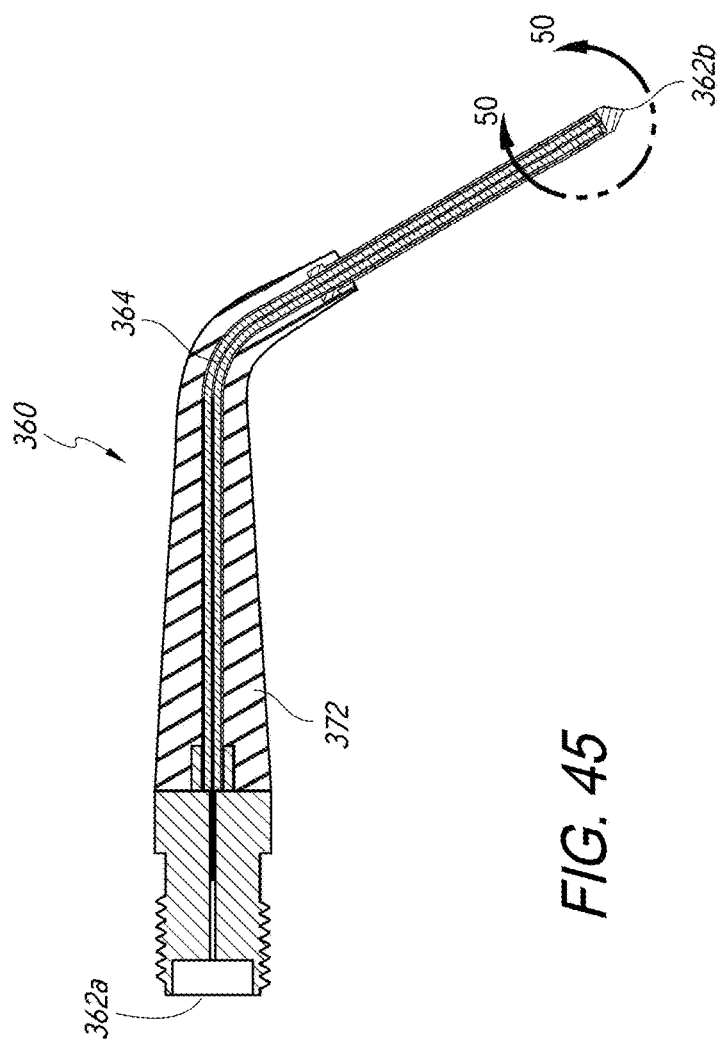
FIG. 45

THERAPEUTIC TOOTH BUD ABLATION

The present application is a continuation of U.S. patent application Ser. No. 16/418,944, filed May 21, 2019. U.S. patent application Ser. No. 16/418,944 is a continuation of U.S. patent application Ser. No. 16/036,904, filed Jul. 16, 2018. U.S. patent application Ser. No. 16/036,904 is a continuation of U.S. patent application Ser. No. 14/849,431, filed Sep. 9, 2015 that issued as U.S. Pat. No. 10,022,202 on Jul. 17, 2018. U.S. patent application Ser. No. 14/849,431 is a continuation of Patent Cooperation Treaty (PCT) Application Number PCT/US13/32357, filed Mar. 15, 2013. U.S. patent application Ser. No. 16/418,944 is also a continuation of U.S. patent application Ser. No. 15/829,874, filed Dec. 2, 2017 that issued as U.S. Pat. No. 10,298,255 on May 21, 2019. U.S. patent application Ser. No. 15/829,874 is a continuation of U.S. patent application Ser. No. 14/849,464, filed Sep. 9, 2015 that issued as U.S. Pat. No. 9,855,112 on Jan. 2, 2018. U.S. patent application Ser. No. 14/849,464 is a continuation of Patent Cooperation Treaty (PCT) Application Number PCT/US13/32357, filed Mar. 15, 2013. U.S. patent application Ser. No. 16/418,944 is also a continuation of U.S. patent application Ser. No. 15/215,020, filed Jul. 20, 2016 that issued as U.S. Pat. No. 10,335,248 on Jul. 2, 2019. The present application is based on and claims priority from these applications, the disclosures of which are hereby expressly incorporated herein by reference in their entirety.

COPYRIGHT NOTICE

A portion of the disclosure of this patent document contains material that is subject to copyright protection. The copyright owner has no objection to the facsimile reproduction of the patent disclosure as it appears in the Patent and Trademark Office patent files or records, but otherwise reserves all copyright rights whatsoever.

TECHNICAL FIELD

Described herein are a tooth bud ablation (TBA) procedure and a tooth bud ablation (TBA) system.

BACKGROUND OF THE INVENTION

Approximately 3.5% of the total $100 billion spent on dental care in the United States in 2008 was for traditional surgical removal of third molars (i.e. "wisdom teeth" extractions), including the associated costs of imaging, sedation, and resulting complications. Traditional surgical removal of third molars, however, is a highly invasive, painful, and complication-ridden procedure. Further, third molar extraction represents the only procedure in the United States and Europe where it is considered "normal" to subject patients of any age group to such a highly invasive prophylactic surgery that carries significant lifelong risks for the excision of asymptotic or non-pathologic tissue. Dental practitioners (e.g. general dentists, pediatric dentists, and oral surgeons) have been trained to remove children's wisdom teeth (third molars) before the wisdom teeth cause problems, but this surgery carries significant pain, risks and costs.

The main problem associated with third molar tooth extractions—aside from the pain inflicted—is the serious risk of complications associated with such an invasive procedure. Each year "more than 11 million patient days of 'standard discomfort or disability'—pain, swelling, bruising, and malaise—result post-operatively, and more than 11,000 people suffer permanent paraesthesia—numbness of the lip, tongue, and cheek—as a consequence of nerve injury during the surgery. At least two thirds of these extractions, associated costs, and injuries are unnecessary, constituting a silent epidemic of iatrogenic injury that afflicts tens of thousands of people with lifelong discomfort and disability."

If you interview people under the age of 40 and ask them what has been the most invasive surgical procedure they have personally experienced (that is not trauma related), there is a greater than 90% chance that it will be their "wisdom teeth" extraction. The current standard of care in America for "managing" third molars (e.g. "wisdom teeth") in adolescents and young adults is generally to have all four third molars extracted once they are formed, unless it is absolutely clear that these teeth will erupt normally. General dentists and oral surgeons alike are complicit in their belief that third molars generally should be extracted because not all will erupt normally, thus causing future pathology.

Each year, an estimated 10 million third molar tooth extractions account for over 92% of all teeth extracted for patients under the age of 40. This represents surgery on approximately 5 million people each year at an estimated cost of over $2.5 billion for third molar extraction fees alone in the United States. When IV sedation fees, X-ray imaging expenses, post-op medications, and unplanned post-operative expenses associated with treating complications are added in, the true United States health care cost is estimated to be well over $3.5 billion. In addition to fee inflation, it has been shown that "upcoding" of wisdom teeth extraction (i.e. using an insurance code for payment of a higher fee than is clinically justified) has become an increasing problem for insurers. Insurance claim patterns clearly show that this procedure is largely treated as an elective procedure. The average annual income per oral surgeon has been estimated to be approximately $500,000 for third molar extraction fees alone. Insurance companies have historically reported that reimbursement for third molar extractions has been the highest reimbursed surgical procedure—even higher than hysterectomies in years when medical insurance used to pay for both procedures.

The market demographics and associated expenses are compelling. Over 77% of children at age 6 have all four third molar tooth buds radiographically detectable on routine panographic X-rays (a type of volume scan). Over 90% of all teenagers in the United States have at least one third molar that will fully form. A typical cost for an oral surgeon to remove all four third molars on a teenager is generally $2,000 to $2,500 per patient once the teeth have at least partially formed—but before they have erupted—including the cost of IV sedation, consultations, and X-ray imaging costs.

There has been considerable controversy for the past fifty years regarding prophylactic extraction of third molars. A number of leading authorities have objectively tried to demonstrate that prophylactic extraction is a waste of healthcare dollars, citing studies that indicate there is no objective scientific evidence for such a procedure, while other groups vigorously argue that prophylactic extraction in the teens and early adult years greatly eliminates more serious problems later in life and is worth the cost and risk.

An important question to ask is, "What happens if no prophylactic third molar extractions occur?" For instance, "as many as 22% of all emergency department visits" at a United States military support facility were related to dental problems, most of which were third-molar specific. In third-world countries, where prophylactic extraction of wisdom teeth is simply not performed, a high percentage of patients will present with acute infections, decay, gum disease and other problems later in life. In Jordan—where prophylactic extraction is not performed—46% of adult patients had pathology (decay, infection, bone loss, etc.) detectable on their third molars on routine X-rays and volume scans. Numerous studies show that third molars are hard to clean, generally do not erupt fully, and are the single most-likely teeth to have problems associated with them.

Routine panographic X-rays of adults taken during a random two-week period are shown in FIGS. 1 and 2. These X-rays show the examples of the range of problems that adult patients experience when they have third molars that are not extracted at an early age, including advanced decay and gum infections. For example, FIG. 1 shows a 48-year-old patient with both upper third molars present. There is a gum infection around both third molars that has caused 90% of the bone on the distal side of the second molars to be destroyed. In order to save the first molars, extraction of the second and third molars on the upper-arch will be necessary. FIG. 2 shows another example in which a 36-year-old patient has all four third molars present. The upper third molars are hyper-erupting because they have no opposing teeth to occlude against. They will eventually need to be extracted. The lower third molars are horizontally impacted and show no signs of infection, but if they become infected, then the patient will almost certainly lose the adjacent second molars because of the bone damage that will occur.

The problem all practitioners face is that it is practically impossible to tell in advance which impacted wisdom teeth will ultimately cause future pathology. The reality is that most wisdom teeth (well over 50%) are surgically extracted prophylactically with no real knowledge that they will actually cause future pathology.

If pathology appears in patients over the age of 40, however, the stakes are much different. According to two prospective studies in the United States, in 1997 10.5% and in 2002 17.3% of patients requiring third molar extractions were over the age of 40. If a patient is presenting later in life to have one or more third molars extracted, it is because active pathology has been diagnosed, making surgery no longer elective. The attendant complication rates are not just higher, but these patients were categorized as "very high risk patients" for surgery. These studies concluded, "[t]he risk to patients and to the profession can be dramatically reduced by considering early removal of abnormal third molars" and "based on our experience, we propose extraction of third molars during adolescence when the X-ray indicates normal eruption cannot be expected due to lack of space or an abnormal position."

The occurrence of post-operative complications is generally considered to be over 15% by most independent researchers. For instance, the formation of long-term periodontal pockets on the distal surfaces of second molars that results in gum disease, infection, and eventual second molar tooth loss is estimated to be over 10% due to the damage and poor bone morphology that result from third molar extraction surgery. The incidence of post-operative infections and "dry sockets" is generally accepted to be over 15%. Temporary paraesthesia due to damage to the mandibular nerve or the lingual nerve is over 10%, with residual permanent numbness of the lip or tongue present in approximately 1.5% of all patients. Recently, it has been concluded that approximately 23% of all cases of long-term Temporomandibular Joint ("TMJ") dysfunction and chronic joint pain are attributable to third molar extraction surgeries.

Malpractice claims against dental practitioners relating to third molar extractions are at an all time high. Litigation for residual TMJ problems is increasing; in 2002 a North Carolina jury awarded $5 million in damages to a patient with TMJ pain following third molar extractions. The incidence of litigation over permanent numbness of the lip has dramatically increased in recent years. Malpractice claims with resulting payouts have been reported to be as high as two-thirds of all claims made against dental practitioners when nerve damage is involved.

If the wisdom teeth are not extracted in adolescence, the roots will fully form, making future extraction difficult and dramatically increasing the incidence of serious complications if surgery should later be required. The damage induced by long-standing, chronic infections in adults may necessitate the extraction not only of the third molars when they become symptomatic, but also of the adjacent second molars. Additional complications include the reduced healing response of adults as compared to adolescents, and the economic hardship induced by having to miss work. Many references indicate that prophylactic extraction of third molars in teens and young adults—in spite of the possibility of lifelong complications such as nerve damage—is justified to avoid the non-elective third molar extraction in adults over the age of 30.

Complications can be severe, even requiring hospitalization when teeth have been extracted on an out-patient basis. There have even been reports of patients who died as a direct result of wisdom tooth extractions.

As an example, FIG. 3 is an X-ray showing a 9-year-old patient with four third molar tooth buds present; three of them are in very early stages of enamel formation. The lower right third molar tooth bud does not have enamel formed yet, but will shortly. This X-ray shows an example of the early stages in which the tiny third molar tooth buds begin to form, begin to develop enamel, and finally begin to develop roots. Early signs of problems are almost always clearly evident by the time a patient is a teenager.

Once the tooth starts to form, the tooth bud starts to become encased in bone and appears to be "pushed down" into the mandible and maxilla as the child's jaw bone grows out and around the tooth bud with age. Future surgical access becomes far more invasive as the bone encases the forming third molar. Given the basic physiology involved, early intervention is the only approach that will eliminate the complications and high costs associated with extraction of fully formed third molars later in life.

The idea of prophylactic third molar tooth bud removal is not new. In 1936, Dr. Henry supported the surgical enucleation of tooth buds, and it was again supported in the mid 70s by several practitioners using somewhat invasive surgical techniques to physically access the tooth buds and mechanically cut them out. In 1979, Drs. Gordon and Laskin used cryoprobes to enucleate third molar tooth buds in dogs. However, at the NIH Conference On Third Molars in 1979 it was concluded that "[a]lthough there are cogent reasons for early removal of third molars, the group felt that the suggested practice of enucleation of third molar tooth buds, based on predictive studies at age 7 to 9, is not currently acceptable." (National Institutes of Health—*Removal Of Third Molars Consensus Development Conference Statement*—1979.)

Early removal of partially formed third molars (sometimes referred to as a "germectomy") where the enamel of the crown has completely formed but less than one-third of the root length has formed, is demonstrated to be somewhat less invasive and carries no demonstrated long-term complications or risks associated with early-stage surgery. However, it is still highly invasive and generally requires IV sedation of the teenage patient. The American Association of Oral & Maxillofacial Surgeon's *White Paper On Third Molar Data* references five studies involving over 1,100 germectomies with not a single case of a long-term complication (nerve injury, etc.) associated with the surgery. Further, since the germectomies were carried out on teenagers, there were no economic hardships induced by missing work. The *White Paper* understates the obvious conclusions associated with early intervention: "It does appear that early third molar removal may be associated with a lower incidence of morbidity and also less economic hardship from time off work for the patient." However, it can also be concluded that there was a tremendous conflict of interest because this paper was written by oral surgeons. To date there is still no measurable shift by dental practitioners to change the way in which third molars are screened, diagnosed, and extracted (i.e. early extraction), indicating that there is a need to fundamentally change the way this condition is being surgically managed.

There are a number of existing alternative technical approaches that can be considered for prophylactic enucleation of third molar tooth buds before the crown or root begins formation in children age 6 to 10. These technical approaches include ablation procedures using different types of ablation means. Exemplary ablation procedures include microwave ablation, radio frequency ablation, irreversible electroporation, electrosurge tissue ablation (rats), cryoablation (dogs), laser ablation (dogs), and the use of a scalpel (humans). All but the first three ablation procedures have significant limitations due to being highly invasive, high in cost, requiring cumbersome equipment, or due to the limited means of mechanical access in the oral cavity. Nor do these ablation procedures offer the potential for real-time feedback control to contain collateral tissue damage. To date, the only documented trial of any form of tooth bud ablation procedure utilizing ablation technology that is currently used in mainstream medicine is cryoablation (although preliminary animal trials have been completed using electrosurgical power and lasers).

The article entitled "Selectively Preventing Development Of Third Molars In Rats Using Electrosurgical Energy" by Silvestri et al. describes a pilot study that tests the hypothesis that third molars can be selectively prevented from developing. To test the hypothesis, a study was conducted in which thirty-three neonate rats received electrosurgical energy to the mucosal surfaces of one of their maxillary tuberosities. In this study, guides (insulating plastic positioning devices that housed the electrosurgical probes) were used. The guides were fabricated using the mouths of euthanized rat pups of the same age as the rats that were to be treated as a mold for creating the guides. Then, the electrosurgical probe placed so that its stainless steel tip extended less than 1.0 mm beyond the plastic positioning device to ensure contact with the external surface of the oral mucosa of the maxillary tuberosity. Finally, when in position, the rat pups received a single, unilateral, momentary pulse of monopolar electrosurgical energy to the external surface of the gum tissue of their maxillary tuberosity regions. It should be emphasized that this surface application of electrosurgical energy acted first to unnecessarily kill the overlying gum tissue, then bore a hole through the gum tissue, and otherwise damage not only the tooth buds, but other nearby tissue. The rats were cared for, but after the experimental period, were euthanized to determine the effectiveness of the procedure. The results were that ten rats showed no intra-oral or radiographic evidence of third molar development (and most of these rats subsequently developed palatal deformities), and six developed smaller-than-normal third molars. The conclusion was that maxillary third molars could be selectively prevented from developing in rat pups at or near the time of tooth bud initiation. It was recognized, however, that electrosurgical energy was too powerful and uncontrollable to reliably confine its damage to only the tooth-forming tissues.

U.S. Pat. No. 5,688,118 to Hayka et al. (the "Hayka reference") discloses image, sound, and feeling simulation system for dentistry. The system described in the Hayka reference can be thought of as a virtual system that may be used for implanting teeth. Such a virtual system connects the patient to the implant hand piece (i.e. "the drill"). Using three-dimensional scans on a display, the operator theoretically can guide movement of the drill bit relative to the patient for example, to allow the operator to guide the drill bit into the bone and place the implant. The Hayka reference includes a dental hand piece having a drill for drilling a cavity in a tooth, the drill having a drilling end; a first three-dimensional sensor attached to the dental hand piece, the first three-dimensional sensor providing the system with position and orientation in space of at least the drill; and a data processing and display unit for simulating at least the drilling end of the drill. Other patents and published patent applications that address aspects of virtual dentistry include U.S. Pat. No. 8,221,121 to Berckmans, III et al., U.S. Pat. No. 8,013,853 to Douglas, et al., U.S. Pat. No. 7,812,815 to Banerjee, et al., U.S. Pat. No. 7,457,443 to Persky, U.S. Pat. No. 7,249,952 to Ranta, et al., U.S. Patent Publication No. 20100316974 to Yau, et al., U.S. Patent Publication No. 20100311028 to Bell, et al., and U.S. Patent Publication No. 20090253095 to Salcedo, et al.

SUMMARY OF THE INVENTION

Disclosed herein is an ablation probe tip for use in a tooth bud ablation procedure that results in tooth agenesis. The ablation probe tip may be used with a stent and an ablation probe unit. The ablation probe tip preferably has a shaft and a center of ablation. The shaft preferably has an insertion end for inserting into a tooth bud and a connection end for connecting the ablation probe tip to the ablation probe unit. The ablation probe tip preferably has a center of ablation between the insertion end and the connection end. The ablation probe tip may be guidable at a pre-defined angle (preferably a three-dimensional angle) when used in conjunction with the stent. The ablation probe tip may be depth limited by stop information (stop indicator(s)) to a pre-defined depth. The center of ablation substantially coincides with or overlaps with the middle of the tooth bud when the ablation probe tip is guided at the pre-defined angle to the pre-defined depth.

The stent may be a physical stent that has mechanical stop structure and the ablation probe tip may have mechanical stop structure. The stop information in this situation would be a physical prevention of progression of the ablation probe tip provided by interaction of the mechanical stop structures.

The ablation probe tip may have extension stop structure between the center of ablation and an absolute tip at the insertion end of the ablation probe tip. The stop information in this situation would be physical prevention of progression of the ablation probe tip provided by interaction of the absolute tip with bone below or above the tooth bud.

The stent may be a virtual stent that has a display and the ablation probe tip may be a sensored ablation probe tip. A representation of the sensored ablation probe tip may be displayed on the display. The sensored ablation probe tip may be guidable at the pre-defined angle by virtual surgical guide angle markings displayed on the display.

The pre-defined angle may be a three-dimensional angle and the stent may be a virtual stent having a display. The ablation probe tip may be a sensored ablation probe tip, and a representation of the sensored ablation probe tip may be displayed on the display, the sensored ablation probe tip may be guidable at the three-dimensional pre-defined angle by virtual surgical guide angle markings displayed on the display.

The stent may be a virtual stent that has a display and the ablation probe tip may be a sensored ablation probe tip. A representation of the sensored ablation probe tip may be displayed on the display. The stop information (stop indicator(s)) in this situation would be provided by a virtual stop marking on the display.

The stent may be a virtual stent having a display and the hand piece may be a sensored hand piece. A representation of the sensored hand piece may be displayed on the display. The stop information (stop indicator(s)) in this situation would be provided by a virtual stop marking on the display.

The stent may be a virtual stent, and the ablation probe tip may be a sensored ablation probe tip. The stop information (stop indicator(s)) in this situation would be provided by an indicator such as a visual indicator, an audible indicator, a tactile indicator, or a combination of indicators.

The ablation probe tip preferably has a shaft inner conductor, shaft insulation surrounding the shaft inner conductor, a shaft outer shield surrounding the shaft insulation, a window defined in the shaft outer shield, a shaft outer cover surrounding the shaft outer shield and the window, and a reflector positioned between the window and the insertion end. The center of ablation is preferably positioned in the shaft inner conductor at the window, wherein the center of ablation is a focal point (focal area) from which ablation means radiates through the window.

The ablation probe tip preferably has a shaft inner conductor, shaft insulation surrounding the shaft inner conductor, a shaft outer shield surrounding the shaft insulation, a window defined in the shaft outer shield, a shaft outer cover surrounding the shaft outer shield and the window, and a deposited metal reflector positioned between the window and the insertion end. The center of ablation is preferably positioned in the shaft inner conductor at the window, wherein the center of ablation is a focal point (focal area) from which ablation means radiates through the window.

The ablation probe tip preferably has a shaft inner conductor, shaft insulation surrounding the shaft inner conductor, a shaft outer shield surrounding the shaft insulation, a window defined in the shaft outer shield, a shaft outer cover surrounding the shaft outer shield and the window, and a soldered reflector positioned between the window and the insertion end. The center of ablation is preferably positioned in the shaft inner conductor at the window, wherein the center of ablation is a focal point (focal area) from which ablation means radiates through the window.

The ablation probe tip preferably has a shaft inner conductor, shaft insulation surrounding the shaft inner conductor, a shaft outer shield surrounding the shaft insulation, a window defined in the shaft outer shield, a shaft outer cover surrounding the shaft outer shield and the window, and an electroplated reflector positioned between the window and the insertion end. The center of ablation is preferably positioned in the shaft inner conductor at the window, wherein the center of ablation is a focal point (focal area) from which ablation means radiates through the window.

The ablation probe tip preferably has a shaft inner conductor, shaft insulation surrounding the shaft inner conductor, a shaft outer shield surrounding the shaft insulation, a gap window defined in the shaft outer shield, a shaft outer cover surrounding the shaft outer shield and the gap window, and a reflector positioned between the gap window and the insertion end. The center of ablation is preferably positioned in the shaft inner conductor at the gap window, wherein the center of ablation is a focal point (focal area) from which ablation means radiates through the gap window.

The ablation probe tip preferably has a shaft inner conductor, shaft insulation surrounding the shaft inner conductor, a shaft outer shield surrounding the shaft insulation, a gap window defined in the shaft outer shield, a shaft outer cover surrounding the shaft outer shield and the gap window, and a deposited metal reflector positioned between the gap window and the insertion end. The center of ablation is preferably positioned in the shaft inner conductor at the gap window, wherein the center of ablation is a focal point (focal area) from which ablation means radiates through the gap window.

The ablation probe tip preferably has a shaft inner conductor, shaft insulation surrounding the shaft inner conductor, a shaft outer shield surrounding the shaft insulation, a gap window defined in the shaft outer shield, a shaft outer cover surrounding the shaft outer shield and the gap window, and a soldered reflector positioned between the gap window and the insertion end. The center of ablation is preferably positioned in the shaft inner conductor at the gap window, wherein the center of ablation is a focal point (focal area) from which ablation means radiates through the gap window.

The ablation probe tip preferably has a shaft inner conductor, shaft insulation surrounding the shaft inner conductor, a shaft outer shield surrounding the shaft insulation, a gap window defined in the shaft outer shield, a shaft outer cover surrounding the shaft outer shield and the gap window, and an electroplated reflector positioned between the gap window and the insertion end. The center of ablation is preferably positioned in the shaft inner conductor at the gap window, wherein the center of ablation is a focal point (focal area) from which ablation means radiates through the gap window.

The ablation probe tip preferably has a shaft inner conductor, shaft insulation surrounding the shaft inner conductor, a shaft outer shield surrounding the shaft insulation, an air gap window defined in the shaft outer shield, a shaft outer cover surrounding the shaft outer shield and the air gap window, and a reflector positioned between the air gap window and the insertion end. The center of ablation is preferably positioned in the shaft inner conductor at the air gap window, wherein the center of ablation is a focal point (focal area) from which ablation means radiates through the air gap window.

The ablation probe tip preferably has a shaft inner conductor, shaft insulation surrounding the shaft inner conductor, a shaft outer shield surrounding the shaft insulation, an air gap window defined in the shaft outer shield, a shaft outer cover surrounding the shaft outer shield and the air gap window, and a deposited metal reflector positioned between the air gap window and the insertion end. The center of ablation is preferably positioned in the shaft inner conductor at the air gap window, wherein the center of ablation is a focal point (focal area) from which ablation means radiates through the air gap window.

The ablation probe tip preferably has a shaft inner conductor, shaft insulation surrounding the shaft inner conductor, a shaft outer shield surrounding the shaft insulation, an air gap window defined in the shaft outer shield, a shaft outer cover surrounding the shaft outer shield and the air gap window, and a soldered reflector positioned between the air gap window and the insertion end. The center of ablation is preferably positioned in the shaft inner conductor at the air gap window, wherein the center of ablation is a focal point (focal area) from which ablation means radiates through the air gap window.

The ablation probe tip preferably has a shaft inner conductor, shaft insulation surrounding the shaft inner conductor, a shaft outer shield surrounding the shaft insulation, an air gap window defined in the shaft outer shield, a shaft outer cover surrounding the shaft outer shield and the air gap window, and an electroplated reflector positioned between the air gap window and the insertion end. The center of ablation is preferably positioned in the shaft inner conductor at the air gap window, wherein the center of ablation is a focal point (focal area) from which ablation means radiates through the air gap window.

The pre-defined angle may be based on information obtained from a volume scan image. The pre-defined depth may be based on information obtained from a volume scan image.

The ablation probe tip may be used for gaining access to the at least one tooth bud without causing necrosis to surrounding gingival tissue. The ablation probe tip may be used for at least partially ablating at least one tooth bud by creating a zone of ablation that resides only within the at least one tooth bud. The ablation probe tip may be used for at least partially ablating at least one tooth bud without ablating surrounding gingival tissue. The ablation probe tip may be used for at least partially ablating at least one tooth bud without ablating surrounding tissue.

The ablation probe tip may have a center of ablation is positioned within approximately 50% of an average diameter of the tooth bud when the ablation probe tip is at the pre-defined angle and the pre-defined depth. The ablation probe tip may have a center of ablation is positioned within approximately 25% of an average diameter of the tooth bud when the ablation probe tip is at the pre-defined angle and the pre-defined depth. The ablation probe tip may have a center of ablation is positioned within approximately 10% of an average diameter of the tooth bud when the ablation probe tip is at the pre-defined angle and the pre-defined depth.

An ablation probe tip may be used for use in a tooth bud ablation procedure that results in tooth agenesis. The tooth bud preferably has a middle. The ablation probe tip may be used with an ablation probe unit. The ablation probe tip may preferably has a shaft, the shaft preferably having an insertion end for inserting into a tooth bud and a connection end for connecting the ablation probe tip to the ablation probe unit. The ablation probe tip preferably has a center of ablation between the insertion end and the connection end. The ablation probe tip preferably has a shaft inner conductor, shaft insulation surrounding the shaft inner conductor, a shaft outer shield surrounding the shaft insulation, a window defined in the shaft outer shield, a shaft outer cover surrounding the shaft outer shield and the window, and a reflector positioned between the window and the insertion end. The center of ablation is preferably positioned in the shaft inner conductor at the window. The center of ablation is preferably a focal point from which ablation means radiates through the window, the center of ablation may be positionable to substantially coincide with or overlap with the middle of the tooth bud.

The reflector may be a deposited metal reflector, a solder metal reflector, or an electroplated metal reflector. The window may be a gap window or an air gap window.

A virtual stent as described herein is preferably for use in a tooth bud ablation procedure that results in tooth agenesis. The tooth bud preferably has a middle. The virtual stent is preferably for use with a sensored ablation probe tip having an insertion end and a connection end. The sensored ablation probe tip preferably has a center of ablation between the insertion end and the connection end. The stent preferably includes a display upon which a representation of the sensored ablation probe tip may be displayed. At least one virtual surgical guide angle marking is preferably displayable on the display, the at least one virtual surgical guide angle marking providing angle guidance to guide the sensored ablation probe tip at a pre-defined angle. At least one virtual stop marking is preferably displayable on the display providing stop information to limit the depth of the sensored ablation probe tip to a pre-defined depth. The center of ablation substantially coincides with or overlaps with the middle of the tooth bud when the sensored ablation probe tip is guided at the pre-defined angle to the pre-defined depth.

The pre-defined angle may be a three-dimensional angle. The virtual stent may be used with a sensored hand piece connectable to the connection end of the sensored ablation probe tip. In such a case, the representation of the sensored hand piece may be displayed on the display. The three-dimensional volume scan may be displayed on the display. The display may display a real time relationship between the center of ablation as compared to the middle of the tooth bud.

Stop information may be provided by an indicator selected from the group consisting of a visual indicator, an audible indicator, a tactile indicator, or a combination of indicators.

The pre-defined angle may be based on information obtained from a volume scan image. The stent pre-defined depth may be based on information obtained from a volume scan image.

A tooth bud ablation method for ablating a tooth bud using a virtual stent may include the following steps: providing the virtual stent and a sensored ablation probe tip; introducing the sensored ablation probe tip to the tooth bud, the introduction may be displayed in real time on the display; using the at least one virtual surgical guide angle marking and the at least one virtual stop marking; guiding the sensored ablation probe tip towards the position where the center of ablation substantially coincides with or overlaps with the middle of the tooth bud, the guidance may be displayed in real time on the display; and using ablation means, ablating the tooth bud when the center of ablation substantially coincides with or overlaps with the middle of the tooth bud.

The step of ablating preferably results in tooth agenesis.

The method may further include the step of setting parameters to be used for guiding the sensored ablation probe tip and for ablating the tooth bud. The method may further include the step of calibrating the display and the sensored ablation probe tip so that the sensored ablation probe tip is properly represented on the display.

The method may further include the following steps: introducing a sensored anesthetic needle to the tooth bud, the introduction may be displayed in real time on the display; using the at least one virtual surgical guide angle marking and the at least one virtual stop marking; guiding the sensored anesthetic needle towards the middle of the tooth bud, the guidance may be displayed in real time on the display; and anesthetizing the tooth bud when the sensored anesthetic needle reaches the middle of the tooth bud.

The method may further include the step of providing visual, audible, and/or tactile indications to indicate that the center of ablation substantially coincides with or overlaps with the middle of the tooth bud.

The method further includes the step of monitoring progress of the ablating. Further, constant feedback pertaining to the progress may be provided.

The method may include the step of providing monitoring and overriding safeguards to allow automatic or manual cessation of ablation.

Described herein is an ablation probe tip for use in a tooth bud ablation procedure that results in tooth agenesis. The ablation probe tip may be used with a surgical stent or a virtual stent system. The ablation probe tip may be used with an ablation probe unit. The ablation probe tip has a shaft, the shaft having an insertion end for inserting into a tooth bud and a connection end for connecting the ablation probe tip to the ablation probe unit. The ablation probe tip has a center of ablation between the insertion end and the connection end. The shaft of the ablation probe tip being guidable at a pre-defined angle when used in conjunction with the stent. The ablation probe tip has structure that limits the depth of the ablation probe tip to a pre-defined depth when used in conjunction with the surgical stent; wherein the center of ablation is in the middle of a tooth bud when used in conjunction with the surgical stent; wherein the center of ablation is in the middle of a tooth bud when the ablation probe tip is at the pre-defined angle and the pre-defined depth.

Described herein is a tooth bud ablation procedure that results in tooth agenesis, including the steps of: physically seating a custom surgical stent having at least one surgical guide so the at least one surgical guide corresponds to at least one tooth bud surgical site; using the at least one surgical guide, making a surgical access path at the at least one tooth bud surgical site; using the at least one surgical guide, guiding placement of an ablation probe tip having a center of ablation so that the center of ablation is in the middle of a tooth bud at the at least one tooth bud surgical site; and at least partially ablating at least one tooth bud.

Described herein is a tooth bud ablation system for use in a tooth bud ablation procedure that results in tooth agenesis, the system including: a custom surgical stent with at least one surgical guide corresponding to at least one tooth bud surgical site; an ablation probe tip having a center of ablation; and the at least one surgical guide having structure for guiding placement of the ablation probe tip so that the center of ablation is in the middle of a tooth bud by inserting the ablation probe tip through the at least one surgical guide.

Described herein is an ablation procedure including the steps of: physically seating a custom surgical stent having at least one surgical guide so the at least one surgical guide corresponds to at least one lesion or tumor surgical site; using the at least one surgical guide, making a surgical access path at the at least one lesion or tumor surgical site; using the at least one surgical guide, guiding placement of an ablation probe tip having a center of ablation so that the center of ablation is in the middle of a lesion or tumor at the at least one lesion or tumor surgical site; and at least partially ablating at least one lesion or tumor.

Described herein is an ablation procedure including the steps of: physically seating a custom surgical stent having at least one surgical guide so the at least one surgical guide corresponds to at least one lesion or tumor surgical site; using the at least one surgical guide, guiding placement of an ablation probe tip having a center of ablation so that the center of ablation is in the middle of a lesion or tumor at the at least one lesion or tumor surgical site; and at least partially ablating at least one lesion or tumor.

Described herein is a method for volume scanning both hard tissues and soft tissues of a patient, the method including the steps of: using a physical impression of a material visible in a volume scan; generating a volume scan in which hard tissue is visible and the physical impression is visible, and soft tissue being "visible" as the space between the visible hard tissue and the visible physical impression; and providing results of the step of generating a volume scan for the purpose of manufacturing or fabricating a custom surgical stent having at least one surgical guide for guiding placement of an ablation probe tip. An alternative method for volume scanning both hard tissues and soft tissues of a patient replaces the physical impression with a digital impression.

Described herein is a method for simultaneous volume scanning of both hard tissues and soft tissues, the method including the steps of: using a physical dental impression of a material visible in a volume scan; physically seating the physical dental impression in a patient's mouth; volume scanning the patient's mouth while the physical dental impression is seated therein; the step of volume scanning generating a volume scan in which hard tissue is visible and the physical dental impression is visible, and soft tissue is "visible" as the space between the visible hard tissue and the visible dental impression; and providing the results of the step of volume scanning for the purpose of manufacturing or fabricating a custom surgical stent having at least one surgical guide for guiding placement of an ablation probe tip. An alternative method for volume scanning both hard tissues and soft tissues of a patient replaces the physical dental impression with a digital impression.

Described herein is a method for manufacturing or fabricating a custom surgical stent, the method including the steps of: using a volume scan image in which hard tissue is visible and a physical dental impression is visible, and soft tissue is "visible" as the space between the visible hard tissue and the physical visible dental impression; and manufacturing or fabricating a custom surgical stent with at least one ablation probe tip guide for guiding at least one ablation probe tip to a pre-defined angle and depth of ablation based on information obtained from the volume scan image. An alternative method for volume scanning both hard tissues and soft tissues of a patient replaces the physical dental impression with a digital impression.

Described herein is a tooth bud ablation procedure that results in tooth agenesis, including the steps of: pre-operatively taking measurements to determine a three-dimensional location of the middle of a tooth bud; placing an ablation probe tip having a center of ablation so that the center of ablation is in the three-dimensional location of the middle of a tooth bud; and at least partially ablating at least one tooth bud.

Described herein is a custom surgical stent for use in a tooth bud ablation procedure that results in tooth agenesis, the custom surgical stent for use with an ablation probe tip having a center of ablation, the stent including: a custom surgical stent with at least one surgical guide corresponding to at least one tooth bud surgical site; the at least one surgical guide having guiding structure to guide placement of an ablation probe tip at a pre-defined angle so that a center of ablation of the ablation probe tip is in the middle of a tooth bud; and the at least one surgical guide having mechanical stop structure to limit the depth of the ablation probe tip to a pre-defined depth.

The foregoing and other objectives, features, and advantages of the invention will be more readily understood upon consideration of the following detailed description of the invention, taken in conjunction with the accompanying drawings.

BRIEF DESCRIPTION OF THE DRAWINGS

The accompanying drawings are incorporated in and constitute a part of this specification.

FIG. 8 is a cross-sectional side view of an ablation probe tip having a linear array of temperature sensors inserted in the tooth bud.

FIG. 9 is a cross-sectional side view of an ablation probe tip ablating the tooth bud.

FIG. 30 is a cross-sectional side view of an alternative ablation probe tip in the process of being inserted through a surgical guide of a stent.

FIG. 31 is a cross-sectional side view of an alternative ablation probe tip inserted through a surgical guide of a stent into the tooth bud.

and status simultaneously shown on the display in real time, the position shown as 8% (close to the middle of the tooth bud) and the status shown as active.

Figure 39:
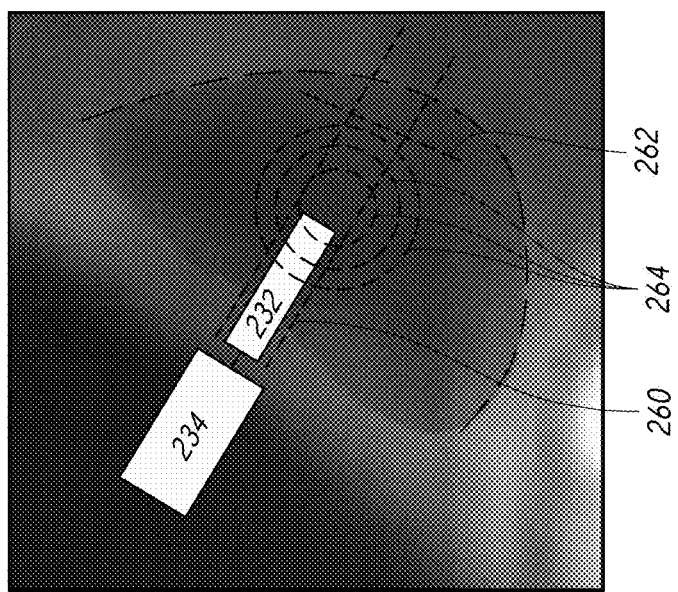

FIG. 39 is a simplified block diagram with an enlarged exemplary patient X-ray volume scan shown on a display with a representation of the sensored hand piece and ablation probe tip displayed as well as virtual surgical guide angle markings, a virtual stop marking, and virtual target markings.

Figure 40:
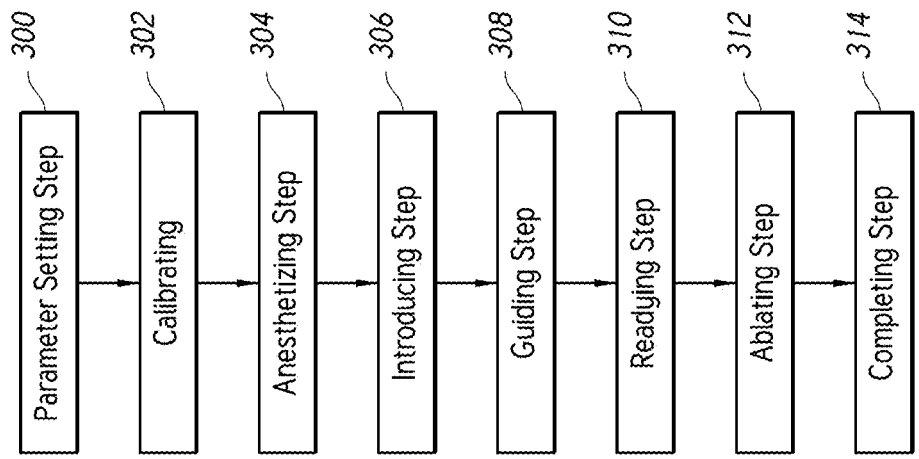

FIG. 40 is a flow chart showing exemplary steps in preferred TBA procedures using a virtual stent system including: (1) Parameter Setting; (2) Calibrating; (3) Anesthetizing; (4) Introducing; (5) Guiding; (6) Readying; (7) Ablating; and (8) Completing.

FIGS. 41-43 are side and cross-sectional views of a first exemplary ablation probe tip.

FIGS. 44-46 are perspective and cross-sectional views of a second exemplary ablation probe tip.

DETAILED DESCRIPTION OF THE INVENTION

The highly invasive surgical procedure of extracting third molars can be completely eliminated by prophylactically eliminating the small tooth buds that will eventually form the wisdom teeth. Children age 6 to 12 will generally have radiographically detectable tooth buds with no signs of tooth formation inside the tooth bud. Third molar tooth bud agenesis (the lack of third molar formation) can only be conclusively determined by age 14. Third molar tooth buds are lying just 2.0 mm to 3.0 mm beneath the surface of the attached gingival (gum) tissue, making them accessible for rapid anesthesia and minimally invasive ablation with the correct selection of soft tissue ablation and supporting scanning and stent-manufacturing technologies.

Figure 1:
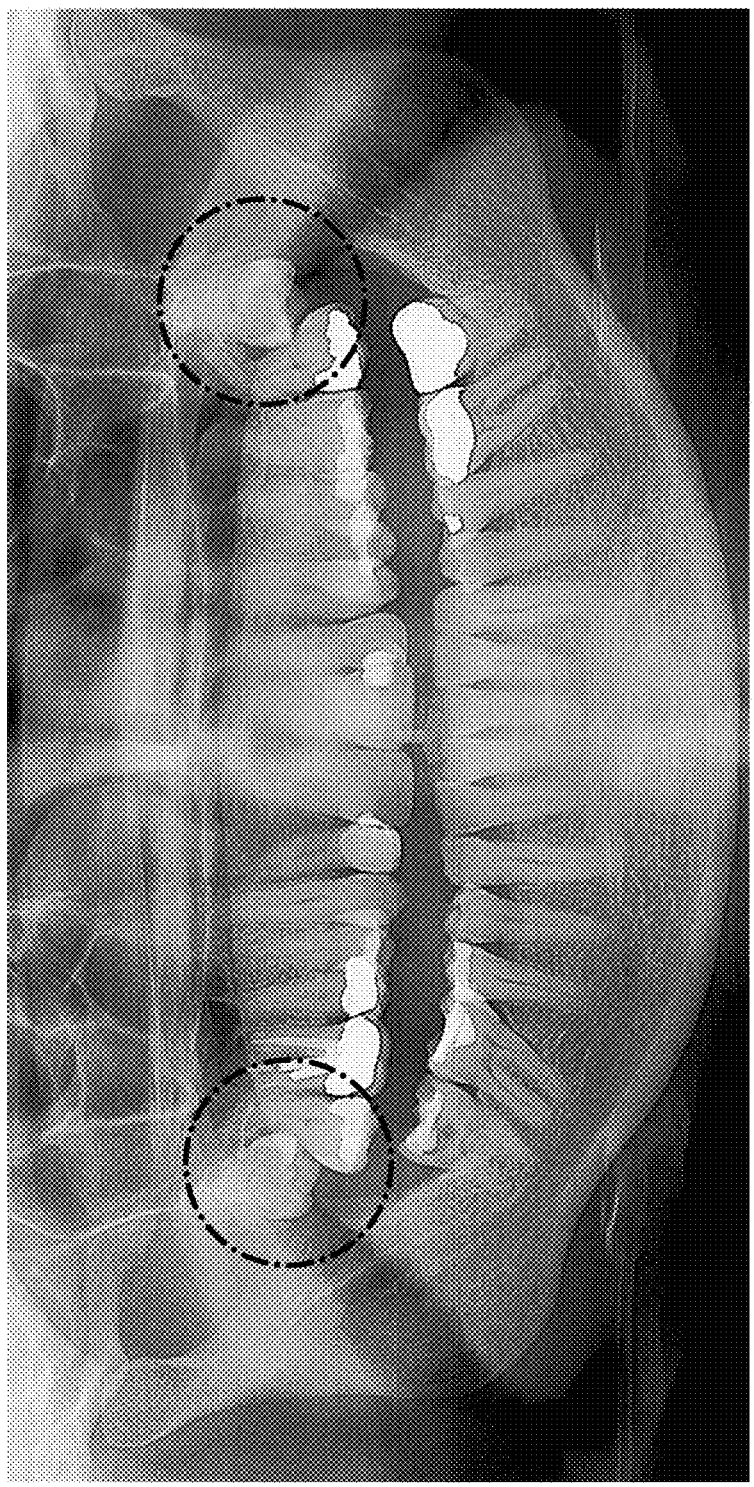
FIG. 1 is an X-ray showing a 48-year-old patient with both upper third molars present, the X-ray being presented to show examples of the range of problems that adult patients experience when they have third molars that are not extracted at an early age.
Figure 2:
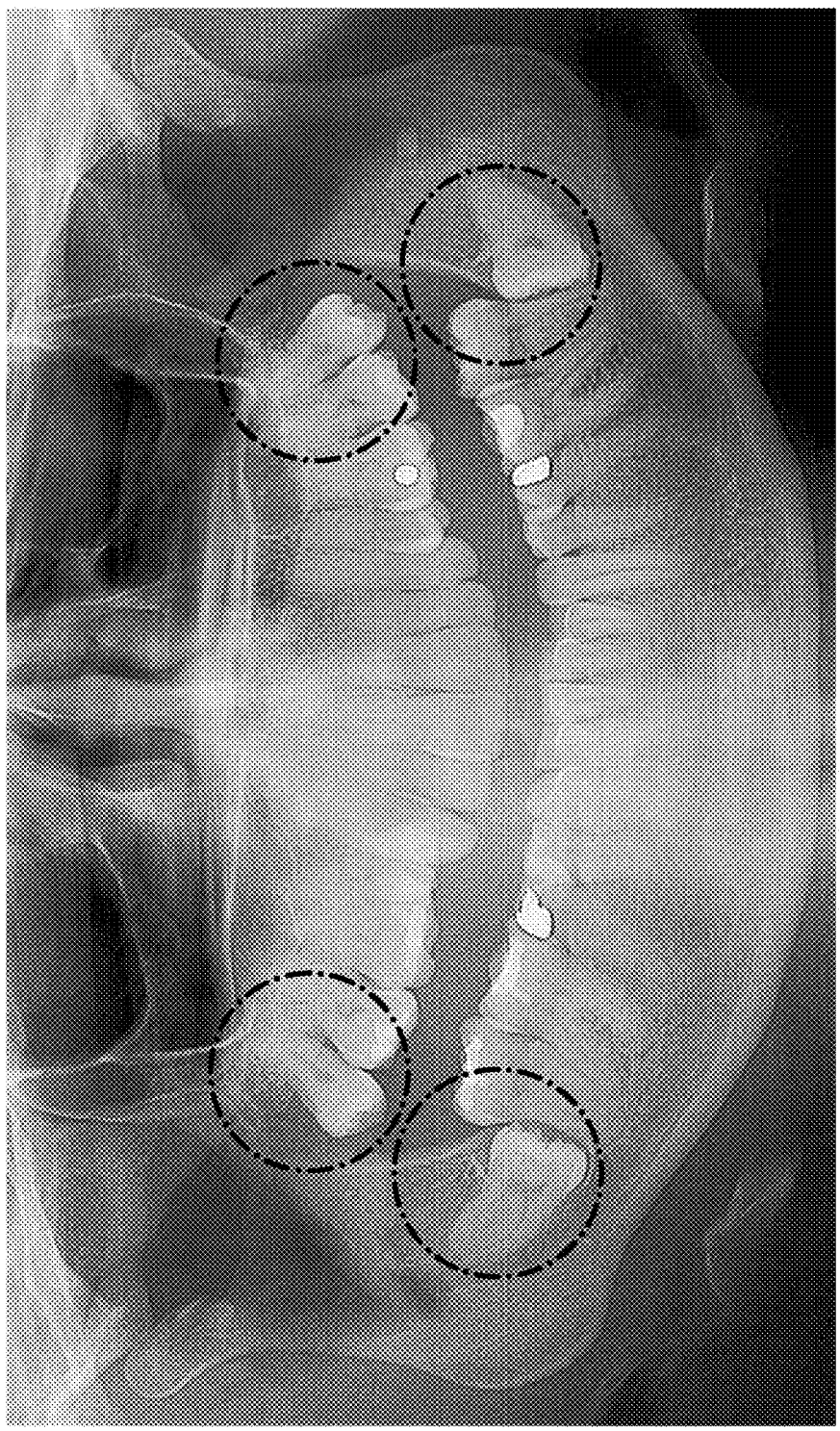
FIG. 2 is an X-ray showing a 36-year-old patient with all four third molars present, the X-ray being presented to show examples of the range of problems that adult patients experience when they have third molars that are not extracted at an early age.
Figure 3:
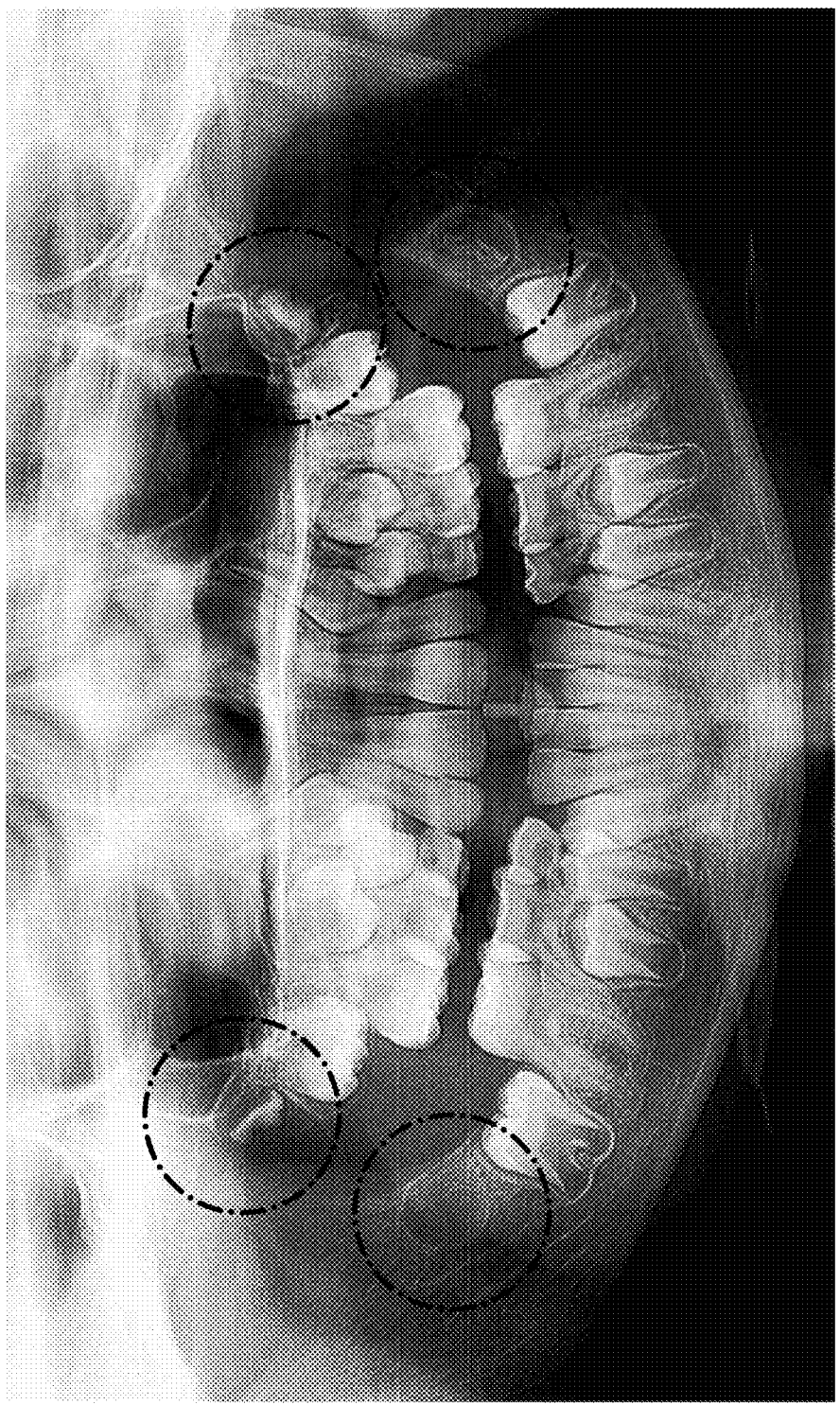
FIG. 3 is an X-ray showing a 9-year-old patient with four third molar tooth buds present; three of them are in very early stages of enamel formation, but the lower right third molar tooth bud does not yet have enamel formed.
Figure 4:
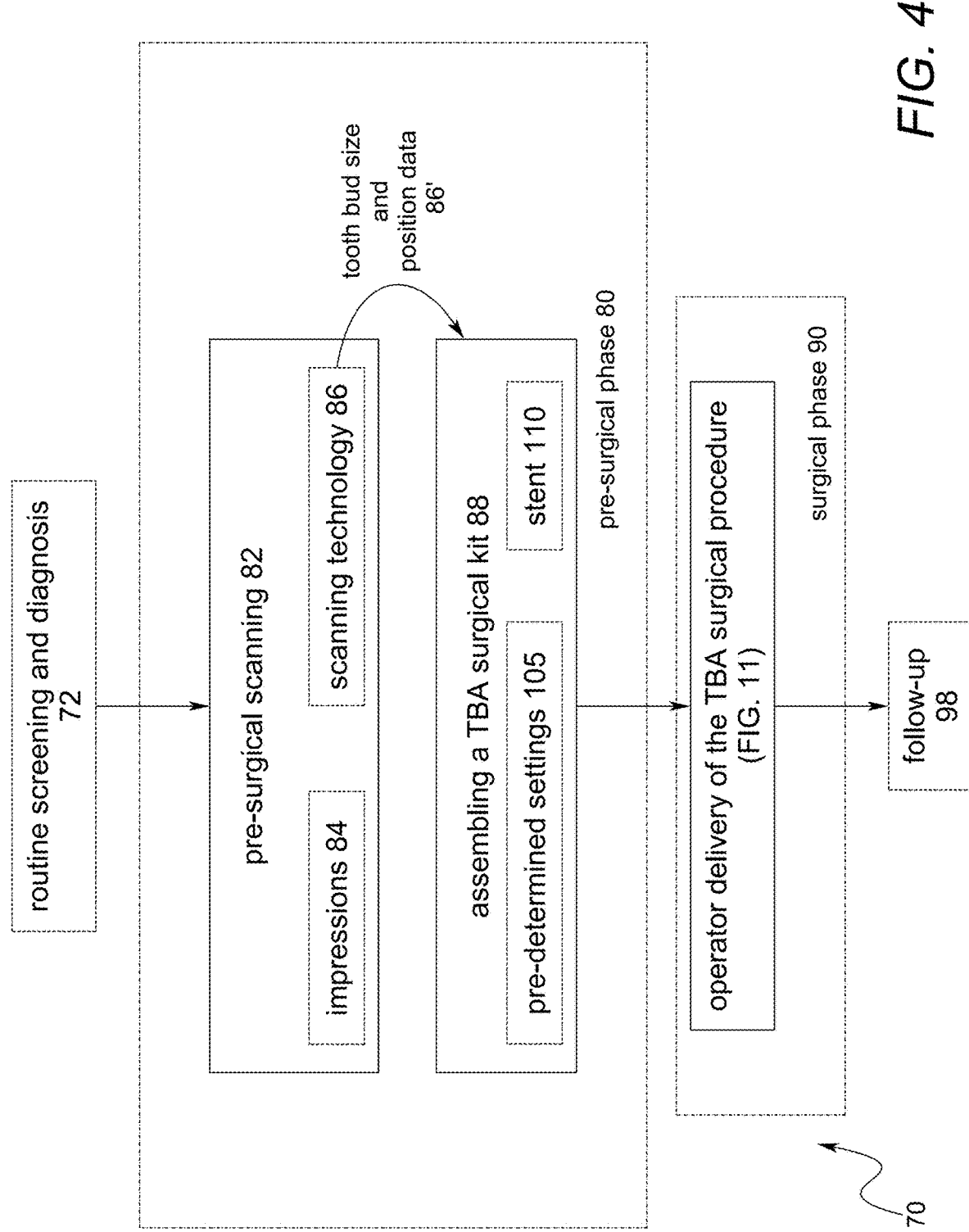
FIG. 4 is a flow chart showing steps in preferred TBA procedures including: (1) routine screening and diagnosis; (2) pre-surgical impressions and scanning; (3) assembling a TBA surgical kit; (4) operator delivery of the TBA procedure; and (5) follow-up.

By successfully improving existing medical technology, the highly invasive, painful, and complication-ridden procedure of traditional surgical removal of third molars (i.e. "wisdom teeth" extractions) can be replaced with a minimally invasive tooth bud ablation (TBA) procedure 70 such as that shown in FIG. 4 that is risk free, painless post-operatively, and less expensive when compared to surgical extractions.

The TBA procedure 70 (FIG. 4) and TBA system 100 (FIG. 5) for use in the TBA procedure 70 seek to achieve: (1) a minimally invasive procedure consisting of a surgical access path at a surgical site (e.g. at each tooth bud surgical site), (2) that can predictably ablate all four third molar tooth buds 120 in thirty (30) minutes or less (including time to administer anesthesia) using either microwave ("MW") or radio frequency ("RF") ablation, (3) that can be administered by dental practitioners under normal office conditions, (4) with direct procedure costs reduced by 25% or more, and (5) with zero risks or complications when compared to traditional surgical extraction of fully developed third molars. It should be noted that the TBA procedure 70 is shown and described as a prophylactic third molar tooth bud ablation (TMTBA), but it is not limited thereto. For example, there may be supernumerary teeth that should not be in a patient's mouth (e.g. there may be two teeth #5), the removal of which would not be prophylactic in nature.

One preferred advantage of the surgical phase 90 described herein is that it is a minimally invasive surgical procedure. With a minimally invasive surgical procedure design coupled with electronic feedback controls using MW and RF ablation technology to limit soft tissue damage, performing this procedure on children aged 6-12 years old takes approximately thirty (30) (or fewer) minutes, including the time to administer local anesthetics.

Another preferred advantage of the surgical phase 90 described herein is that it will not accidentally disrupt adjacent second molar tooth development, even though the formation of second molars are well under way because these tooth buds 120 have started to form before birth. The use of relatively new scanning technologies (e.g. computed tomography volume scanning such as cone beam computed tomography (CBCT) scanning and MRI volume scanning) and accurate custom surgical stents 110 to guide ablation probe tip 108, 148 placement will eliminate the risk of accidentally disrupting the second molars by minimizing collateral tissue damage.

Summarily, the TBA procedure 70 (FIG. 4) preferably includes a screening phase 72, a pre-surgical phase 80 (also referred to as TBA pre-surgical phase 80) that includes pre-surgical scanning 82 and the assembling of a TBA surgical kit 88 (that includes pre-determined settings 105 as well as a surgical stent 110), a surgical phase 90 (also referred to as TBA surgical phase 90), and a follow-up phase 98.

A TBA system 100 (FIG. 5) is preferably used during the surgical phase 90 (shown graphically in FIGS. 6-10 and as a flow chart in FIG. 11) of the TBA procedure 70. Summarily, the TBA system 100 includes a TBA probe system 101 (including a generator 104 capable of emitting one or more types of ablation means 104', a hand piece 106, and an ablation probe tip 108, 148) and at least one surgical stent 110 (which was manufactured or fabricated during the pre-surgical phase 80). Each stent 110 has at least one surgical guide 112 to guide the placement of the ablation probe tip 108, 148 so that its center of ablation 130a is placed into the middle of the tooth bud 130b. This is accomplished by positioning ablation probe tip 108, 148 through the surgical guide 112 at a pre-defined angle and pre-defined depth (which may be done, for example, using a mechanical relationship of the ablation probe tip 108 and the surgical guide 112 to form a "stop" therebetween or in other manners disclosed herein). FIGS. 6-10 show (and FIG. 11 describes) one procedure of inserting the ablation probe tip 108 through the surgical guide 112 of a stent 110, ablating the tooth bud 120, and removing the ablation probe tip 108 from the ablated tooth bud 120'. FIGS. 30-34 show an alternative procedure of inserting the alternative ablation probe tip 148 through a surgical guide 112 of a stent 110, ablating the tooth bud 120, and removing the ablation probe tip 108 from the ablated tooth bud 120'. FIGS. 35-39 show a sensored ablation probe tip 232 for use with a virtual stent system. FIG. 40 shows an exemplary preferred TBA procedure using a virtual stent system.

The TBA System 100

The TBA system 100 described herein is the system that is used during the surgical phase 90 of the TBA procedure 70. Some of the components (e.g. the custom surgical stent 110 and the pre-determined settings 105) used in the TBA system 100 are part of the TBA surgical kit assembled during the pre-surgical phase 80.

Figure 5:
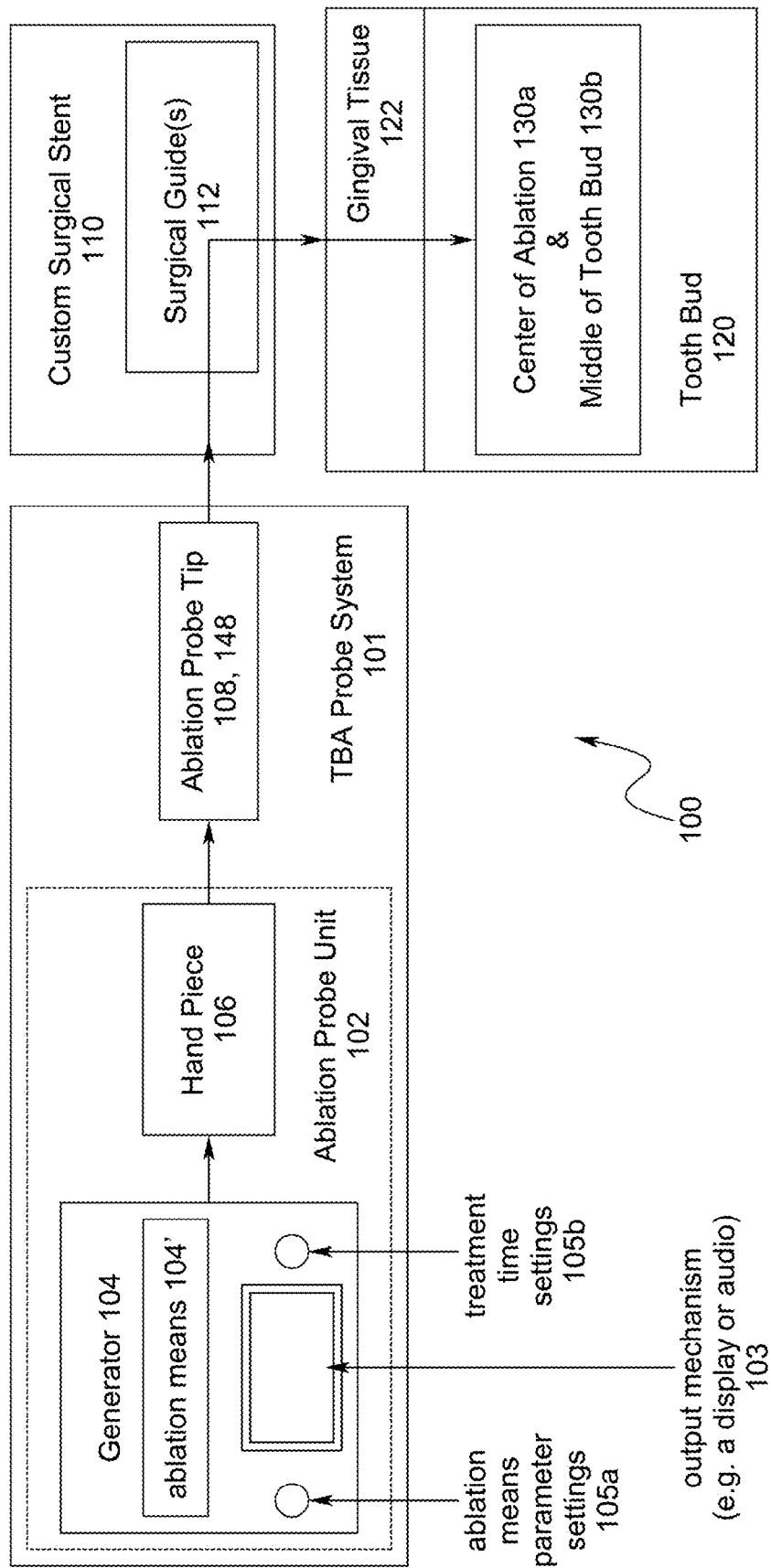
FIG. 5 is a simplified block diagram of a TBA probe system, a custom surgical stent, and a tooth bud.

The TBA system 100, as shown in FIG. 5, includes a TBA probe system 101 (including a generator 104, a hand piece 106, and an ablation probe tip 108, 148) and at least one surgical stent 110 (each stent 110 has at least one surgical guide 112 to guide (direct) the placement of the ablation probe tip 108, 148 to the middle of the tooth bud 130b). The generator 104 and the hand piece 106 may be jointly referred to as the ablation probe unit 102 (or the programmable ablation probe unit 102). The generator 104 and hand piece 106 may be integral or functionally connected together. The generator 104 (and/or the ablation probe unit 102) may be programmed with pre-determined parameter settings 105*a* and/or treatment time settings 105*b* (referred to jointly as pre-determined settings 105). The generator 104 (and/or the ablation probe unit 102) provides an ablation means 104' for ablating the tooth bud 120 based on the pre-determined settings 105. Central to the TBA system 100, is the interaction between the ablation probe tip 108, 148 and the surgical stents 110 (and specifically the surgical guides 112).

Generator 104

The generator 104 provides the ablation means 104' suitable for ablating a tooth bud 120 during the surgical phase 90 of the TBA procedure 70. MW energy and RF energy are discussed as exemplary preferred ablation means 104'. Another alternative preferred ablation means 104' is irreversible electroporation because it has subsecond activation times that can reduce collateral tissue damage. Other alternative preferred ablation means 104' include, but are not limited to, cryoablation, ultra-high intensity ultrasound, laser, chemical, thermal or hot tip (e.g. a tip having any source of heat including, but not limited to, a light bulb, a soldering iron, or steam heat), and/or mechanical means. These ablation means 104' may also be combined either simultaneously or consecutively. It should also be noted that other known and yet-to-be-developed ablation means 104' may also be used. It should be noted that although discussed primarily in terms of MW and RF, unless specifically set forth otherwise, the use of other ablation means 104' is possible.

The generator 104 (alone or as part of an ablation probe unit 102) may be programmed by the operator and/or at the laboratory and/or factory and may be accomplished automatically or manually. The programming of the generator 104 may include programming at least one pre-determined setting 105.

The following bulleted points are exemplary details and/or features that may be incorporated in preferred generators 104.

- Preferred generators 104 may be multi-use devices designed as 110V counter-top units.
- Preferred generators 104 may be MW/RF generators with output levels determined initially through finite element analysis models or experimentally derived functions that exist for tumor ablation.
- Preferred generators 104 (and/or ablation probe units 102) may have operator input mechanisms (e.g. knobs, dials, key pads, keyboards, I/O interfaces, connections to the internet, or other means for inputting or programming) in which the operator inputs (or allows input of) the pre-determined settings 105.
- Preferred generators 104 (and/or ablation probe units 102) may have output mechanisms (e.g. a display or audio) 103 for providing setting feedback (e.g. calibration cycles and pre-determined settings 105), warning feedback (e.g. to prevent operator mishandling), and intra-operative feedback on the progress of the procedure such as time remaining (e.g. a count down or a series of beeps to alert the operator to procedure completion) and/or temperature (e.g. to alert the operator to overheating).
- Preferred output displays may be digital readout displays (that may be color and/or in a large format) that permit the operator to easily see feedback intra-operatively from across a standard dental operatory (approximately 6-8 feet viewing distance).

Hand Piece 106

The hand piece 106 is the functional intermediary between the generator 104 and the ablation probe tip 108, 148. The hand piece 106 may be connected substantially at one end to the generator 104. Substantially at the other end of the hand piece 106, opposite the generator 104, the end of the hand piece 106 (the surgical end) is adapted to accept the ablation probe tip 108, 148. The hand piece 106 is preferably detachable from the generator 104 (if they are not an integral unit) and the ablation probe tip 108, 148 (having an insertion end and a connection end) is preferably detachable from the hand piece 106.

The following bulleted points are exemplary details and/or features that may be incorporated in preferred hand pieces 106.

- Preferred hand pieces 106 preferably hold or secure an ablation probe tip 108, 148 by latching the ablation probe tip 108, 148 into the hand piece head. In some hand pieces 106, the ablation probe tip 108, 148 latches into the hand piece head at an angle (e.g. a 90 degree angle). It should be noted that the terms "latching" and "latch" are used to describe any type of secure fit including, but not limited to, clipping, snapping, or holding.
- Preferred hand pieces 106 preferably have a hand piece head (attached or integral) that is at an approximately 20 degree angle to the rest of the hand piece. This bend emulates a standard dental high-speed hand piece to facilitate easy access of both upper and lower surgical sites. In some preferred hand pieces 106, the 20 degree bend can be adjusted intra-operatively to permit improved operator access to both upper and lower arches.
- Preferred hand pieces 106 preferably are rapidly detachable from the generator 104. Preferably the connectors are ultra-reliable for repeated removal/attachment from the generator 104.
- Preferred hand pieces 106 are preferably fully steam autoclavable. Alternative preferred hand pieces 106 are disposable or have disposable covers.
- Preferred hand pieces 106 preferably have actuators to allow operator activation. The actuators may be separate from the hand pieces 106 or integral therewith. Exemplary actuators include, but are not limited to, a wireless foot control or a hand-operated switch on the hand piece 106.
- The hand piece 106 may be integral with the generator 104 to form a hand-held integrated generator unit (hand-held integrated ablation probe unit).

Ablation Probe Tips 108, 148

The ablation probe tip 108, 148 has a "shaft" having a connection end and an insertion end. The connection end has structure suitable for connecting the ablation probe tip 108, 148 to the hand piece 106. The insertion end is insertable into the tooth bud 120. The ablation means 104' flows from the generator 104 through the ablation probe tip 108, 148 and out to a center of ablation 130*a* (the focal point of the ablation). The ablation probe tip 108, 148 is insertable through the surgical guide 112, through the gingival tissue 122, and into the middle of the tooth bud 130*b*. Some ablation probe tips 108 have the center of ablation 130*a* at or near the insertion end of the ablation probe tip 108 such that when the insertion end of the ablation probe tip 108 is positioned at the pre-defined angle ($\phi$) and pre-defined depth (x) during the surgical phase 90, the center of ablation 130*a* substantially coincides with or overlaps the middle of the tooth bud 130*b*. Alternative ablation probe tips 148 have the center of ablation 130*a* further from the insertion end and along the shaft of the ablation probe tip 148 such that when the center of ablation 130*a* of the ablation probe tip 148 is positioned so that the center of ablation 130*a* substantially coincides with or overlaps the middle of the tooth bud 130*b*.

The pre-defined angle (ϕ) is the angle at which the ablation probe tip's effective center of ablation 130*a* is in the "middle" of the tooth bud 130*b* as calculated (during the pre-surgical phase 80) as described herein or using an alternative method. The pre-defined depth (x) is the depth at which the ablation probe tip's effective center of ablation 130*a* is in the "middle" of the tooth bud 130*b* as calculated as described herein or using an alternative method. The phrase "middle of the tooth bud 130*b*" is meant to include the three-dimensional area within the tooth bud 120 and, in particular, the three-dimensional area within the tooth bud 120 that is more towards the absolute middle point than towards the outer periphery of the tooth. The pre-defined angle (ϕ) and pre-defined depth (x) together define a three-dimensional (including an up/down dimension (depth (x)), a front/back dimension (y), and a side/side dimension (z)) path of insertion through which the ablation probe tip 108, 148 accesses the gingival tissue 122 and the tooth bud 120 so that the center of ablation 130*a* substantially coincides with or overlaps the middle of the tooth bud 130*b*. The pre-defined angle (ϕ) and pre-defined depth (x) can also be referred to as the "calculated angle and depth," the "prescribed angle and depth," the "proper angle and depth," the "correct angle and depth," the "optimal angle and depth," or the "ideal angle and depth."

One preferred ablation probe tip 108 includes a mechanical stop structure 140 (e.g. a band, protrusion, or shoulder) designed to physically limit the depth of the ablation probe tip 108 when used in conjunction with mechanical stop structure 142 (e.g. the upper surface, a protrusion on the upper surface, or a notch in the upper surface) of the surgical stent 110 and/or surgical guide 112. In other words, the mechanical stop structure 142 of the surgical guide 112 and the mechanical stop structure 140 of the ablation probe tip 108 together limit how much of the ablation probe tip 108 can pass through the surgical guide 112 until there is a mechanical stop between the mechanical stop structure 142 of the surgical guide 112 and the mechanical stop structure 140 of the ablation probe tip 108. The physical prevention of further progression of the ablation probe tip 108 provided by the interaction of the mechanical stop structures 140, 142 is a type of "stop information," the ablation probe tip 108 being depth limited to the depth indicated by the stop information (which would be the depth at which the center of ablation 130*a* substantially coincides with or overlaps with the middle of the tooth bud 130*b*).

Each ablation probe tip 108 may be individually custom made (e.g. manufactured or fabricated) or may be selected from a family of ablation probe tips 108 (i.e. there may be a "family" of probe tips 108 that will cover all clinical possibilities for tooth bud diameters and depths). In the manufacturing or fabricating of the surgical stents 110, however, the characteristics of the ablation probe tip 108 (custom made or selected) that may be taken into consideration include, for example, length, shape, angle, position of a mechanical stop structure 140, diameter, and size, shape, and location of the center of ablation 130*a*. For example, if a particular ablation probe tip 108 had mechanical stop structure 140 (shown as the bottom surface of an annular ring or shoulder in FIGS. 6-10 and 28-29) 10.0 mm from the absolute tip of the ablation probe tip 108 (and the center of ablation 130*a* is substantially adjacent to the absolute tip), but the center of ablation 130*a* was only 8.0 mm from the surface of the gingival tissue 122 (shown as (x) in FIG. 6), then the surgical guide 112 would have to be 2.0 mm thick (shown as (y) in FIG. 6). On the other hand, if all surgical guides 112 being made by the procedure were exactly 0.5 mm thick, the ablation probe tip 108 would either have to be made or selected so that the mechanical stop structure 140 is 8.5 mm from the center of ablation 130*a* of the ablation probe tip 108. The appropriate ablation probe tip 108 preferably will result in the intra-operative placement of the effective center of ablation 130*a* of the ablation probe tip 108 into the targeted middle of the tooth bud 130*b* ±0.5 mm.

FIGS. 30-34 show an alternative ablation probe tip 148 with alternative stop structure 150 (shown as the portion of the alternative ablation probe tip 148 between the center of ablation 130*a* and the absolute tip 152). The alternative stop structure 150 may also be referred to as "extension stop structure 150." This alternative stop structure 150 uses the bottom of the gingival tissue 122 (or the top of the bone upon which the tooth bud 120 is positioned) as the limiting structure used in conjunction with the alternative stop structure 150 to position the alternative ablation probe tip 148 at the proper pre-defined depth (x). (It should be noted that the "top of the bone" may be above or below the tooth bud 120 depending on whether the tooth bud is in the lower jaw or the upper jaw.) Once the pre-defined depth (x) is calculated, the distance (y) between the center of ablation 130*a* and the bottom of the gingival tissue 122 (or the top of the bone upon which the tooth bud 120 is positioned) can be measured and/or calculated. The alternative stop structure 150 is an extension of the alternative ablation probe tip 148 from the center of ablation 130*a* and should be the same length as the distance (y). In use, an alternative ablation probe tip 148 would be inserted through the surgical guide 112 of a surgical stent 110 at the proper pre-defined angle (ϕ), but would come to a stop when the absolute tip 152 touched the bottom of the gingival tissue 122 (or the top of the bone upon which the tooth bud 120 is positioned). In this position, the center of ablation 130*a* would be the distance (y) from the bottom of the gingival tissue 122 (or the top of the bone upon which the tooth bud 120 is positioned). The effective center of ablation 130*a* targeted middle of the tooth bud 130*b* would be substantially overlapping. The physical prevention of further progression of the ablation probe tip 148 provided by the interaction absolute tip 152 touching the bottom of the gingival tissue 122 (or the top of the bone upon which the tooth bud 120 is positioned) is a type of "stop information," the ablation probe tip 148 being depth limited to the depth indicated by the stop information (which would be the depth at which the center of ablation 130*a* substantially coincides with or overlaps with the middle of the tooth bud 130*b*).

These alternative ablation probe tips 148 may also be individually custom made (e.g. manufactured or fabricated) or may be selected from a family of ablation probe tips 148 (i.e. there may be a "family" of probe tips 148 that will cover all clinical possibilities for tooth bud diameters and depths). Although the surgical stent 110 is not used for limiting structure to position the alternative ablation probe tip 148 at the proper pre-defined depth (x), it is still used to guide the alternative ablation probe tip 148 in the proper pre-defined angle (ϕ). As previously set forth, the manufacturing or fabricating of the surgical stents 110 may take into consideration the characteristics of the alternative ablation probe tip 148 (custom made or selected). The characteristics that may be taken into consideration include, for example, length, shape, angle, diameter, and position of the mechanical stop structure 150. The size, shape, and location of the center of ablation 130*a* of the alternative ablation probe tip 148 may also be taken into consideration in the manufacturing or fabricating of the surgical stents 110. The alternative ablation probe tip 148 preferably will result in the intra-operative placement of the effective center of ablation 130*a* of the alternative ablation probe tip 148 into the targeted middle of the tooth bud 130*b* ±0.5 mm.

It should be noted that for either type of ablation probe tip 108, 148, another variation would include either a movable center of ablation 130*a* or multiple centers of ablation 130*a*. A movable center of ablation 130*a* variation would mean that the actual center of ablation 130*a* could move up or down within the ablation probe tip 108, 148 for fine adjustments or for gross adjustments in position. The movability and/or position of the center of ablation 130*a* could be controlled by the operator or automatically (e.g. by a computer). For example, if the alternative ablation probe tip 148 had a movable center of ablation 130*a*, the alternative ablation probe tip 148 would be inserted through the surgical guide 112 of a surgical stent 110 at the proper pre-defined angle (φ), but would come to a stop when the absolute tip 152 touched the bottom of the gingival tissue 122 (or the top of the bone upon which the tooth bud 120 is positioned). The movable center of ablation 130*a* would be moved to the distance (y) from the absolute tip 152 such that the effective center of ablation 130*a* and the targeted middle of the tooth bud 130*b* would be substantially overlapping.

A multiple centers of ablation 130*a* variation would mean that there would be more than one center of ablation 130*a* within the ablation probe tip 108, 148. Which of the multiple centers of ablation 130*a* was used for a particular tooth bud could be controlled by the operator or automatically (e.g. by a computer). For example, if the alternative ablation probe tip 148 had multiple centers of ablation 130*a*, the alternative ablation probe tip 148 would be inserted through the surgical guide 112 of a surgical stent 110 at proper pre-defined angle (φ), but would come to a stop when the absolute tip 152 touched the bottom of the gingival tissue 122 (or the top of the bone upon which the tooth bud 120 is positioned). Which of the multiple centers of ablation 130*a* would be actuated would be determined by which center of ablation 130*a* was the closest to the distance (y) from the absolute tip 152 such that the effective center of ablation 130*a* and the targeted middle of the tooth bud 130*b* would be substantially overlapping.

The ablation probe tips 108, 148 may be sharp enough and/or may be strong enough so that the ablation probe tips 108, 148 can be "self-introducing" in that the ablation probe tips 108, 148 can be pushed through the gingival tissue 122. Alternatively, if tissue trocars 146 (described herein) are to be used, the ablation probe tips 108, 148 would not have to be as sharp and/or strong.

The following bulleted points are exemplary details and/or features that may be incorporated in preferred ablation probe tips 108, 148.

- Preferred ablation probe tips 108, 148 are preferably disposable (e.g. single-use).
- Preferred ablation probe tips 108, 148 may be specially designed to work with the specific ablation means 104' produced by the generator 104. Other preferred ablation probe tips 108, 148 may be designed to work with multiple types of ablation means 104' produced by the generator 104 or generators 104.
- The design of the ablation probe tip 108, 148 may be dependent on the physics involved with transmitting ablation means 104' through the smallest possible diameter with an ideal maximum diameter. For example, an MW/RF ablation probe tip may be designed for transmitting MW/RF energy through the smallest possible diameter with an ideal maximum diameter of 0.5 mm to 1.0 mm targeted.
- The "family" of probe tips 108, 148 may include probe tips 108, 148 having a variety of characteristics. For example, the family might have probe tips 108, 148 of different lengths ranging from 5.0 mm to 25.0 mm. This range would accommodate the various diameters of the tooth buds 120 and overlying gingival tissue 122 thicknesses.
- Intra-operative temperature sensing (shown as being performed by a linear array of temperature sensors 144 in FIG. 8) is preferably provided at or near the apex of the ablation probe tip 108, 148 (assuming placement in the ideal middle of the tooth bud 130*b*) and/or along the shaft 145 of the probe tip 108, 148. Temperature sensors 144 provide core temperatures for feedback control purposes (so that the operator can monitor the temperature and/or for software feedback control loops and emergency shutdown) and/or for safety controls to reduce or eliminate collateral tissue damage. Intra-operative tissue temperature is preferably measured, both to assure complete ablation and to prevent overheating of tissues; this may require additional set up data or programming. If temperature sensors 144 are used, the appropriate ablation probe tip 108, 148 preferably will result in the intra-operative placement of the effective center of ablation 130*a* of the ablation probe tip 108, 148 into the targeted middle of the tooth bud 130*b* ±1.0 mm.

FIGS. 41-46 show specific exemplary ablation probe tips 320, 360 (that could be constructed as ablation probe tip 108 or ablation probe tip 148) that would work in the TBA systems 100 discussed herein. Each exemplary ablation probe tip 320, 360 has a shaft with a connection end 322*a*, 362*a* (shown as a female SMA connector for connecting directly or indirectly to a generator 104 via a hand piece 106) and an insertion end 322*b*, 362*b* (for inserting into the tooth bud 120). These exemplary ablation probe tips 320, 360 have microwave ablation means (e.g. microwave energy, waves, and/or radiation) that flow from the generator 104 to and through the exemplary ablation probe tip 320, 360 (from the connection end 322*a*, 362*a* towards the insertion end 322*b*, 362*b*, and reflecting back from a reflector 326, 366) and to a center of ablation 130*a* (the focal point of the ablation) from which it radiates through the window 328, 368. The shown exemplary ablation probe tips 320, 360 preferably include "structure for transmitting microwave ablation means" 324, 364 and a reflector 326, 366. The structure for transmitting microwave ablation means 324, 364 may be a coaxial cable (coax cable) 324, 364 or other structure having an inner conductor 324*a*, 364*a* (also referred to as a center core), insulation 324*b*, 364*b* (e.g. a dielectric insulator such as polytetrafluoroethylene (PTFE)) surrounding the inner conductor, an outer conductor or shield 324*c*, 364*c* (e.g. a metallic or copper annular layer) surrounding the insulation, and an optional outer sheath, protector, or cover 324*d*, 364*d* (the outer cover is "optional" in that it may be distinct from the main "coaxial cable" so that it is added in a separate step) surrounding the outer shield. Microwave ablation means that "hit" the reflector 326, 366 bounce (reflect) back up the coax cable 324, 364 creating two "signals" (the incoming microwave ablation means and the reflected microwave ablation means). Put another way, the reflector 326, 366 creates an electrically conductive end treatment between the inner conductor 324*a*, 364a and the outer conductor or shield 324c, 364c such that the inner conductor 324a, 364a and the outer conductor or shield 324c, 364c act like reflector surfaces that redirect the microwave to create the standing wave. A 360 degree opening or window 328, 368 is positioned near the insertion end 322b, 362b (shown as approximately 2 mm from the insertion end 322b, 362b). The reflector 326, 366 allows the microwave ablation means to create a standing wave as the two signals (the incoming and reflected) interact through interference patterns and are efficiently radiated laterally (90 degrees) to the coax cable 324, 364. The center of ablation 130a is located at least substantially centered in the coax inner conductor 324a, 364a at the point where it is surrounded by the window 328, 368.

FIGS. 41-43 show first exemplary ablation probe tips 320 having a connection end 322a and an insertion end 322b. FIGS. 44-46 show a second exemplary ablation probe tip 360 having a connection end 362a and an insertion end 362b. The first and second exemplary ablation probe tips 320, 360 have many similar features. Both the first and the second exemplary ablation probe tips 320, 360 include a coax cable 364 (or structure equivalent thereto), a reflector 326, 366, and a gap window 328, 368 (shown as being approximately 1 mm). The gap window 328, 368 is created by removing (by known removal methods) a portion of the coax outer shield 324c, 364c. The coax outer shield 324d, 364d covers the coax outer shield 324c, 364c, but leaves a gap where the coax outer shield 324c, 364c has been removed. The outer cover 324d, 364d forms the point or sharp edge of the insertion end 322b, 362b. The outer cover 324d, 364d may be a molded sheath made from a polymer material having properties such as strength, hardness, injection-moldability, slipperiness, ability to hold a sharp point, and/or radiolucency (transparency to microwave energy) such as, for example, PEEK, Ultem, Nylon, and/or Polycarbonate.

As mentioned, both the first exemplary ablation probe tip 320 and the second exemplary ablation probe tip 360 include a gap window 328, 368. An air gap window has proven to be effective and economically efficient and, therefore would be suitable for either the first exemplary ablation probe tip 320 or the second exemplary ablation probe tip 360. Alternative gap windows 328, 368 could be made of any material that is sufficiently transparent to the microwave radiation and has the appropriate mechanical properties. One exemplary alternative to the air gap window is a ceramic gap window.

One difference between the first exemplary ablation probe tips 320 and the second exemplary ablation probe tip 360 is the specific shown reflector 326, 366. FIGS. 41-43 show first exemplary ablation probe tips 320 having a soldered reflector 326. FIGS. 44-46 show a second exemplary ablation probe tip 360 having a "deposited" reflector 326. A deposited reflector may have many different types of depositions resulting from deposition techniques including, but not limited to, "electroplating" techniques, "electroless" plating techniques, mechanical application of particulate techniques, "plasma deposition" techniques, "ion beam implantation" techniques, "sputter coating" techniques, "vacuum deposition" techniques, and any known or yet to be discovered technique for depositing a surface that is sufficiently electrically conductive to serve as a reflector directly to the surface of the coax cable. It should be noted that although the first exemplary ablation probe tip 320 is shown as having a soldered reflector 326, it could have a deposited reflector. Similarly, although the second exemplary ablation probe tip 360 is shown as having a deposited reflector 326, it could have a soldered reflector. Replacing expensive components (e.g. machined metal reflectors) with more economical alternatives (e.g. soldered, electroplated, or otherwise deposited reflectors) significantly reduced manufacturing time (plating being suitable to large scale automated processing) and the resulting exemplary ablation probe tips 320, 360 worked as well or better than more complicated and expensive versions.

There are also superficial differences such as the shape. For example, the first exemplary ablation probe tip 320 is straight and the second exemplary ablation probe tip 360 is angled. Another superficial difference is the presence in the second exemplary ablation probe tip 360 of an overmolded support 372 that is added to the exterior of the coax cable 364.

It should be noted that FIGS. 41-46 show specific exemplary ablation probe tips 320, 360. Dimensions and angles specified thereon (either written, measurable, or implied) are for purposes of enablement of these specific exemplary ablation probe tips. They are not meant to limit the scope of the invention. Further, specific features of two of the exemplary ablation probe tips may be used to create additional exemplary ablation probe tips. The specific materials and shapes of the exemplary ablation probe tips 320, 360 and the style/dimensions of the puncturing portion of the ablation probe tip (the insertion end 322b, 362b) may be adapted for a particular intended use without affecting the scope of the invention.

Stent 110

The at least one custom surgical stent 110 (also referred to as a "stent 110" or a "surgical stent 110") has at least one surgical guide 112 (also referred to as "guides 112" or "ablation probe tip guides 112"). Two surgical stents 110 would be used, for example, if both upper and lower tooth buds 120 were to be ablated. The surgical stents 110 are designed to seat in a patient's mouth and may be supported by at least one tooth (a tooth-supported surgical stent), soft tissue (a soft tissue-supported surgical stent), and/or bone (a bone-supported surgical stent). If the surgical stent 110 is supported by more than one of these, it could be considered a combination-supported surgical stent. Preferred surgical stents 110 may "snap" into the mechanical undercuts inherent in the patient's erupted teeth. A surgical stent 110 would have more than one surgical guide 112 if more than one tooth bud were to be ablated on either the upper or lower jaw.

The surgical stents 110 and the guides 112 therein are used to control one or both of the pre-defined angle ($\phi$) and the pre-defined depth (x) of the ablation probe tip 108, 148 in order to assure that the ablation probe tip's effective center of ablation 130a is in the middle of the tooth bud 130b ±0.5 mm. The pre-defined angle ($\phi$) is primarily controlled by the angle of the surgical guides 112 (the passageways through the stent 110). For some types of ablation probe tips 108, the pre-defined depth (x) is primarily controlled by the interaction between the mechanical stop structure 142 of the surgical stent 110 (and/or surgical guide 112) and the mechanical stop structure 140 of the ablation probe tip 108. For other types of ablation probe tips 148, the pre-defined depth (x) is primarily controlled by the interaction between the alternative stop structure 150 and the bottom of the gingival tissue 122 (or the top of the bone upon which the tooth bud 120 is positioned). The operator inserts the ablation probe tip 108, 148 at the entry angle ($\phi$) defined by the guide 112 and to the depth (x) limited by the appropriate mechanical stop structure.

The surgical guides 112 are passageways through the surgical stent (the passageways being a type of guiding structure). The pre-defined angle (ϕ) for each passageway (guide 112) is determined by the position of the middle of the tooth bud 130b. For example, if the middle of the tooth bud 130b is "slightly forward" the angle (ϕ) of the passageway (guide 112) would be "slightly forward" so that the ablation probe tip 108, 148 is angled "slightly forward" so that the center of ablation 130a is positioned substantially at the middle of the tooth bud 130b. The angle (ϕ) of the passageway is determined (e.g. calculated) by the software based upon tooth bud volumes determined in pre-surgical volume scanning 82. In addition to providing a path through which the ablation probe tip 108, 148 accesses the gingival tissue and the tooth bud, the guides 112 may also be used to provide access for administering local anesthetic and to provide access to a tissue trocar 146 (if necessary).

In the shown preferred example, the mechanical stop structure 142 is the upper surface of the surgical stent 110 and/or surgical guide 112. The mechanical stop structure 142 is substantially adjacent to or near the surgical guide 112. The mechanical stop structure 142, however, could be positioned at locations of the surgical stent 110 beyond the surgical guide 112. Alternative preferred mechanical stop structure 142 includes a protrusion on the upper surface or a notch in the upper surface. The size and shape of the mechanical stop structure 142 is determined (calculated or designed) by a process that may be implemented as software or as a program and is based upon tooth bud volumes determined in pre-surgical volume scanning 82 as well as the length between the ablation probe tip mechanical stop structure 140 and its center of ablation 130a. For example, if the middle of the tooth bud 130b is 2.5 mm below the surface (determined in pre-surgical volume scanning 82), and the available ablation probe tips 108 have a length (between their respective mechanical stop structure 140 and its center of ablation 130a) of 2.4 mm and 2.6 mm, the process (that may be implemented by software or a program) would determine that the 2.6 mm ablation probe tip 108 is the appropriate ablation probe tip 108 (the 2.4 mm ablation probe tip 108 being too short), but that the surgical stent 110 and/or surgical guide 112 would have to be approximately 0.1 mm thick to make up the difference or the 2.6 mm ablation probe tip 108 would be able to be pushed in too far.

Figure 12:
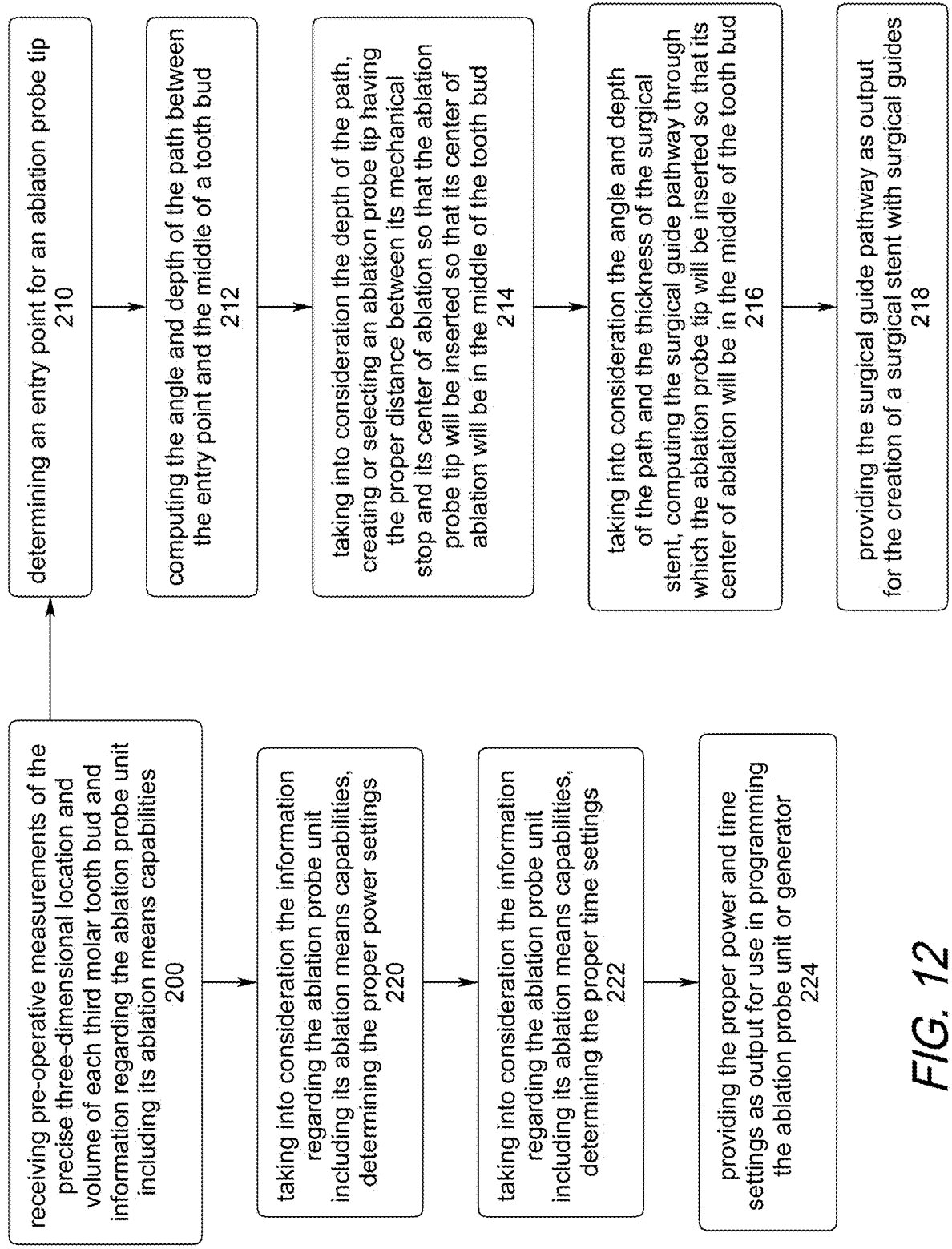
FIG. 12 is a flowchart showing the steps that a software program for manufacturing or fabricating custom surgical stents and defining (and/or computing or calculating) the pre-determined parameter settings and/or treatment time settings.

FIG. 12 is a flowchart showing the steps of a process (that may be implemented as one or more software programs or subprograms if the shown steps are divided) that, in part, determines the pre-defined angle (ϕ) and the pre-defined depth (x) (see steps 200, 210, 212, 214, 216, and 218). Using this process, patient volume scans are used to accurately manufacture or fabricate custom surgical stents 110 with the correct ablation probe tip angle (ϕ) and depth (x) manufactured into them. More specifically, using this process with the volume scans will permit accurate placement of the distal surgical guides 112 onto the custom surgical stents 110 so that both angle (ϕ) of insertion and depth (x) of insertion of the ablation probe tip 108, 148 are controlled to ±0.5 mm, placing the ablation probe tip's effective center of ablation 130a in the middle of the tooth bud 130b.

The following bulleted points are exemplary details and/or features that may be incorporated in preferred stents 110.
- Preferred surgical stents 110 are preferably disposable (e.g. single-use).
- Manufacturing or fabricating of the custom surgical stents 110 may be based upon physical (e.g. Poly Vinyl Siloxane (PVS)) full arch impressions of the patient's erupted teeth using either conventional lab fabrication techniques or direct-digital manufacturing (including digital impressions) or fabricating techniques. If an operator has a CBCT unit in his office, it may be possible to directly scan the physical (PVS) impressions and email the volume scan of the impression to eliminate the need to physically send them to the lab. The impression materials may include materials other than PVS and preferably will be contrast-optimized through the addition of X-ray contrast agents (such as barium or iodine) to provide optimized volume scans of the dental impression for resolving the fine surface detail of the teeth and gingival tissue 122. This unique material would be a radiographic contrast-optimized dental impression material for high resolution X-ray CT volume scanning. An alternative method for volume scanning replaces the physical impression with a digital impression.
- Preferred surgical stents 110 are preferably made of any appropriate material including, but not limited to, plastic, acrylic, or other nontoxic sturdy material suitable for use in a patient's mouth. One exemplary surgical stent 110 composition may be, for example, clear acrylic (polymethyl methacrylate). It should be noted that materials suitable for additive-type manufacturing (or other direct-digital manufacturing or fabricating techniques) that resulted in nontoxic sturdy stents would be preferable.
- Preferred surgical stents 110 preferably have markings such as color codes or numbering clearly marking or identifying the tooth bud numbering sites.
- Once the surgical stent 110 is seated onto the patient's teeth, it preferably will remain firmly in place throughout the surgical phase 90 of the TBA procedure 70.
- The operator may administer local anesthetic through the guides 112.

Pre-Determined Settings 105

The pre-determined settings 105 include, for example, pre-determined parameter settings 105a and/or treatment time settings 105b that are needed to control (provide instructions to) the generator 104 (alone or as part of an ablation probe unit 102) to provide sufficient ablation means 104' to ablate the tooth bud 120, but not so much as to incur significant collateral soft tissue damage (e.g. to the gingival tissue 122). For example, the pre-determined parameter settings 105a might control the quantity and quality ablation means 104' delivered to the tooth bud 120. The actual pre-determined parameter settings 105a will be highly dependent on the type of ablation means 104' to be delivered. For example, MW and RF ablation means might have parameters relating to wavelength and/or frequency, hot tip ablation means might have parameters relating to temperature, chemical ablation means might have parameters relating to the strength of the chemical and how fast the chemical is flowing into the tooth bud, and mechanical ablation means might have parameters relating to speed.

The pre-determined settings 105 are determined (which includes computing, calculating, looking up, processing, or otherwise determining) by a process (that may be implemented as software or a program) based upon tooth bud volumes determined in pre-surgical volume scanning 82. It should be noted that the pre-determined settings 105 may take into consideration factors other than tooth bud volume including, but not limited to, image recognition programs to measure tooth bud location, age and size of the patient, and other relevant factors to successfully image the patient for the TBA procedure 70. FIG. 12 is a flowchart showing the steps of a process (that may be implemented as one or more software programs or subprograms if the shown steps are divided) that, in part, determine the pre-determined parameter settings 105a and/or treatment time settings 105b (see steps 200, 220, 222, and 224).

The generator 104 (and/or the ablation probe unit 102) may be programmed by the operator and/or technicians at the laboratory and/or factory. The programming may be automatic or manual. "Programming" includes having the pre-determined settings 105 pre-entered and/or entering (inputting) the pre-determined settings 105 manually or automatically into the generator 104 (and/or the ablation probe unit 102) via operator input mechanisms. For example, the pre-determined settings 105 may be preprogrammed into an ablation probe unit 102, transmitted to the operator in the form of a programming signal (e.g. over the internet to be downloaded and installed in the ablation probe unit 102 or the generator 104), provided in the form of computer-readable media (e.g. a disc or a solid state USB drive), and/or provided as data (or a code) that may be manually entered into the ablation probe unit 102 (or the generator 104). Ideally, whichever method of entering/programming the ablation probe unit 102 (or the generator 104) is used, operator error is considered and eliminated as much as possible and appropriate checks are used. Preprogramming and some of the other means for programming the ablation probe unit 102 (or the generator 104) with the pre-determined settings would help to eliminate operator input errors. Another example of means for eliminating errors is that even if the ablation probe unit 102 (or the generator 104) is preprogrammed by the laboratory, the pre-determined settings might be displayed to the operator for independent "verification" as the operator could notice variations from normal pre-determined settings (e.g. the literature provided might provide a range and the operator would notice if the provided pre-determined settings 105 fell outside of the range). Yet another example is that the pre-determined settings might be provided as a code that, when input, would only function if it corresponded with a logical setting (e.g. if the person's age was also input into the ablation probe unit 102 and the code was not a logical setting based on the age, the ablation probe unit 102 would not function).

The pre-determined settings 105 for each TBA site may be included in the TBA surgical kit as a print out, on a disk or other computer readable storage media, or with instructions on how to obtain or download the information.

The pre-determined ablation means parameter settings 105a can also be referred to as "parameter settings 105a," "preferred parameter settings 105a," "optimal parameter settings 105a," "ideal parameter settings 105a," "pre-determined parameter settings 105a," "recommended parameter settings 105a," or "prescribed parameter settings 105a."

Tissue Trocar 146

If the ablation probe tip 108, 148 is not self-introducing, at least one sharp instrument (that is preferably disposable) such as a tissue trocar 146 (and sometimes a plurality of tissue trocars) may be used by the operator to introduce (initially create) the access opening through the thick attached gingival tissue 122 that overlays third molar tooth buds 120. The tissue trocar tips are preferably sharp enough to be pushed and/or punched through the gingival tissue 122 into the base of the tooth bud. The diameter of the tissue trocar 146 rapidly increases up to 100% of the size of the ablation probe tip 108, 148. After the tissue trocar 146 has created the access opening, the tissue trocar 146 is removed and the ablation probe tip 108, 148 is immediately placed into the access opening.

TBA Surgical Kit

The TBA surgical kit is a package that includes the majority of the necessary components and information for the surgical phase 90 of the TBA procedure 70. The TBA kit will be assembled (or the assembly will be completed) based on the patient's impressions and volume scans. Preferably the TBA surgical kit has attractive packaging.

An exemplary TBA surgical kit may consist of (a) a custom surgical stent 110 for each arch as required, (b) at least one ablation probe tip 108, 148 labeled its respective surgical site, (c) at least one tissue trocar 146 (if necessary), and (d) pre-determined settings 105 for each TBA site along with patient and operator identification.

If feedback controls are a part of the ablation probe tip design, then the correct in situ tissue temperature settings are preferably computed and supplied with the ablation probe tips 108, 148 as part of the surgical kit.

The generator 104 and/or the hand pieces 106 are standard equipment in a dental office and/or can be purchased separately.

The ablation probe tips 108, 148 may be pre-purchased (or extras may be kept in a practitioner's office) in which case the TBA surgical kit would provide a part number or other identifying information so that the practitioner would know which ablation probe tip 108, 148 should be used with each guide 112.

It should be noted some of the components may not be part of the physical TBA surgical kit. For example the pre-determined settings 105 may be provided electronically.

The TBA Procedure 70

Using the TBA procedure 70 described herein, the effective center of ablation 130a of the ablation probe tip 108, 148 can be positioned at a pre-defined angle ($\phi$) and pre-defined depth (x) so that the ablation probe tip's effective center of ablation 130a is positioned substantially in the "middle" of the tooth bud 130b within approximately 50%, 25%, or even less than 10% of the average diameter of the tooth bud 120. This is extremely accurate as compared to previous procedures.

Figure 11:
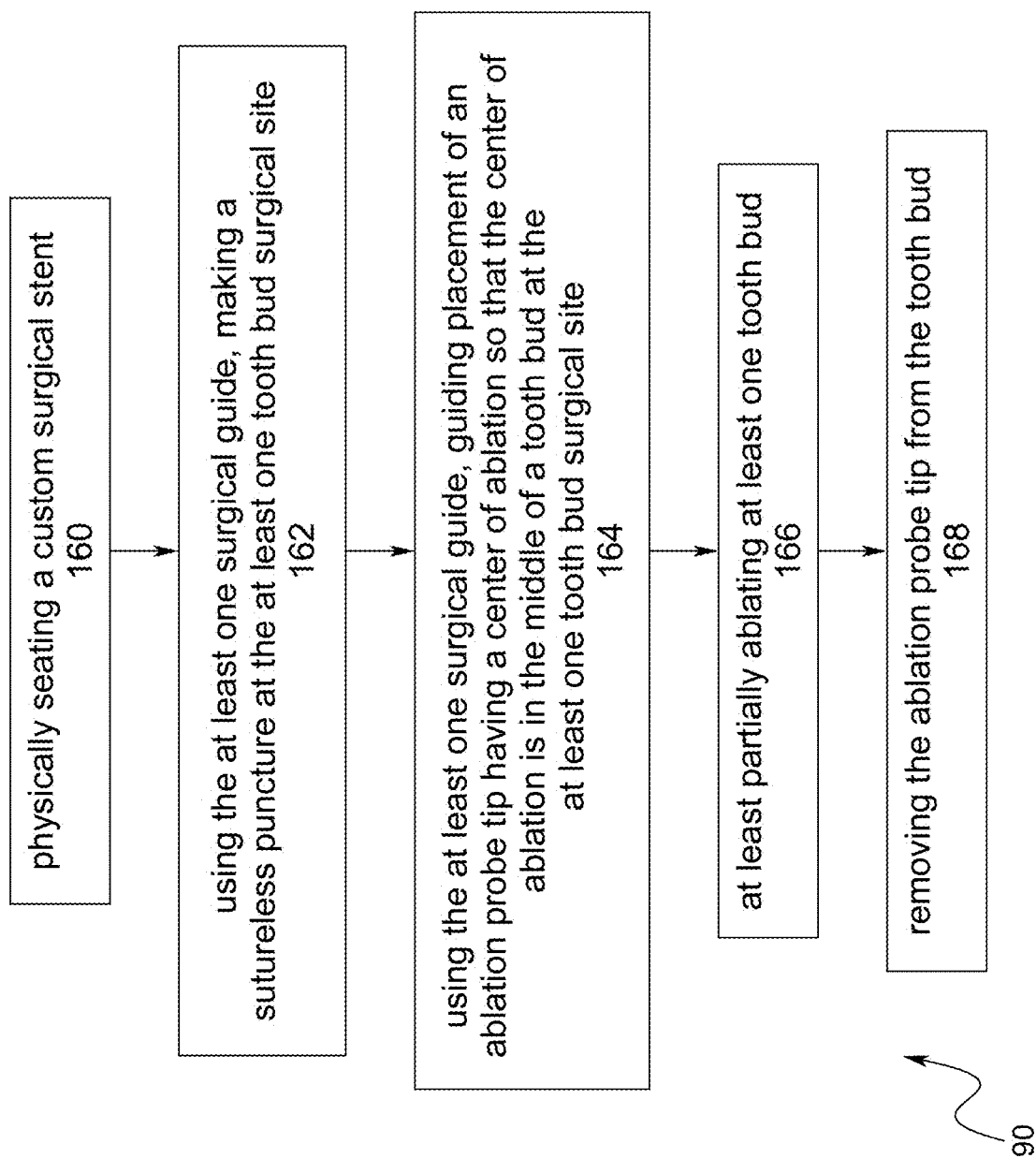
FIG. 11 is a flow chart showing the steps of a TBA procedure that results in tooth agenesis.

FIG. 4 shows the steps and/or phases in an exemplary preferred TBA procedure 70: (1) routine screening and diagnosis 72; (2) pre-surgical scanning 82 (including taking impressions 84 and using scanning technology 86); (3) assembling a TBA surgical kit 88 (including pre-determined settings 105 and a stent 110); (4) operator delivery of the surgical phase 90 of the TBA procedure 70 (shown in more detail in FIG. 11); and (5) post-surgical steps (follow-up) 98. Steps (2) and (3) are also referred to jointly as the pre-surgical phase 80 during which steps are taken to create (including calculating, manufacturing, fabricating, selecting, and/or assembling) components of the TBA system 100 and/or the TBA surgical kit to be provided to the operator. Step (4) is also referred to as the surgical phase 90 of the TBA procedure 70 during which the steps shown in FIG. 11 are taken to ablate tooth buds 120.

(1) Screening Phase 72

Routine screening using panographic or intra-oral X-ray imaging techniques is necessary to identify the presence of forming tooth buds 120 starting at age 6 through age 12 because of the wide range of ages involved with the formation of third molar tooth buds 120.

(2) Impressions and Scanning of Pre-Surgical Phase 80

Once third molar tooth buds 120 have been identified to be present using standard screening methods (screening phase 72), the next step is to pre-operatively measure the precise three-dimensional location and volume of each third molar tooth bud 120. As will be discussed, the pre-surgical phase 80, includes both impressions and scanning. The impressions 84 may be physical impressions, digital (virtual) impressions, and/or any other impressions known or yet to be discovered. The scanning technology 86 used may be any of the scanning technology discussed herein and/or any scanning technology known or yet to be discovered. Further, multiple types of technologies may be used in combination.

One practical way to accomplish the pre-operative measurement of the precise three-dimensional location and volume of each third molar tooth bud 120 is to use scanning technology 86 (e.g. computed tomography volume scanning such as dental cone beam computed tomography (CBCT)). Scanning technology 86 can be used to accurately generate the necessary three-dimensional volume scans (computed tomography volume scans) and measurements ±0.2 mm using, for example, the distal side of erupted first molars as durable physical landmarks (although it is possible to use soft tissue over bone as landmarks). The scanning technology 86 produces tooth bud size and position data 86' (also referred to as "volume scans" and/or "measurements ") that is provided for the step of producing the TBA surgical kit 88. The tooth bud size and position data 86' may be provided as a scanning technology file that can be any data file generated by the scanning technology 86 with the data necessary to manufacture or fabricate a stent 110. One exemplary type of scanning technology file is a three-dimensional computer aided design (CAD) file.

To accomplish the pre-operative measurement, an impression 84 (that can also be used for making a model for creating the stent 110) is used. A physical impression 84 of the patient's teeth and gum tissue (gingival tissue 122) is made using traditional or standard impression materials such as polyvinyl siloxane (PVS)-type or alginate-type impression material (although other impression materials can be used) that use a chemical-basis for physically obtaining a dental impression of a patient. The impressions 84 are then processed and/or scanned using scanning technology (e.g. CBCT imaging by dentists and/or CT imaging in the laboratory), and the resulting volume scan of the impression is emailed (or otherwise transmitted or delivered) to a laboratory and/or factory where the volume scan is used for manufacturing or fabricating. It is still possible to physically mail the PVS dental impressions 84 to the designated laboratory and/or factory for manufacturing or fabricating.

Although the scanning technology is discussed primarily in terms of computed tomography volume scanning (e.g. cone beam computed tomography (CBCT) technology), alternative scanning technologies including, but not limited to, ultrasound scanning technologies and future developed scanning technologies are included in the scope of the invention. Specialty software or programs may be used with the scanning technology 86 to accomplish the purpose described herein. It should be noted that alternative scanning technology 86 (including future developed scanning technology) may be used if it is able to accurately generate the necessary three-dimensional volume scans and measurements ±0.2 mm using the distal side of erupted first molars (or other landmarks) as durable physical landmarks. It should be noted that alternative scanning technology (including future developed scanning technology) may also be used as long as two- or three-dimensional scanning results in the positioning of the effective center of ablation 130a within approximately 50%, 25%, or even less than 10% of the average diameter of the tooth bud 120.

At this pre-surgical phase 80, scanning may be performed for the purpose of obtaining "digital" impressions instead of traditional physical impressions. In other words, for purposes of this disclosure, digital impressions 84 should be considered to be an alternative to physical impressions 84 and the term "impressions," unless modified by "digital" or "physical" (or variations thereof) should be considered to include both digital and/or physical impressions. Digital impressions do not necessarily use actual impression material, but instead scan the oral surfaces—including hard tooth structures and soft tissues such as gum tissue and the mucosal tissue overlying the immediate structure of the tooth bud. Digital impressions (like physical impressions) may be used to fabricate a physical and/or virtual surgical guide or stent. Using digital impressions has exemplary advantages such as improving accuracy and/or eliminating the need to physically mail (or post) the physical dental impressions.

Digital impressions may be taken using digital imaging systems such as "confocal" imaging systems (e.g. iOC and iTero intra-oral imaging systems), three-dimensional surface imaging (e.g. 3M's True Definition unit), and other digital imaging systems known and yet to be discovered. U.S. Pat. No. 7,787,132 to Korner et al., U.S. Pat. No. 7,819,591 to Rohaly et al., U.S. Pat. No. 7,990,548 to Babayoff et al., U.S. Pat. No. 8,310,683 to Babayoff et al., and U.S. Pat. No. 8,363,228 to Babayoff et al. disclose exemplary imaging systems or technology related to imaging systems that may be used in this impressions and scanning of the pre-surgical phase 80. These references are hereby incorporated by reference in their entirety. For purposes of this disclosure, these systems may be considered to be part of the scanning technology 86. These systems may be used instead of or in conjunction with the previously discussed scanning technology (e.g. the CBCT technology).

Using digital imaging systems to take digital impressions may include using a digital "wand" that is inserted into the patient's mouth and the surfaces directly scanned. Alternatively, digital imaging systems may be used to take digital impressions 84 using conventional plaster impressions (plaster models) that are digitally scanned. Dedicated laboratory scanning systems to scan plaster models use yet other technologies such as video or laser-based scanning.

(3) Assembling a TBA Surgical Kit 88

The pre-surgical phase 80 of the TBA procedure 70 includes assembling a TBA surgical kit 88. This step of assembling a TBA surgical kit 88 preferably includes computing pre-determined settings 105 and manufacturing or fabricating the stent 110 based on tooth bud size and position data 86' obtained from the scanning technology 86. The process of computing pre-determined settings 105 may be controlled by a process (that may be implemented by software or a program). The process of manufacturing or fabricating the stent 110 may also be controlled by a process (that may be implemented by software or a program).

After the impressions 84 are processed and/or scanned and the tooth bud size and position data 86' is obtained, the process of manufacturing or fabricating the stent 110 may be carried out using direct-digital manufacturing or fabricating techniques similar to the processes used for manufacturing or fabricating implant surgical stents directly from CBCT scans (e.g. the processes used for fabricating SurgiGuide™ and other implant surgical guides) and the process used for manufacturing or fabricating orthodontic aligners (e.g. orthodontic aligners made by Align Technology or ClearCorrect). The direct-digital manufacturing or fabricating techniques, however, use the tooth bud size and position data 86' to position and angle the surgical guides 112 on the distal aspects of the surgical stents 110 and use the erupted first molars as the primary landmark for positioning. Although manufacturing or fabricating will usually be done remotely in a laboratory and/or factory, it is possible that larger clinics will have the ability to manufacture or fabricate surgical stents 110 in their own in-house laboratory and/or factory.

Direct-digital manufacturing or fabricating techniques can be defined as any manufacturing or fabricating process that creates physical parts directly from data (e.g. three-dimensional CAD files) using manufacturing or fabricating techniques including, but not limited to, surgical stent manufacturing or fabricating technologies, rapid turn-around fabrication technologies, computer aided manufacturing (CAM), technologies using computer aided design (CAD), computer numerical control (CNC) milling, "additive" manufacturing, direct-digital laser stereolithography fabrication, "three-dimensional printing," or any other manufacturing or fabricating means known or yet to be discovered that is capable of using the results generated by scanning to manufacture or fabricate the custom surgical stents. Because of the possibility for the integrated use of direct-digital volume scanning of impressions, low manufacturing costs, and rapid turn around times, use of direct-digital manufacturing or fabricating techniques is one preferred manufacturing or fabricating technique, but more traditional manufacturing or fabricating techniques that require more labor intensive manual laboratory processing could also be used.

At least one process that may be implemented as software or as at least one program (e.g. custom software enhancements in the CBCT software) will preferably assist in the direct-digital manufacturing or fabricating of the surgical stents 110 and define (and/or compute or calculate) the pre-determined settings 105. This process would include defining (and/or computing or calculating) positioning and entry angle data required for placement of the ablation probe tip's effective center of ablation 130*a* into the middle of the targeted tooth bud 120. Additionally, tooth bud volumes are preferably computed (possibly using the scanning technology) and then the tooth bud volumes are used to determine the pre-determined settings 105 necessary to effect therapeutic ablation. Tooth bud volumes will generally range from 4.0 mm to 12.0 mm in diameter at ages 6-12. The ablation means 104' and treatment times are preferably considered in the calculations. Companies that make CBCT imaging equipment promote the development of procedure-specific software in order to gain end-user acceptance of their imaging systems in the market place. The process may use calculations and/or look-up charts (e.g. based on experimental data) for determining the necessary settings.

FIG. 12 is a flowchart showing the steps of a process (that may be implemented as one or more software programs or subprograms if the shown steps are divided) for manufacturing or fabricating custom surgical stents 110 and/or determining the pre-determined parameter settings 105*a* and/or treatment time settings 105*b*. As shown, the process begins with receiving pre-operative measurements of the precise three-dimensional location and volume of each third molar tooth bud and information regarding the ablation probe unit including its ablation means capabilities 200. To make the stents 110, the process would preferably include the following steps: determining an entry point for an ablation probe tip 210; computing the angle and depth of the path (including the three-dimensional path of insertion) between the entry point and the middle of a tooth bud 212; taking into consideration the depth of the path, creating or selecting an ablation probe tip having the proper distance between its mechanical stop and its center of ablation so that the ablation probe tip will be inserted so that its center of ablation will be in the middle of the tooth bud 214; taking into consideration the angle and depth of the path and the thickness of the surgical stent, computing the surgical guide pathway (including the three-dimensional path of insertion) through which the ablation probe tip will be inserted so that its center of ablation will be in the middle of the tooth bud 216; and providing the surgical guide pathway as output for the creation of a surgical stent with surgical guides 218. To calculate the pre-determined parameter settings 105*a* and/or treatment time settings 105*b*, the process would preferably include the following steps: taking into consideration the information regarding the ablation probe unit including its ablation means capabilities, determining the proper power settings 220; taking into consideration the information regarding the ablation probe unit including its ablation means capabilities, determining the proper time settings 222; and providing the proper power and time settings as output for use in programming the ablation probe unit or generator 224.

As described above, in addition to the surgical stent(s) 110 and the pre-determined settings 105, the TBA surgical kit may include at least one ablation probe tip 108, 148 labeled for its respective surgical site, at least one tissue trocar 146 (if necessary), and patient and operator identification.

The TBA surgical kit is provided to the operator.

(4) Surgical Phase 90

FIGS. 6-10 show graphically, and FIG. 11 shows as a flow chart, the surgical phase 90 of the TBA procedure. The surgical phase 90 may be performed by a dental operator (dental practitioner) in his office (e.g. a pediatric and/or general dental office) under normal office conditions. At this point, the generator 104 has been programmed with the pre-determined settings 105 and normal surgical procedures have been followed. The generator 104 is preferably tuned so that the ablation means 104' is set to ablate the small, substantially spherical ablation volumes of third molar tooth buds 120 in order to minimize (or possibly eliminate) collateral osseous and soft tissue damage, especially damage to adjacent second molars that are likely not yet erupted. Further, the surgical phase 90 uses single-use and disposable delivery systems that use components designed for intra-oral use.

Summarily, as shown in FIG. 11, the first step is physically seating a surgical stent 160 in a patient's mouth. Next, the operator makes an access path at the at least one tooth bud surgical site 162. The operator also places the ablation probe tip so that the center of ablation is in the middle of a tooth bud at the at least one tooth bud surgical site (using the custom surgical stent to guide the placement) 164. It should be noted that if the ablation probe tip is "self-introducing," the step of making an access path and the step of placing the ablation probe tip may occur simultaneously. Then, the at least one tooth bud is at least partially ablated 166 and the ablation probe tip is removed from the tooth bud 168. These and other exemplary steps are detailed in the following paragraphs.

The operator preferably starts the surgical phase 90 by placing the surgical stent 110 into place onto the patient's teeth prior to administering local anesthetic to the surgical site. The local anesthetic will then be administered through the surgical stent 110 and guides 112 that are in close approximation with the gingival tissue 122, thus reducing the amount of anesthetic necessary because of the precise placement of anesthetic agent. Achieving local anesthesia in this procedure will be easier than anesthetizing lower permanent molar teeth for routine fillings since only soft tissues, which will be 8.0 mm to 15.0 mm deep, are involved.

The step of physically seating a surgical stent 110 may also include physically seating the surgical stent in a patient's mouth, physically seating the surgical stent on a patient's erupted teeth, physically seating the surgical stent on at least one tooth in a patient's mouth, physically seating the surgical stent on a patient's soft tissue, physically seating the surgical stent on a patient's bone, or a combination of the above steps (e.g. physically seating the surgical stent on a patient's teeth, soft tissue, and bone).

Once the custom surgical stent 110 is in place and the patient is fully anesthetized, the operator then mechanically gains access to the tooth bud 120 through the stent surgical guides 112 by creating (introducing) a small surgical access path opening through the gingival tissue 122 approximately 0.1 mm to 2.0 mm (and more particularly 0.5 mm to 1.0 mm) in diameter using tissue trocars. If the ablation probe tips 108, 148 are designed to be strong enough and sharp enough to act as "self-introducing" probe tips, they can be used to introduce the surgical access path. On the other hand, if the ablation probe tip itself is not self-introducing, the surgical access path may be introduced using known techniques then there will be no need for separate tissue trocar 146.

It should be noted that the surgical access path is preferably an incision, a puncture, or a hole through the gingival tissue 122. If a self-introducing probe tip is used, the surgical access path has substantially the same diameter as the ablation probe tip 108, 148. If the probe tip is not self-introducing, the surgical access path may be a sutureless puncture (0.1 mm to 2.0 mm in diameter) or, more particularly, a sutureless puncture (0.5 mm to 1.0 mm in diameter). Alternatively, a trocar "punch" may be made through tough gingival tissue 122. Regardless of the procedure used to introduce the surgical access path, using a surgical access path to gain access or allow placement of the ablation probe tips 108, 148 to the tooth bud 120 does not kill, damage, or otherwise cause necrosis to the surrounding soft tissues (e.g. gingival tissues 122). This can be compared to other processes such as coring, boring, cutting, electrosurge ablating, or other invasive procedures that kill, damage, and/or otherwise cause necrosis to the soft tissue to which the invasive procedure has been applied. Although the preferred procedures for introducing the surgical access path might kill individual cells, the soft tissue (the gingival tissue 122) does not become necrosed because the tissue is a collection of cells that can heal itself.

Figure 7:
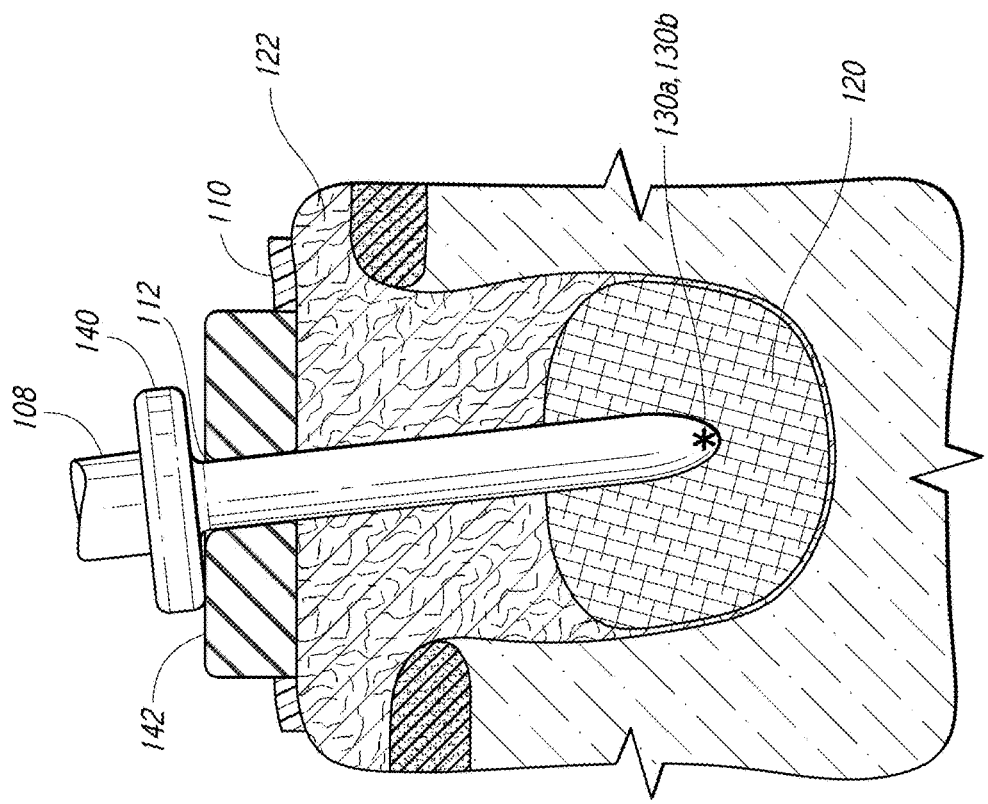
FIG. 7 is a cross-sectional side view of an ablation probe tip inserted through a surgical guide of a stent into the tooth bud.
Figure 6:
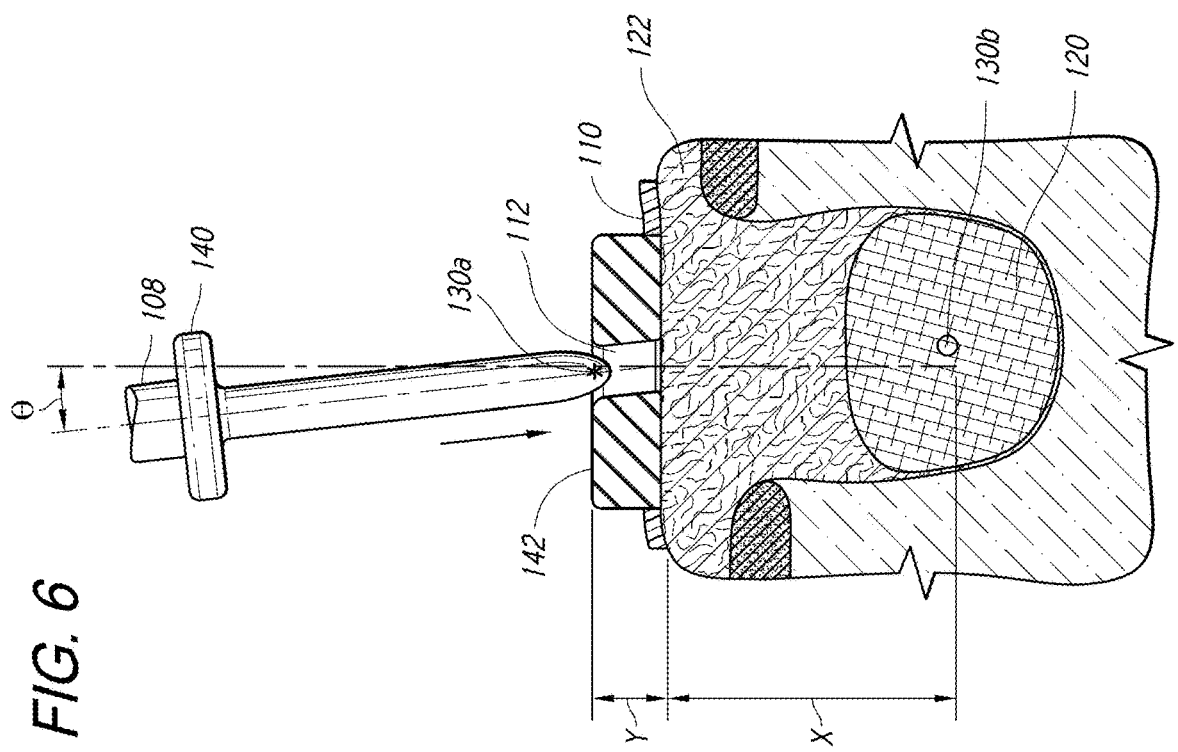
FIG. 6 is a cross-sectional side view of an ablation probe tip in the process of being inserted through a surgical guide of a stent.

As shown in FIGS. 6 and 7, the next step in the surgical phase 90 is to insert the designated ablation probe tip 108, 148 through the surgical stent 110 and into the tooth bud space until it is mechanically "stopped" in order to position the probe to the prescribed depth (which would be the pre-defined depth). The surgical stent 110 and/or its surgical guides 112 are used to control the angle (ϕ) and/or depth (x) of the ablation probe tip 108, 148 so that the effective center of ablation 130a of the ablation probe tip is in the middle of the tooth bud 130b. It should be noted that the effective center of ablation 130a for any given ablation technology does not necessarily correspond with the tip of the ablation probe. For instance, microwave ablation probes have windows or slots that may be 0.5 mm to 2.0 mm from the tip depending on the frequency of the wavelength used. Cryoablation probes have their center of ablation roughly in the middle of the probe, depending on the design and refrigerant used. A mechanical stop structure 140 on the ablation probe tip 108 preferably seats firmly onto the mechanical stop structure 142 of the surgical stent guide 112 to prevent over extension of the ablation probe tip 108. Alternatively, the mechanical stop structure 150 on the ablation probe tip 148 may be used to prevent over extension of the ablation probe tip 108.

FIG. 8 shows embedded temperature sensors 144 (or other types of feedback control mechanisms) that may be used during the ablation process. An independent feedback process using the temperature sensors 144 is preferable for this clinical procedure. Use of temperature sensors 144 along with monitoring probe impedance characteristics and percentage of reflected energy in RF/MW circuits will provide "go/no go" output for the clinician. Control algorithms are preferably used to accelerate initial ablation means 104' input followed by lower-level temperature maintenance for a defined period of time with independent confirmation that results in a fast process while simultaneously assuring complete tooth bud ablation.

FIG. 9 shows the actual ablation process. Activation of the ablation probe unit 102 to perform the ablation process is executed according to the pre-determined settings 105. Activation of the ablation probe unit 102 causes the generator 104 to provide the ablation means 104' that passes through the hand piece 106 and the ablation probe tip 108, 148 and into the tooth bud 120. This step of at least partially ablating the tooth bud is preferably accomplished without ablating any surrounding gingival tissue (although a minimal amount of surrounding gingival tissue may be ablated as an accidental byproduct of the step). This can also be thought of as the activation of the ablation probe unit 102 creating a zone of ablation that resides predominantly or completely within the tooth bud 120. The temperature sensors 144 (feedback control mechanisms) assure successful delivery of adequate ablation means 104' to ablate the tooth bud 120 while minimizing damage to adjacent osseous and soft tissues by, for example, eliminating over-heating. Given the small tissue volumes involved for pediatric patients, activation using an RF ablation means 104' would have an ablation time that is preferably less than three (3) minutes and activation using an MW ablation means 104' would have an ablation time that is preferably less than thirty (30) seconds.

Figure 10:
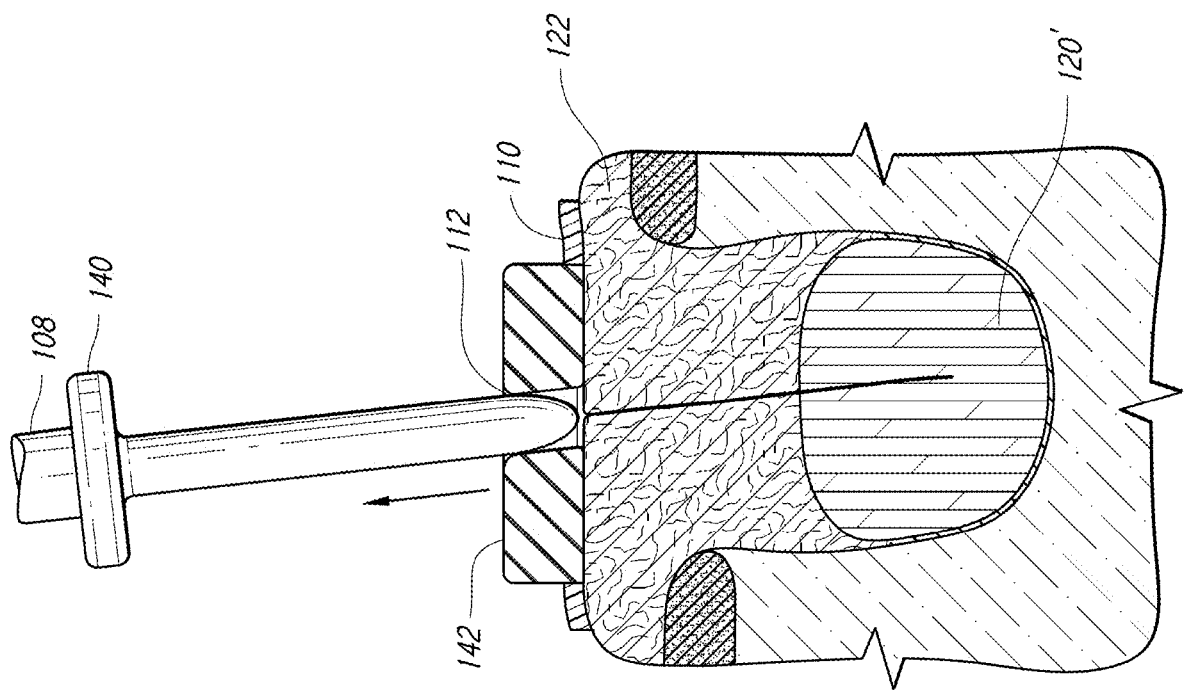
FIG. 10 is a cross-sectional side view of an ablation probe tip being removed from the ablated tooth bud.
Figure 34:
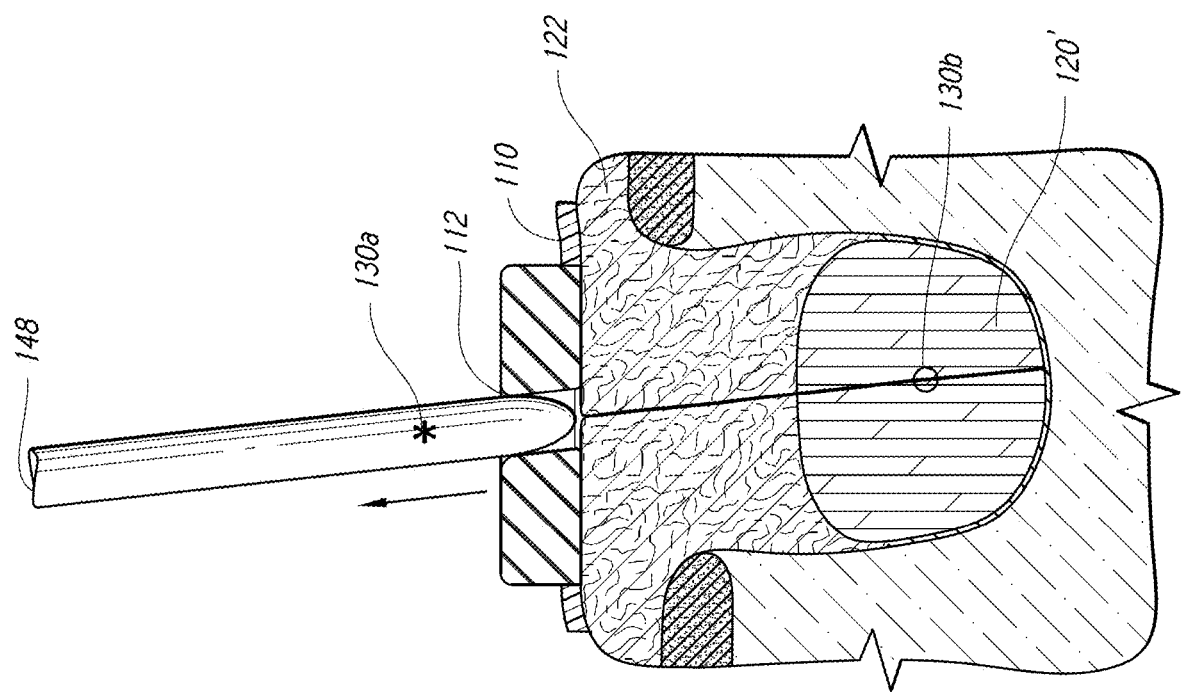
FIG. 34 is a cross-sectional side view of an alternative ablation probe tip being removed from the ablated tooth bud.

FIGS. 10 and 34 show the ablation probe tips 108, 148 being removed from the now ablated tooth bud 120'. As shown in these figures, any access path created by the procedure rapidly closes.

(5) Post-Surgical Phase 98:

After the surgical phase 90, the patient may have follow-up including, but not limited to, post-surgical instructions and, if necessary follow-up care and screening.

Post-surgical instructions that may be given to parents include the following: kids can go out and play immediately unless they were sedated, no post-surgical pain medication is necessary, bleeding (if any) will be gone in minutes, and post-surgical X-ray screening may be necessary at patient's next routine 6-month hygiene cleaning appointment to verify full ablation.

Simulated TBA Procedure 70

The following paragraphs, along with FIGS. 13-29, detail an exemplary simulated TBA procedure 70 including routine screening and diagnosis 72, the pre-surgical phase 80, and the surgical phase 90. (The structure of FIGS. 30-34 would be used in a similar manner making adjustments as suggested herein.) In several of these figures, a patient's mouth 124 (with gums 122 and teeth 126) is shown that looks like a stone model, but it should be understood that unless otherwise specified the shown mouth 124 would be a live patient's mouth.

Figure 13:
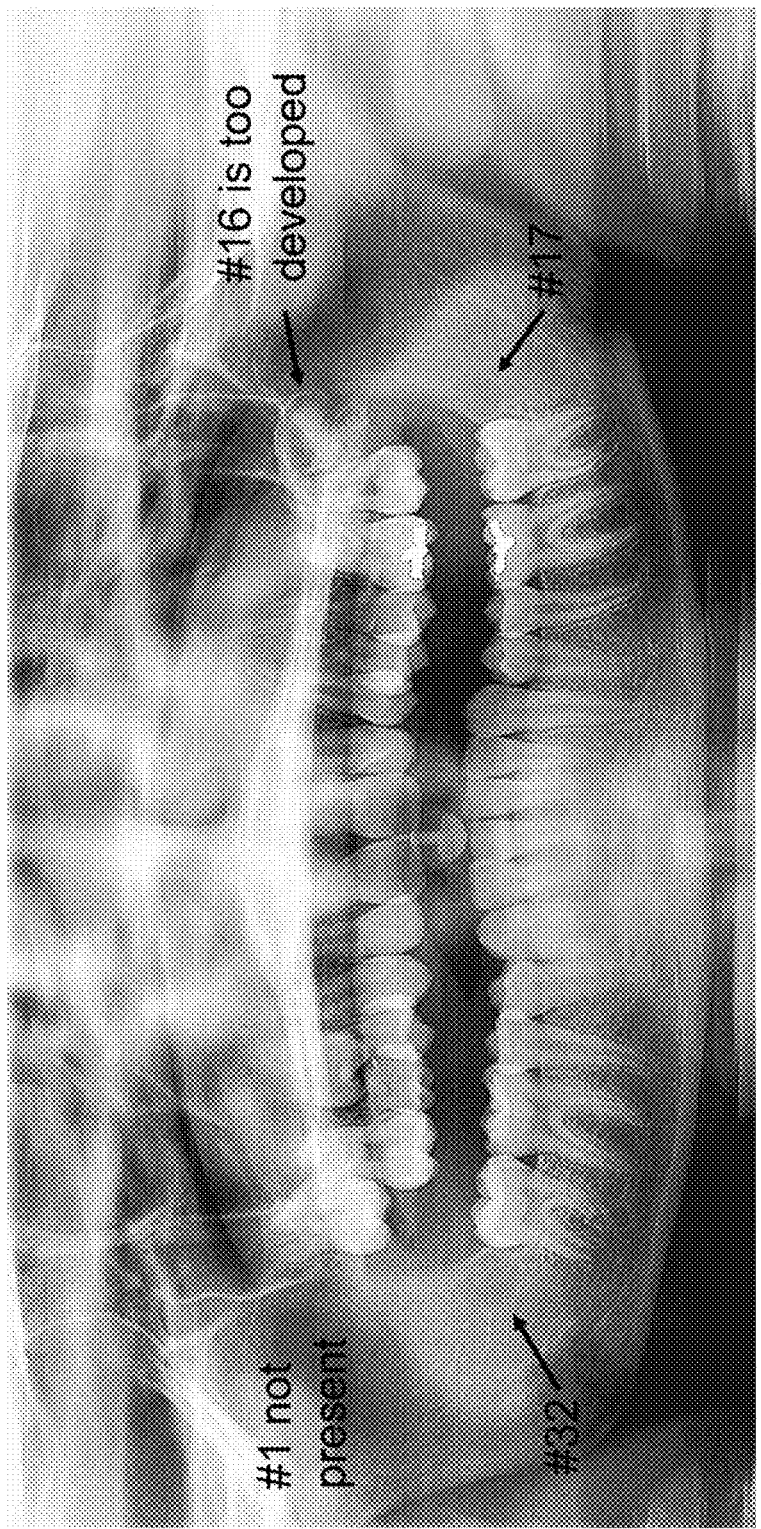
FIG. 13 is a panographic X-ray showing a patient whose third molar tooth buds in the #17 and #32 positions are treatable by TBA.
Figure 14:
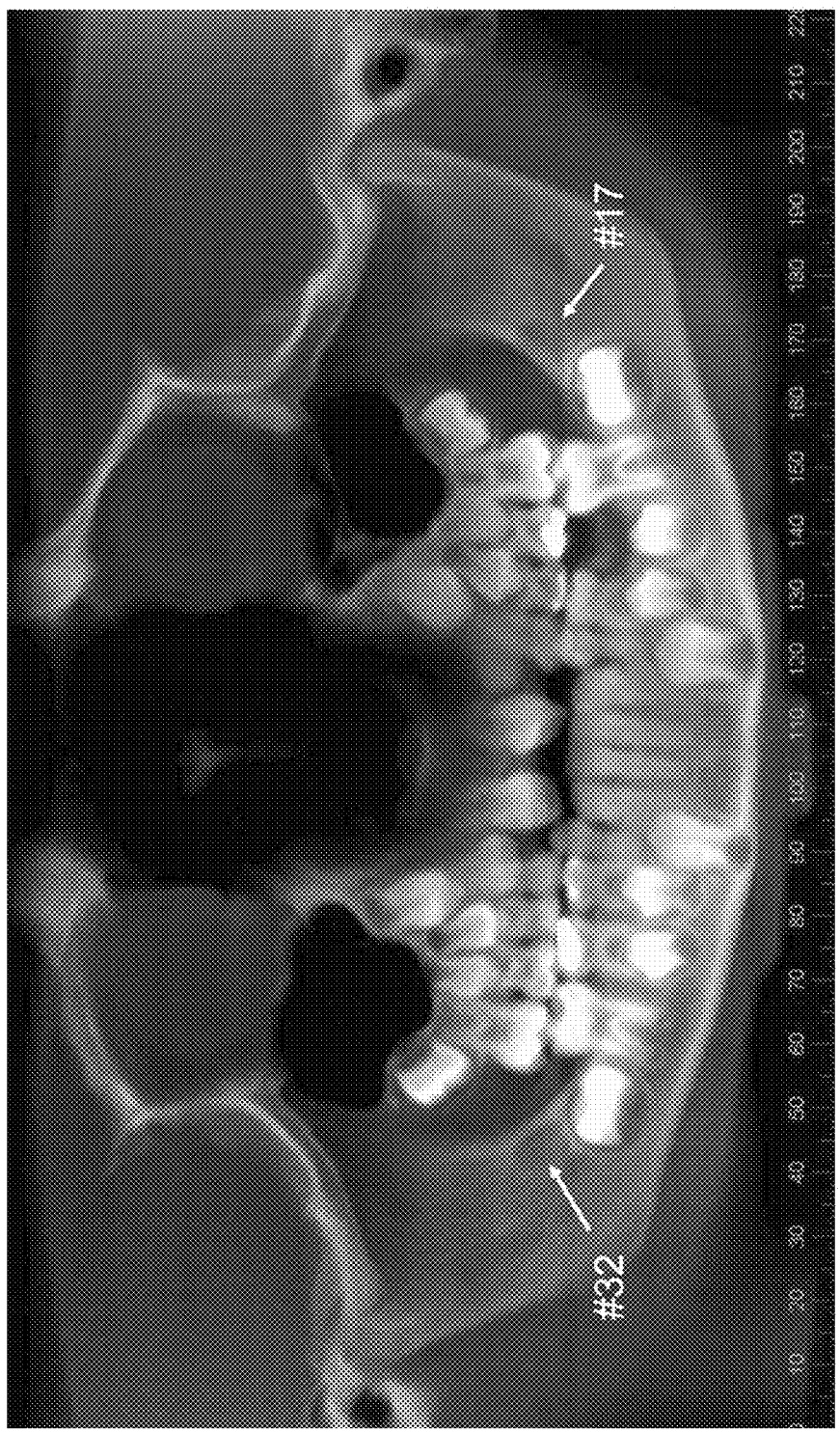
FIG. 14 is a pre-operative cone beam computed tomography ("CBCT") scan of a different patient.
Figure 15:
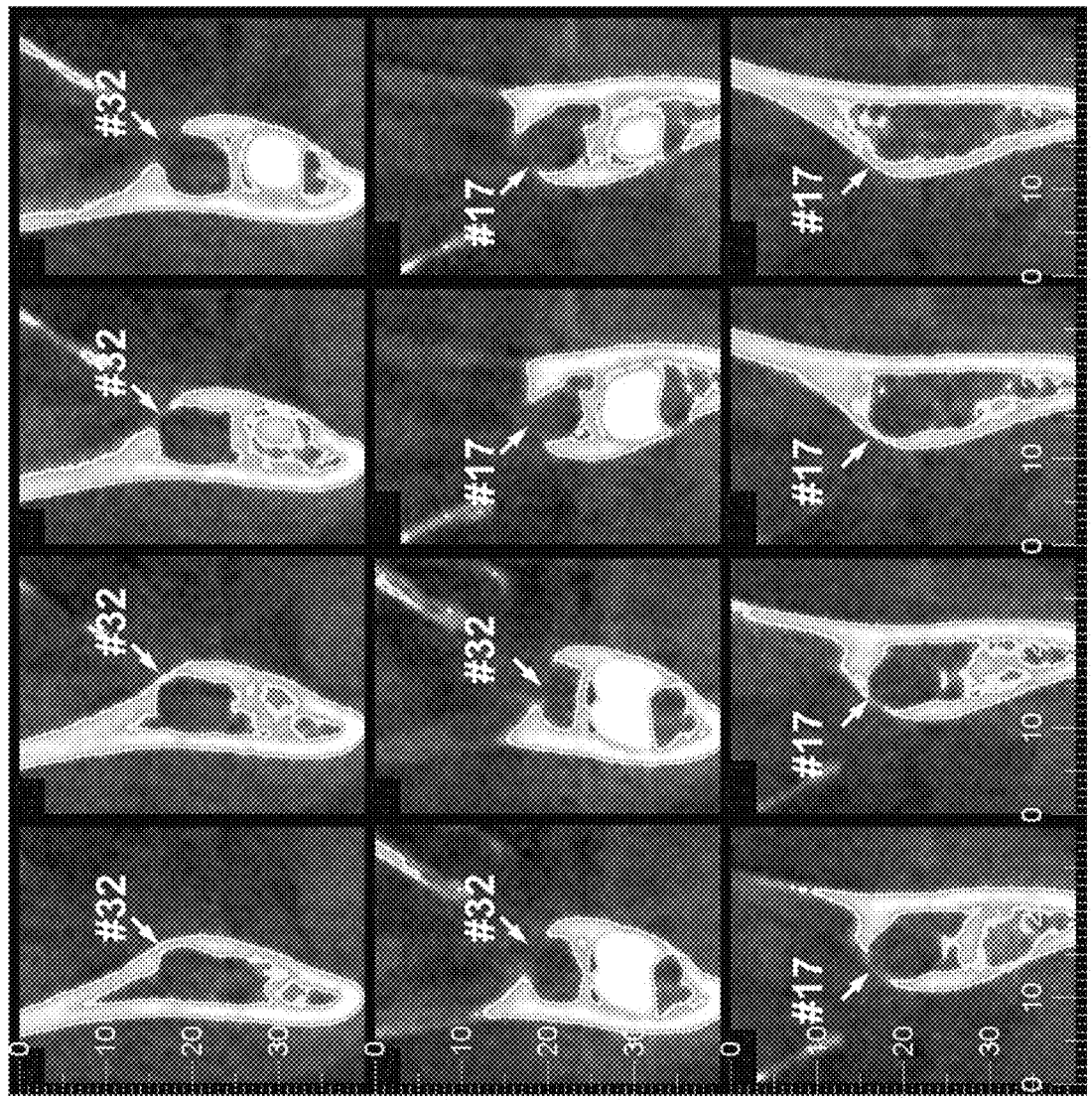
FIG. 15 is a series of X-rays showing successive 1.0 mm slices through both #17 and #32 in 1.0 mm increments.

As shown in FIG. 4, the TBA procedure begins with routine screening and diagnosis 72. FIG. 13 is a panographic X-ray showing a patient whose third molar tooth buds 120 in the #17 & #32 positions are treatable by a TBA procedure 70. FIG. 14 is a pre-operative cone beam computed tomography ("CBCT") scan (although other types of volume scanning could be used) of a patient. In a real procedure, the volume scan would be taken of the specific patient on which the TBA procedure 70 is being performed. This CBCT "reconstructed" panographic scan has a 1.0 mm scale along its bottom edge. FIG. 15 is a series of CBCT volume scan cross-sections showing successive 1.0 mm slices through both #17 and #32 in 1.0 mm increments. Each X-ray corresponds to 1.0 mm locations along the scale of FIG. 14. The left-side scale is 1.0 mm vertically. The maximum tooth bud diameters are measured to be 8.0-9.0 mm.

For purposes of describing this exemplary simulated TBA procedure 70, the use of a physical impression 84 is described in connection with FIGS. 16-19. It should be noted that an alternative exemplary TBA procedure 70 could use a virtual impression 84.

Figure 17:
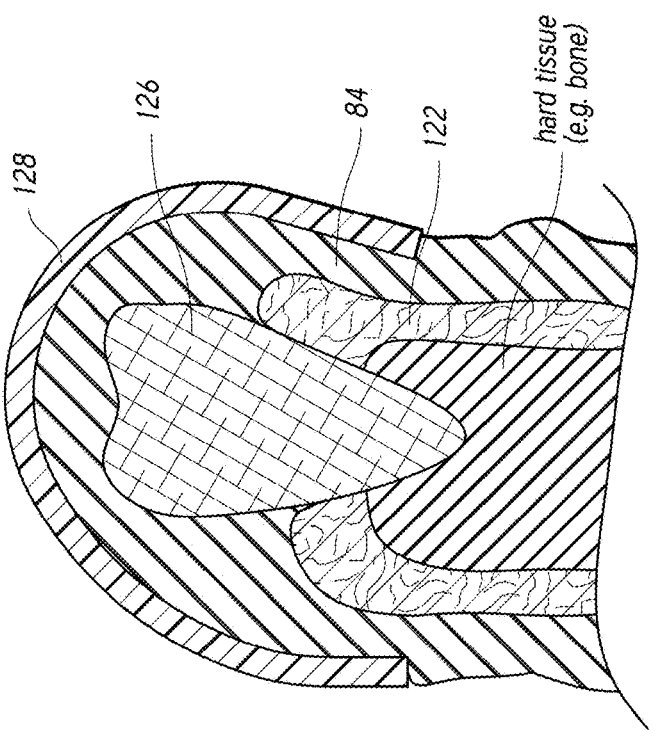
FIG. 17 is a cross-sectional view of an upper-arch impression being taken of a simulated patient.
Figure 16:
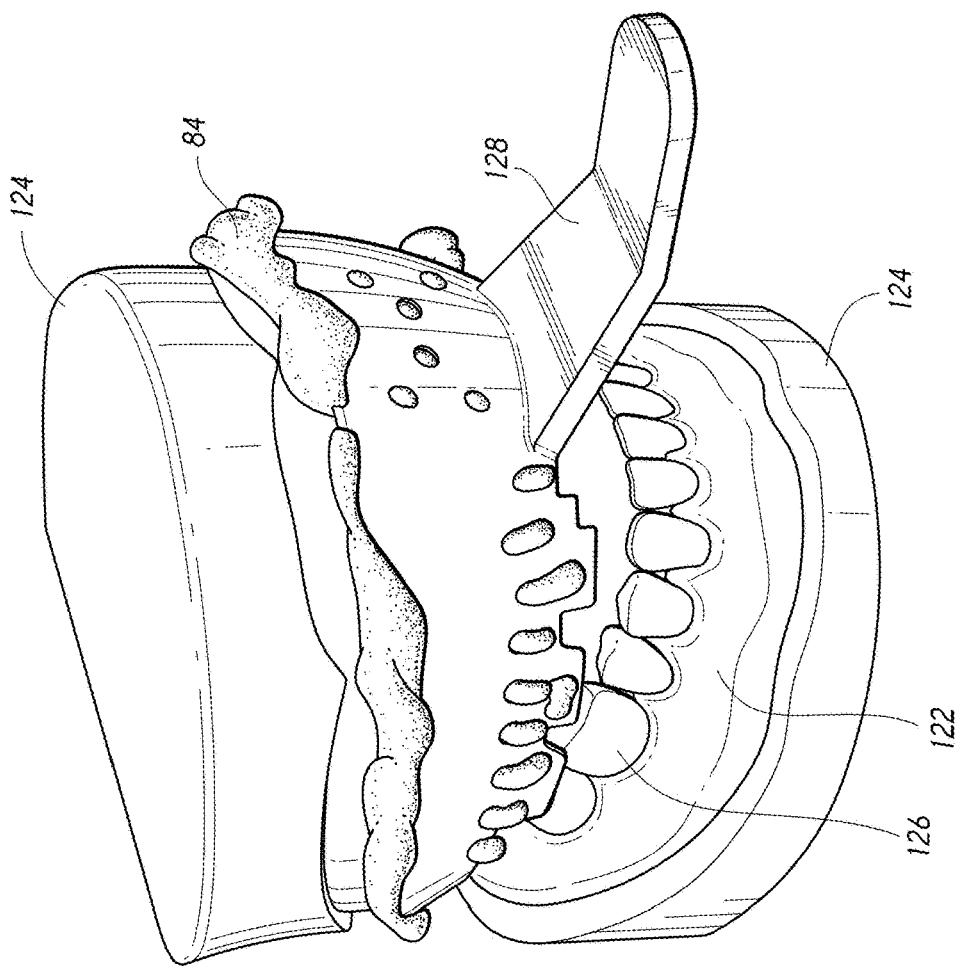
FIG. 16 is a perspective view from a front corner showing a pre-operative upper-arch impression being taken of a simulated patient.
Figure 18:
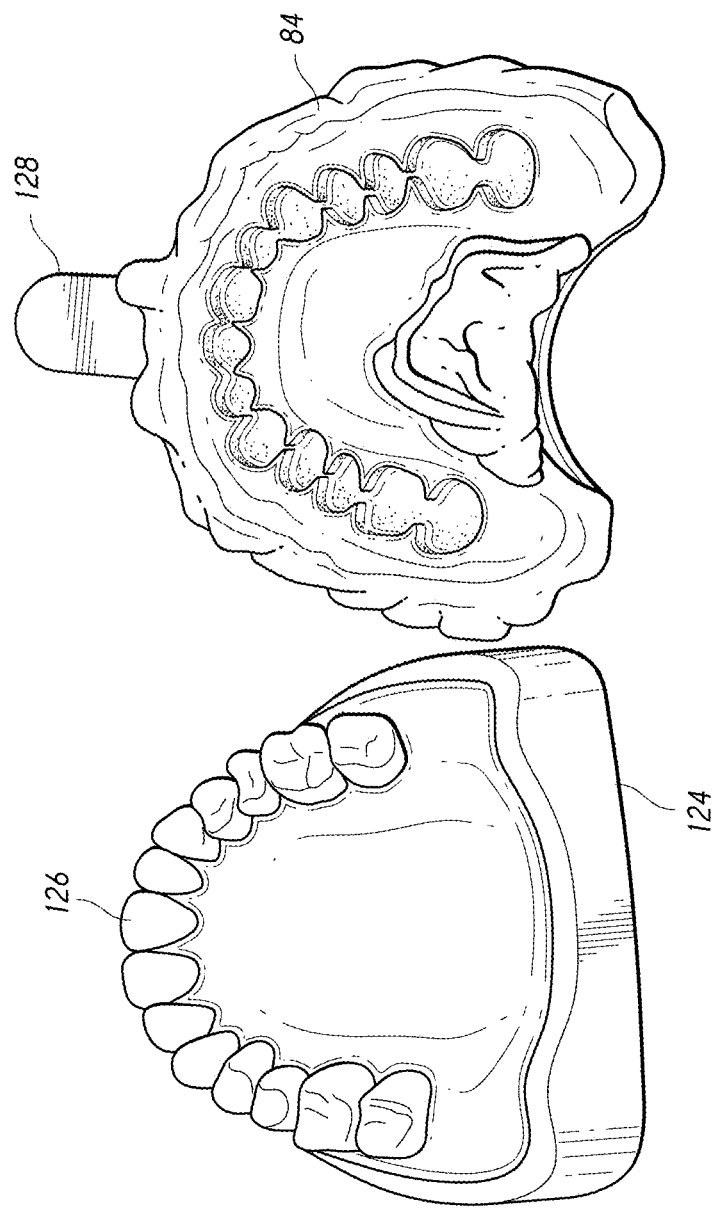
FIG. 18 is a perspective view from above of the completed upper-arch impression.

FIG. 16 shows a pre-operative physical upper-arch impression 84 being taken of the simulated patient's mouth 124 (shown as a stone model for clarity, but an impression 84 would be taken of the patient himself) using an impression tray 128. It is assumed that all four tooth buds of the wisdom teeth are present in the simulated patient. FIG. 17 is a cross-sectional view of the physical upper-arch impression 84 being taken of a simulated patient. FIG. 18 shows the completed physical upper-arch impression 84. A similar process would be performed to manufacture or fabricate a pre-operative physical lower-arch impression 84. At this time the practitioner may send impressions 84 and volume scan data to a laboratory and/or factory for processing.

The laboratory and/or factory uses the physical impressions 84 (although digital impressions 84 could be used) and volume scan data (scanning technology file) to create (including calculating, manufacturing, fabricating, selecting, and/or assembling) components of the TBA system 100 (including the surgical stents 110 and the pre-determined settings 105). The surgical stents 110 and the pre-determined settings 105 and other components are then assembled into the TBA surgical kit to be provided to the operator.

Figure 19:
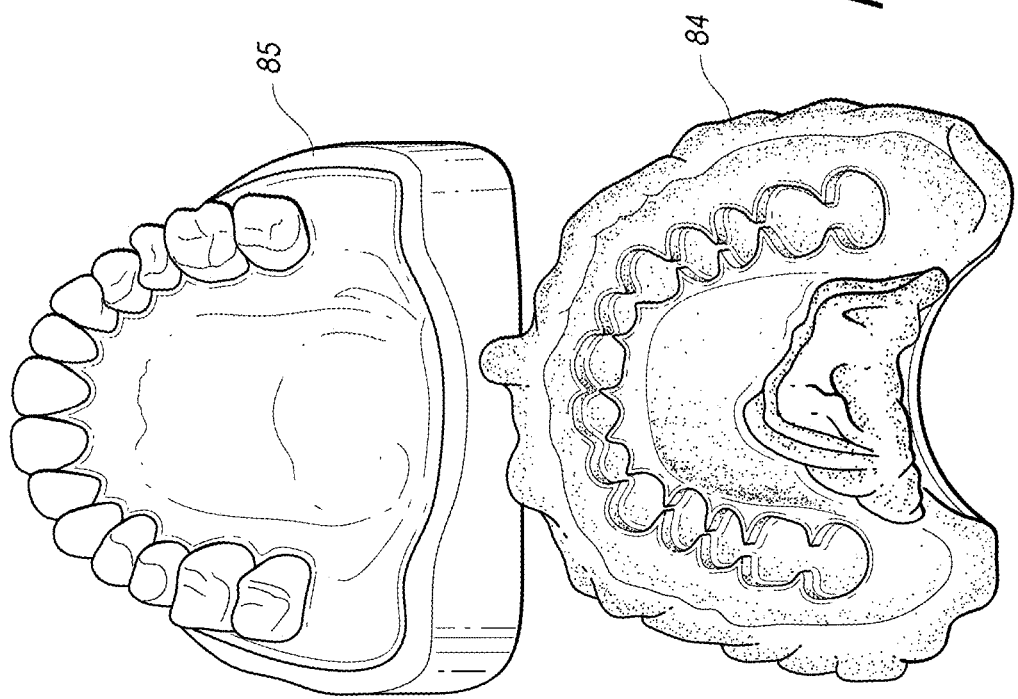
FIG. 19 is a perspective view from above of the completed upper-arch impression, along with a stone model that will serve as a "positive" for manufacturing or fabricating a custom surgical stent for that patient's upper-arch.

FIG. 19 shows the completed physical upper-arch impression 84, along with a stone model 85 that will serve as a "positive" for manufacturing or fabricating a surgical stent 110 for that patient's upper-arch. Alternatively, when using stereolithography manufacturing to manufacture or fabricate surgical stents 110, the physical impressions 84 can be computed tomography ("CT") scanned to digitize as an alternative to making physical intermediates. The CT volume scan file (scanning technology file) can then be emailed (or otherwise directly transmitted) for direct manufacturing or fabricating. Alternatively, the practitioner may handle the processing "in house."

Figure 20:
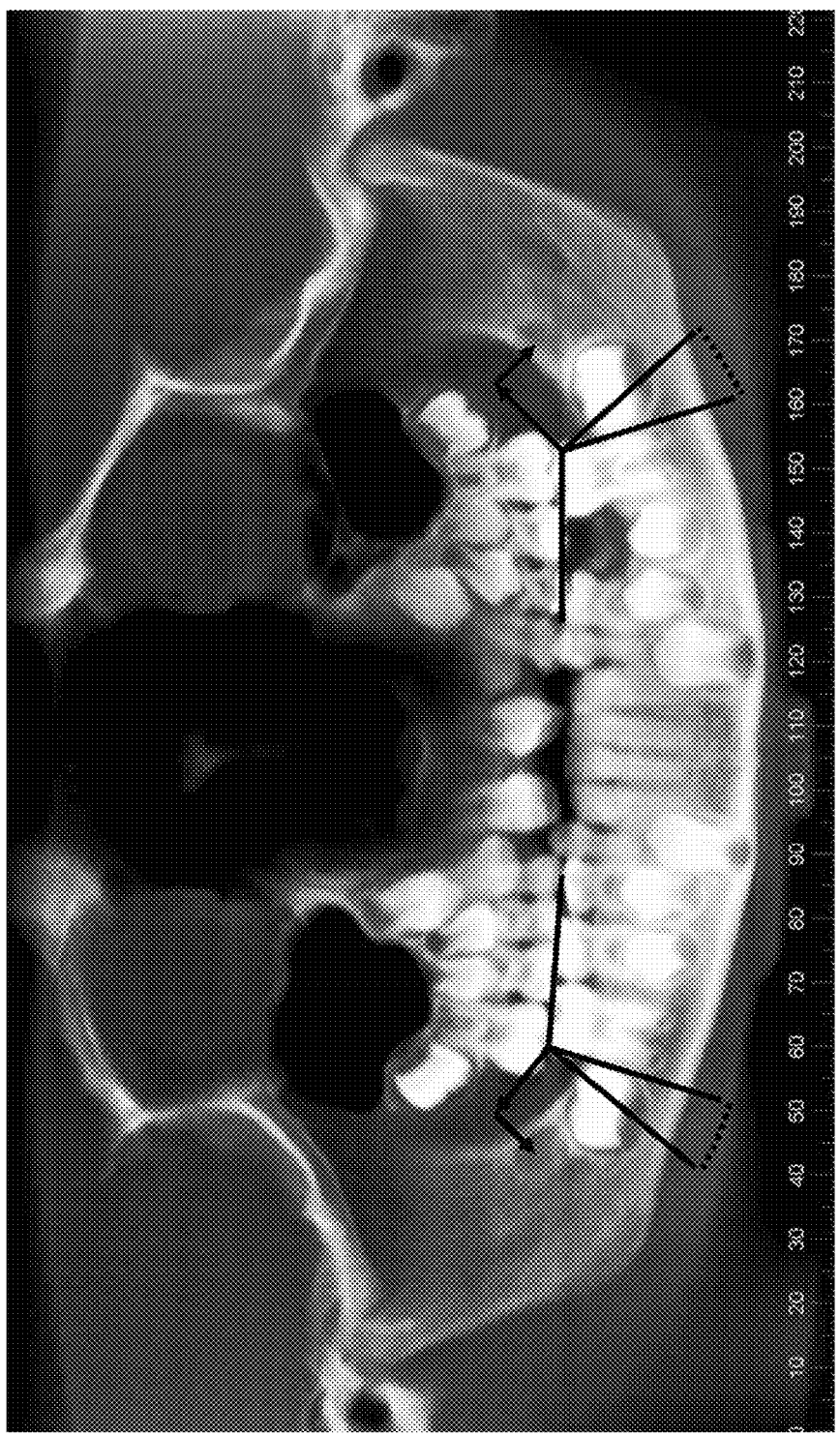
FIG. 20 is a CBCT scan with notations showing the measurement of the angle of entry into the tooth bud.
Figure 21:
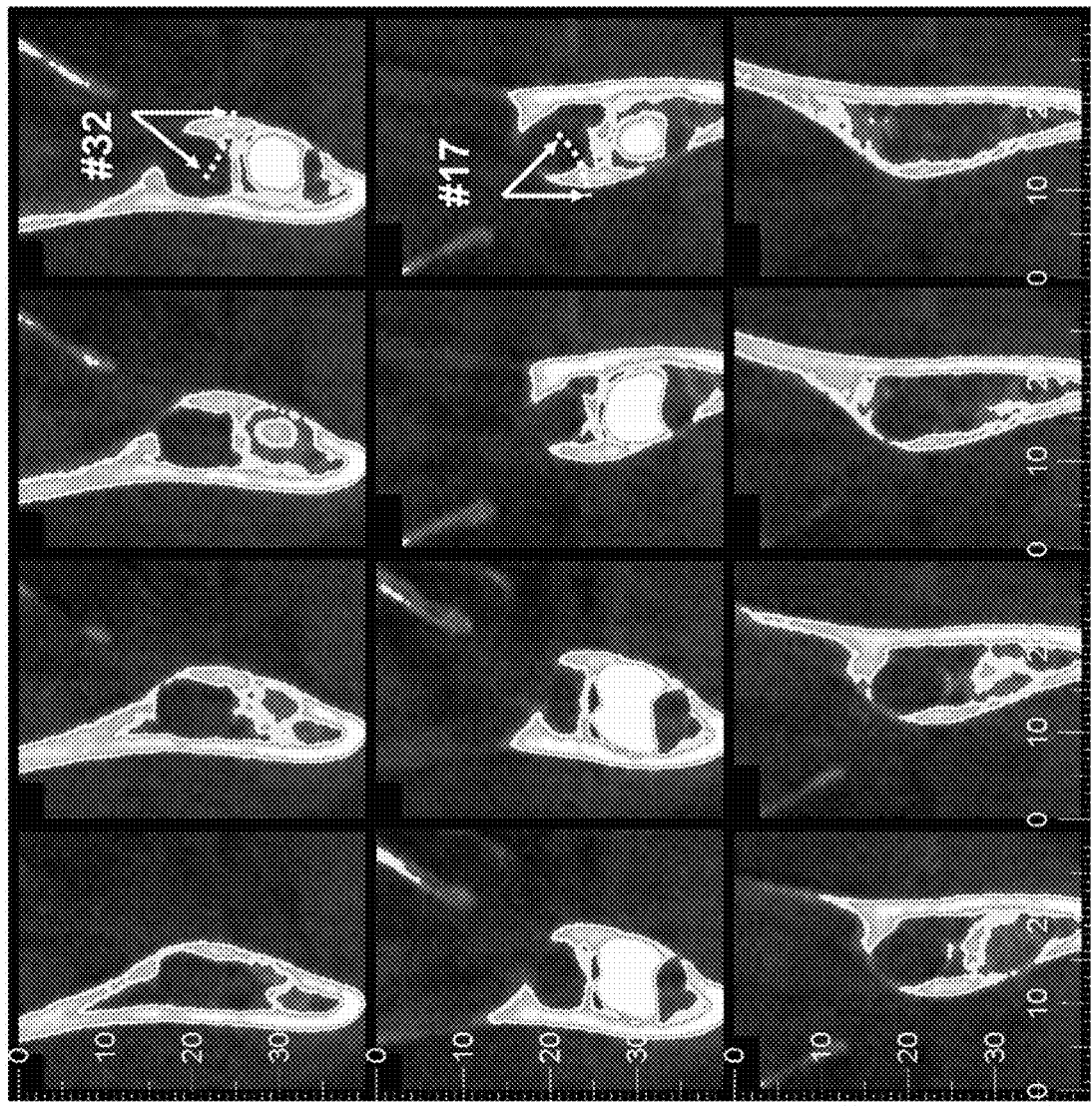
FIG. 21 is a series of X-rays with notations showing the measurement of the lateral angle of entry.
Figure 22:
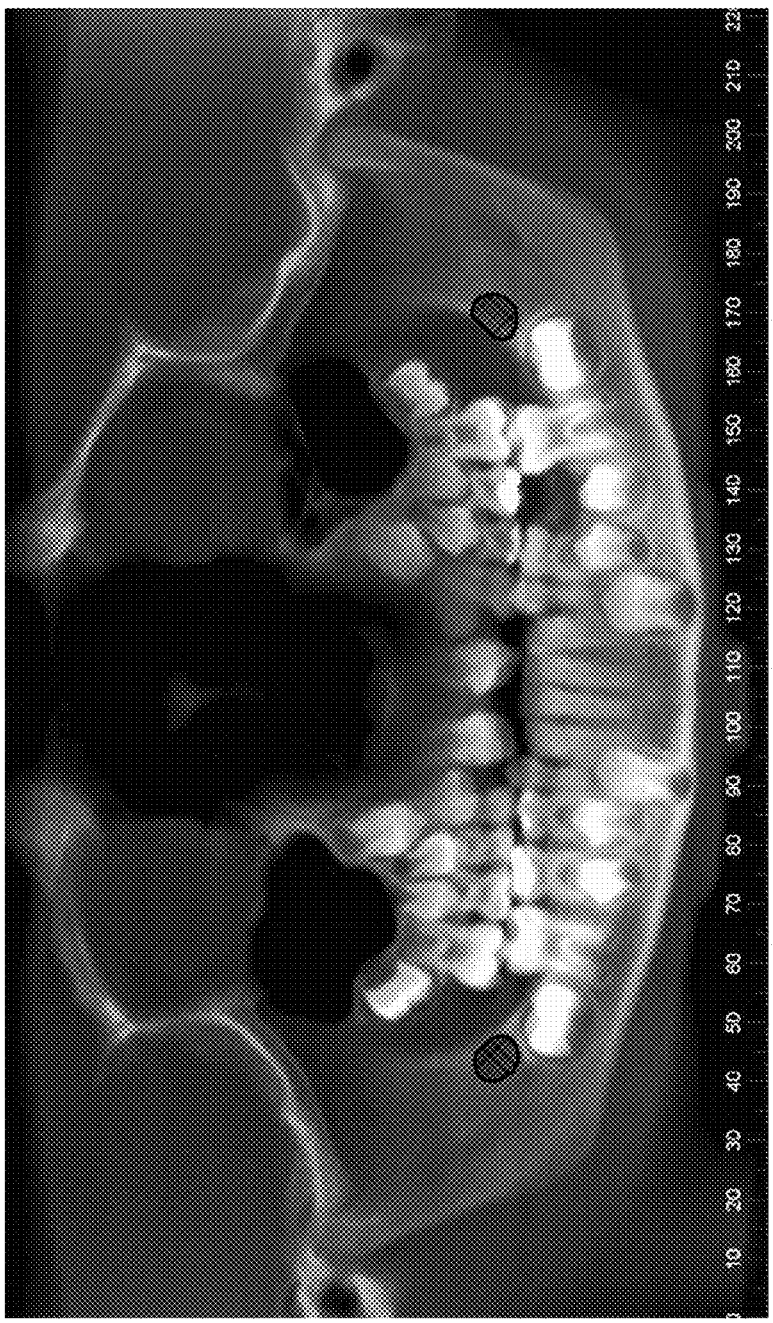
FIG. 22 is a CBCT scan with highlights showing the computed volume of each tooth bud.

FIG. 20 is a CBCT scan with notations showing the measurement of the perpendicular angle of entry into the tooth bud 120. The measurement is based on the distal aspect of the molar and the occlusal bite plane of the teeth. FIG. 21 is a series of X-rays with notations showing the measurement of the lateral angle of entry. The measurement is determined relative to the vertical axis in order to avoid the jaw's boney interferences during surgical placement of the ablation probe unit 102. FIG. 22 is a CBCT scan with highlights showing the computed volume of each tooth bud 120. CBCT volume data is used to determine and/or calculate the pre-determined settings 105.

Figure 23:
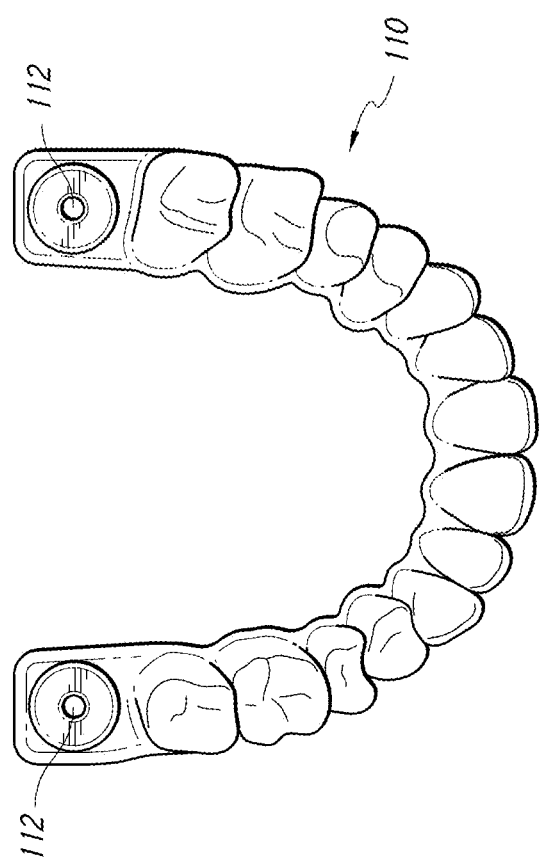
FIG. 23 is a perspective view from above of a surgical stent with two surgical guides, the stent having been manufactured or fabricated using the CBCT positioning information.

FIG. 23 shows the resulting surgical stent 110 that will be placed in a patient's mouth 124. The shown stent has two surgical guides 112 based upon the location of the patient's two tooth buds to be ablated.

The surgical stent(s) 110 and the pre-determined setting(s) 105 are provided to the operator along with the rest of the TBA surgical kit.

Prior to the surgical phase 90 of the TBA procedure 70, the ablation probe unit 102 and/or the generator 104 should be set up so that at least one pre-determined setting 105 is correctly entered for at least one tooth bud 120 with safety interlocks carefully considered. (The pre-determined settings 105 may all be entered prior to the surgical phase 90 or they may be entered one at a time.) The surgical phase 90 of the TBA procedure 70 may then be performed.

Figure 24:
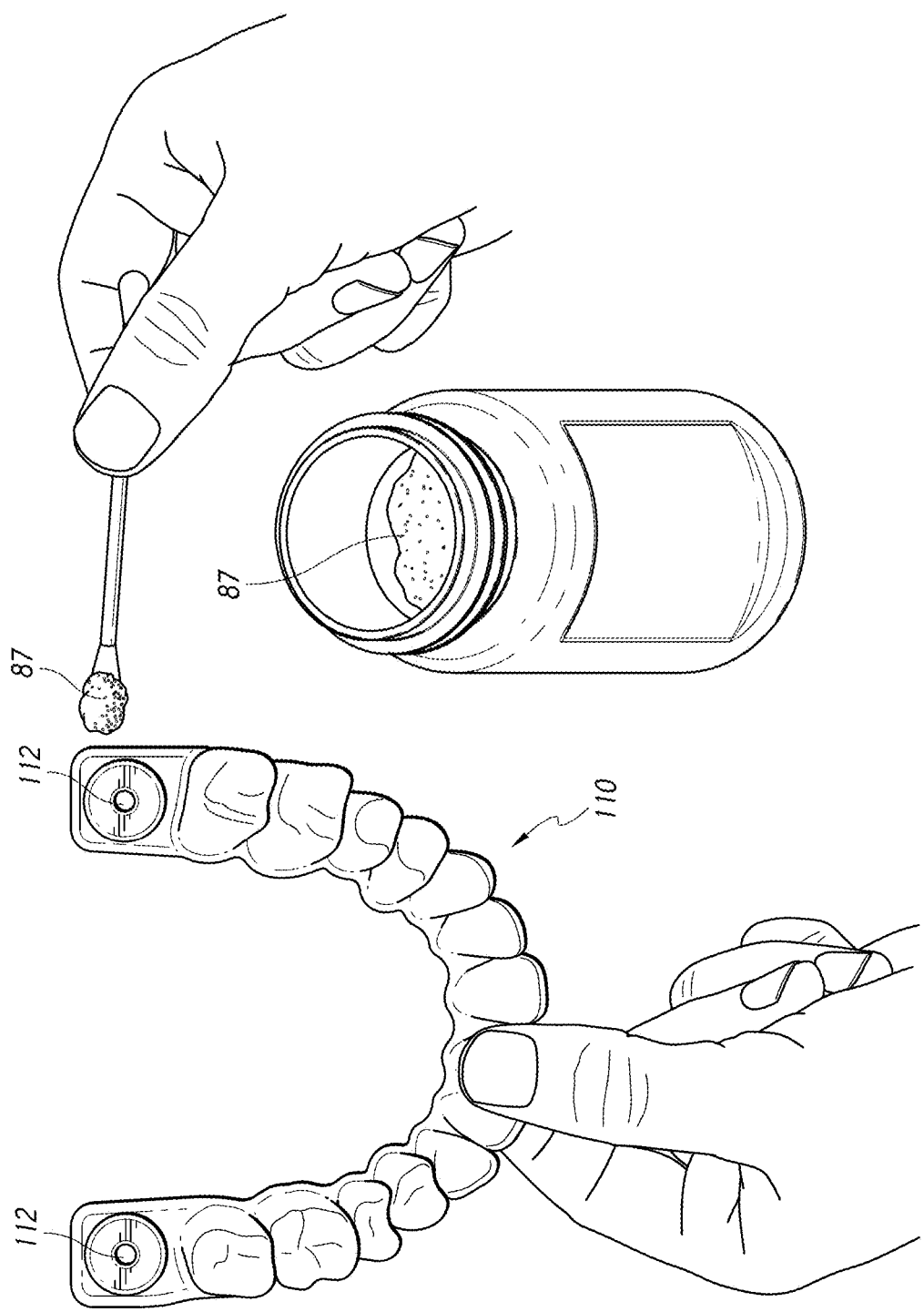
FIG. 24 is a perspective view showing topical anesthetic being applied to the base of the surgical guide.

FIG. 24 shows topical anesthetic 87 being applied to the base of the surgical guide 112 (FIG. 24) prior to the surgical stents 110 being seated in a patient's mouth 124.

Figure 25:
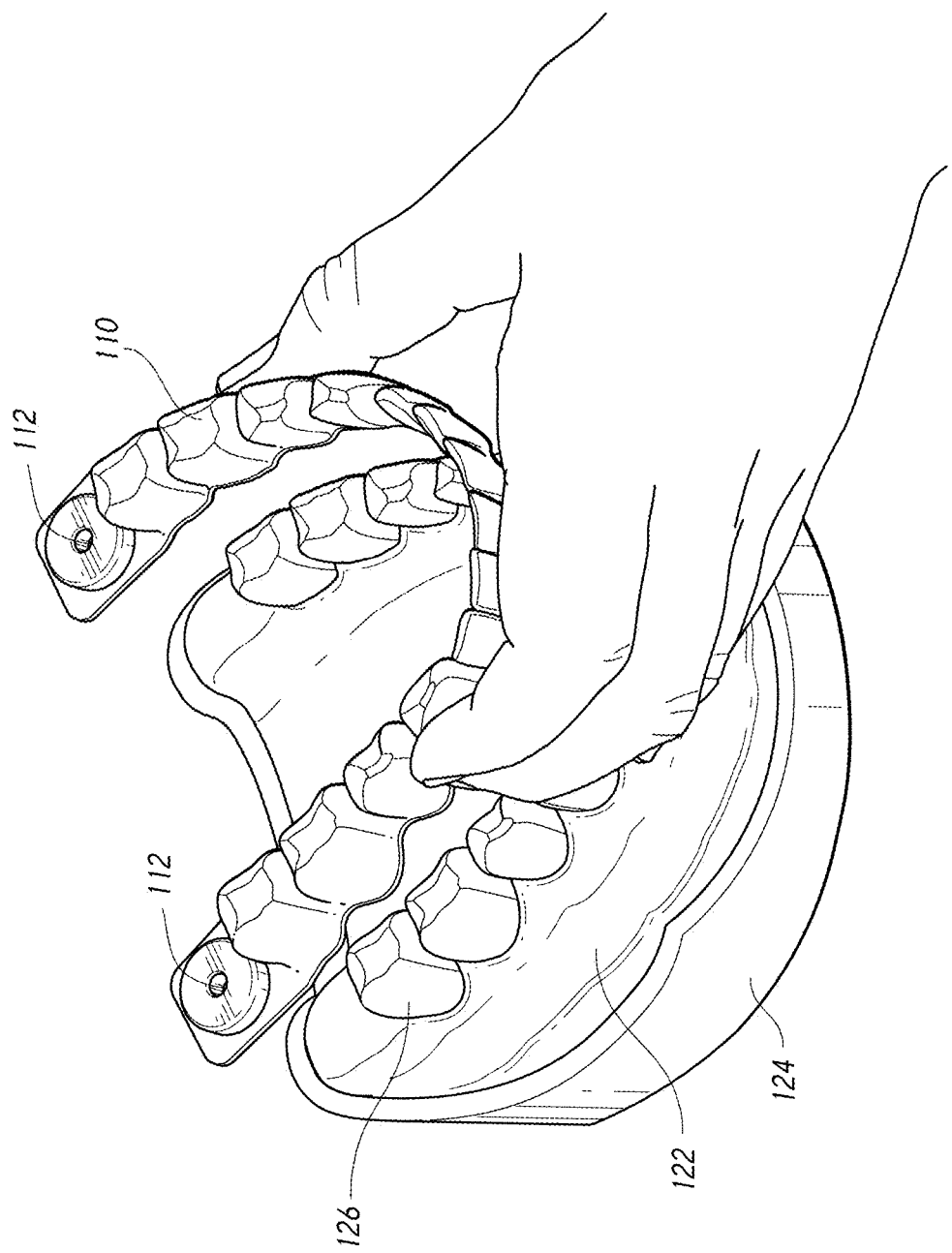
FIG. 25 is a perspective view from a front corner of a surgical stent being seated on the upper-arch of the simulated patient.

FIG. 25 shows the surgical stent 110 being seated on the upper-arch of the simulated patient's mouth 124 (shown as a stone model for clarity). This process would be repeated on the lower arch of the simulated patient.

Figure 26:
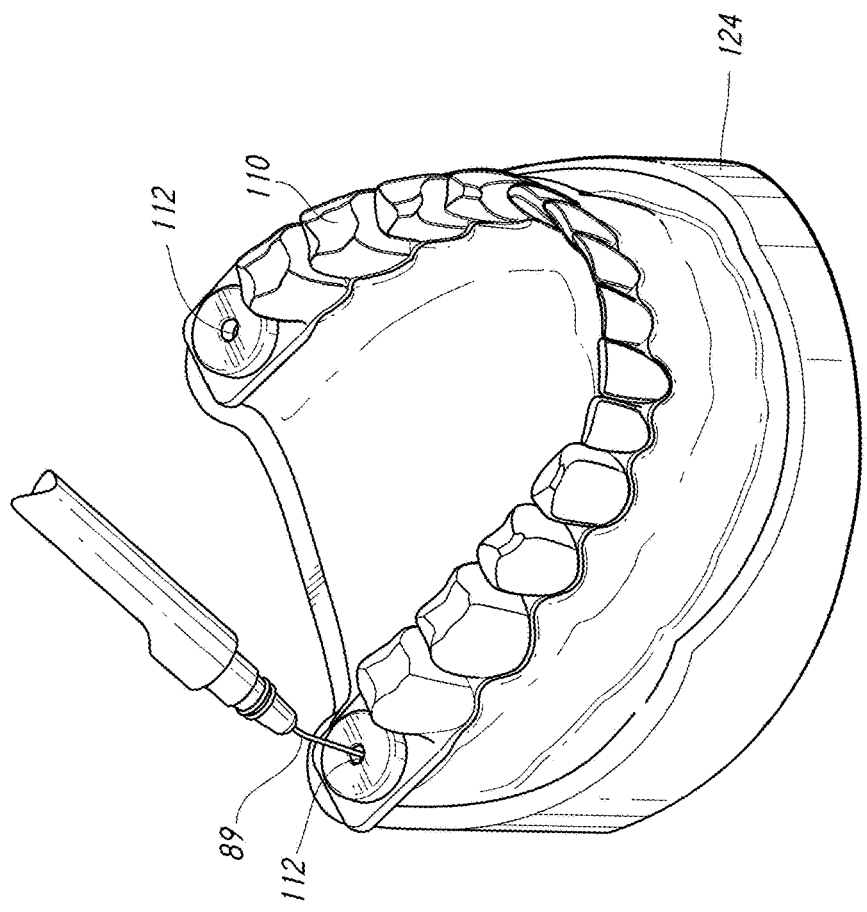
FIG. 26 is a perspective view from a front corner of a local anesthetic being injected into a tooth bud site.

FIG. 26 shows a local anesthetic being injected 89 into each site through a surgical guide 112 of the stent 110.

Figure 27:
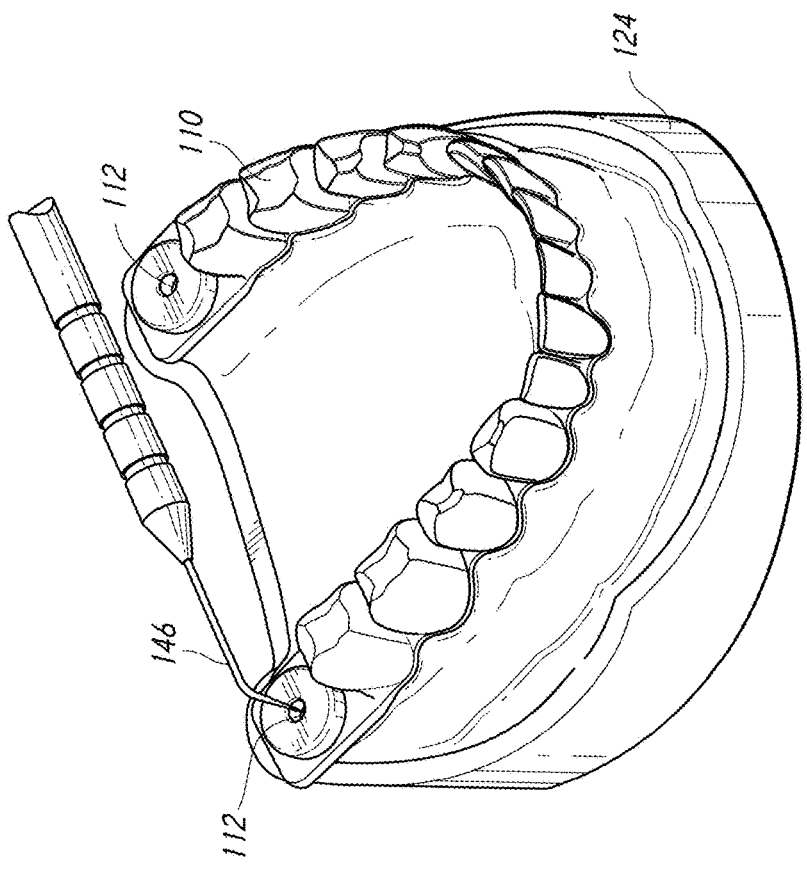
FIG. 27 is a perspective view from a front corner of a tissue trocar being used to punch to the base of a tooth bud.

FIG. 27 shows a tissue trocar 146 being used to create an access path through the gingival tissue 122 to the base of each tooth bud 120. The tissue trocar 146 is only necessary if self-introducing ablation probe tips 108 are not used.

Figure 28:
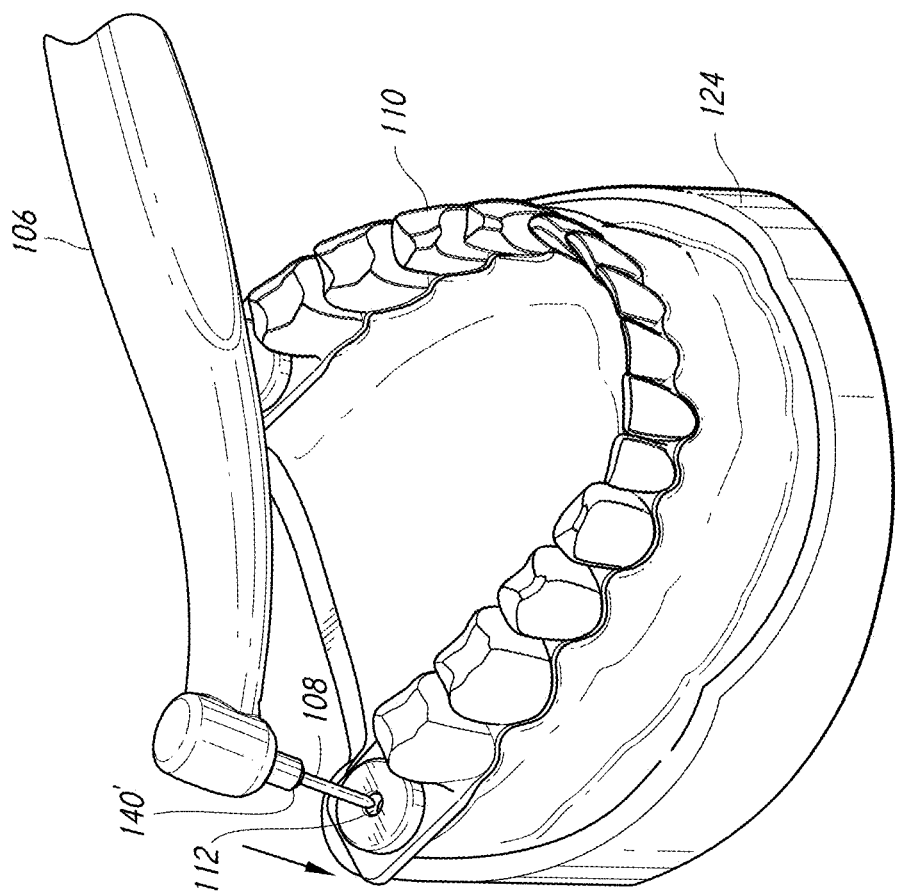
FIG. 28 is a perspective view from a front corner of an ablation probe tip with a mechanical (physical) stop being positioned through the surgical guide into the tooth bud.

FIG. 28 shows an ablation probe tip 108 with mechanical stop structure 140' (shown as a shoulder) being inserted through the surgical guide 112. This would be similar to the position of the ablation probe tip 108 in FIG. 6. (Alternatively, if the alternative ablation probe tip 148 with mechanical stop structure 150 was inserted through the surgical guide 112, the position would be similar to the position of the alternative ablation probe tip 148 in FIG. 30.)

Figure 29:
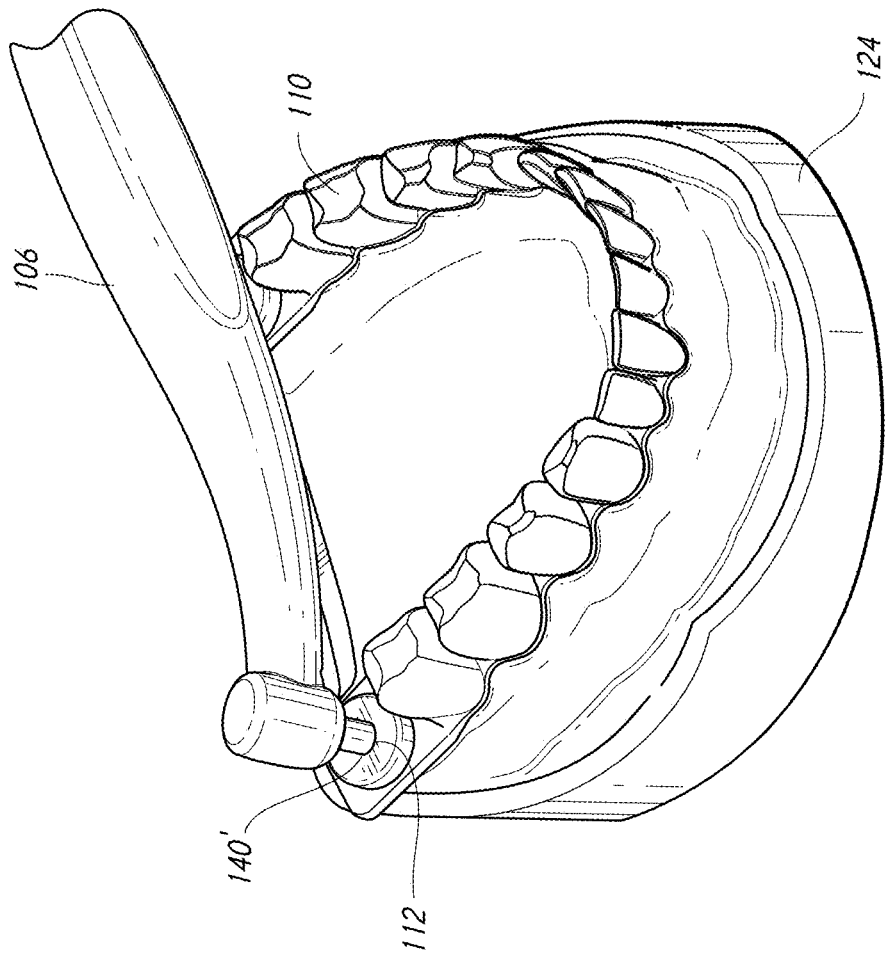
FIG. 29 is a perspective view from a front corner of the ablation probe tip being positioned in each tooth bud through the surgical guide so that the ablation probe tip's effective center of ablation is in the middle of each tooth bud.

FIG. 29 shows the ablation probe tip 108 positioned through the surgical guide 112 and into the tooth bud 120 through the surgical guide 112 so that the ablation probe tip's effective center of ablation 130a is in the middle of each tooth bud 120. This would be similar to the position of the ablation probe tip 108 in FIG. 7. (Alternatively, if the alternative ablation probe tip 148 was used, the position would be similar to the position of the alternative ablation probe tip 148 in FIG. 31.)

Figure 33:
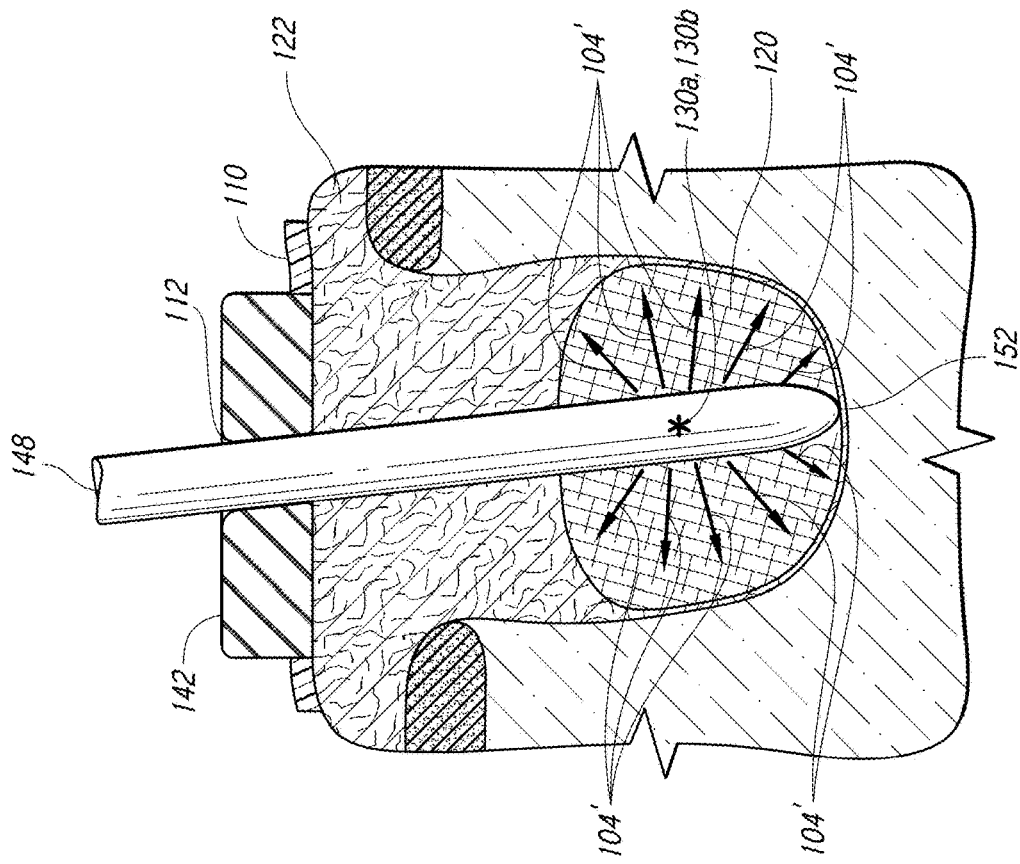
FIG. 33 is a cross-sectional side view of an alternative ablation probe tip ablating the tooth bud.
Figure 32:
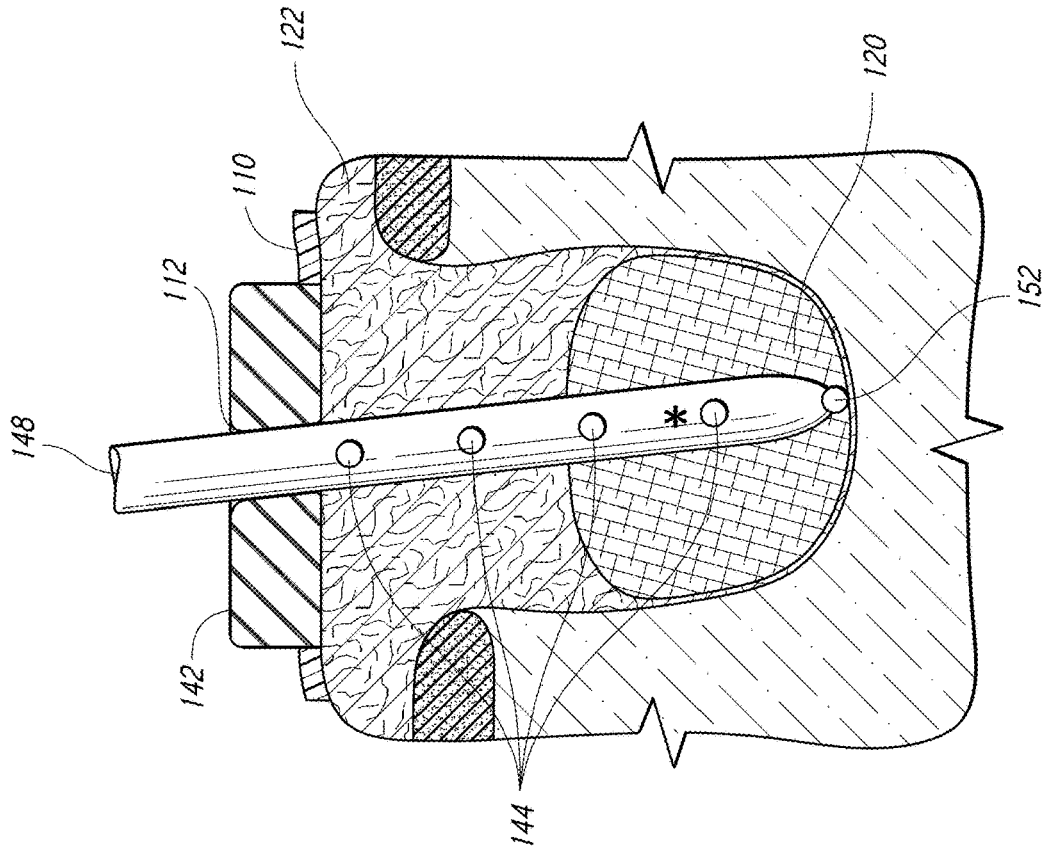
FIG. 32 is a cross-sectional side view of an alternative ablation probe tip having a linear array of temperature sensors inserted in the tooth bud.

The ablation means 104' is delivered in this position (FIG. 9, or FIG. 33 for the alternative ablation probe tip 148). The ablation means 104' is delivered based on the pre-determined settings 105 (e.g. times, intensities, and other prescribed settings unique to each tooth bud).

The ablation probe tip 108 would then be removed and the process repeated at the site of each tooth bud 120. Once the entire surgical phase 90 is complete, the surgical stents 110 are removed.

Finally, the dental practitioner or an assistant provides post-surgical instructions to the patient or a caregiver of the patient.

Alternative Scanning and Fabrication of Custom TBA Surgical Kits

An alternative to the pre-surgical phase 80 of the TBA procedure 70 described above includes simultaneous three-dimensional scanning of both hard tissues (bone and teeth) and soft tissues (tooth bud 120 and gingival tissue 122). From the information obtained using this unique simultaneous three-dimensional scanning, a custom surgical stent 110 may be manufactured or fabricated. As discussed, the custom surgical stent 110 is used in the surgical phase 90 to help with the placement of the center of ablation 130a into a tooth bud 120 that results in tooth agenesis.

The simultaneous three-dimensional scanning uses a single scan to obtain both soft tissue and hard tissue information. Soft tissue information generally does not show on a scan, although progress in volume scanning is improving and this may be possible in the near future. Known and future technologies able to provide a scan image of soft tissue are included in the scope of this invention. A typical X-ray scan will only show the hard tissue. One way to obtain both soft and hard tissue information using simultaneous three-dimensional scanning, a physical dental impression 84 is used that can be viewed on an X-ray. The physical dental impression 84 is made of materials that are preferably "contrast optimized" for high resolution X-ray volume scanning. The ideal level of contrast agent in the range of 25% to 75% radiopacity (such as barium or iodine based compounds) is mixed into the dental impression materials so that the highest level of surface detail can be picked upon when volume scanning the physical dental impression 84. The physical dental impression 84 is placed in the patient's mouth 124 during the X-ray volume scan. The resulting X-ray volume scan image would show the tooth distinguished (is visible) and the physical dental impression 84 distinguished (is visible) and the void therebetween would be the soft tissue and would therefore be "visible." The resulting X-ray volume scan with both hard and soft tissue information may then be used to formulate the custom stent 110 used in the surgical phase 90 described herein. In other words, an X-ray volume scan image is generated in which hard tissue (e.g. a tooth) is visible hard tissue and the physical dental impression 84 is a visible dental impression and soft tissue (e.g. gingival tissue 122) is "visible" as the space between the visible hard tissue and the visible dental impression.

One separate preferred pre-surgical phase 80 of the TBA procedure 70 preferably includes using X-ray volume scans of physical or digital dental impressions 84 to manufacture or fabricate surgical stents 110. The X-ray volume scan of the dental impression 84 is "super imposed" over the patient X-ray volume scan (e.g. CBCT scanning) using the dental hard tissues (the teeth) to "snap" the two volume scans together into an accurate overlay so that soft tissues of the mouth (which cannot be X-ray volume scanned or otherwise obtained directly) are accurately defined for the surgical stent manufacturing or fabricating (which must take into account the soft tissue and teeth) and probe positioning (which must take into account the tooth bud positioning from the patient's CBCT scan).

One separate preferred pre-surgical phase 80 of the TBA procedure 70 preferably includes using physical dental impression materials that are "contrast optimized" for high resolution X-ray volume scanning that is then used to manufacture or fabricate surgical stents 110. The ideal level of contrast agent (such as barium or iodine based compounds) is mixed into the physical dental impression materials so that the highest level of surface detail can be picked up on when CT volume scanning the physical dental impression 84.

Virtual Stent System

The at least one custom surgical stent 110 (a physical stent system or physical stent) could be replaced (or used in conjunction with) a virtual stent system (also referred to as a "virtual stent") in a TBA procedure or with a TBA system. As set forth in the Background, U.S. Pat. No. 8,221,121 to Berckmans, III et al., U.S. Pat. No. 8,013,853 to Douglas, et al., U.S. Pat. No. 7,812,815 to Banerjee, et al., U.S. Pat. No. 7,457,443 to Persky, U.S. Pat. No. 7,249,952 to Ranta, et al., U.S. Pat. No. 5,688,118 to Hayka et al., U.S. Patent Publication No. 20100316974 to Yau, et al., U.S. Patent Publication No. 20100311028 to Bell, et al., and U.S. Patent Publication No. 20090253095 to Salcedo, et al. are references that address aspects of virtual dentistry. These references are hereby incorporated by reference in their entirety. Although none of these references are used in a TBA procedure or with a TBA system, many of the details of the virtual stent system may be implemented using aspects described in these references.

As a broad concept, a virtual stent system uses the three-dimensional volume scans (computed tomography volume scans) created using scanning technologies (e.g. computed tomography volume scanning such as cone beam computed tomography (CBCT) scanning and MRI volume scanning) displayed on a display system (e.g. a computer screen). The three-dimensional volume scans are taken of a specific patient on which the TBA procedure is being performed. Calculations are made to determine or calculate the parameter settings, the treatment time settings, the pre-defined angle ($\phi$), and/or the pre-defined depth (x). The calculations of the pre-defined angle ($\phi$) and pre-defined depth (x) are used to define a three-dimensional path of insertion through which the ablation probe tip 108, 148 accesses the gingival tissue 122 and the tooth bud 120 so that the center of ablation 130a substantially coincides with or overlaps the middle of the tooth bud 130b. Using sensors 230 on the ablation probe tip 232 and/or the hand piece 106 to transmit movement, a real-time representation of the ablation probe tip 232 and/or the hand piece 106 is overlaid on the displayed three-dimensional volume scans. Movement of the ablation probe tip 232 is displayed in real-time. (It should be noted that the sensors 230 may be the ablation probe tip itself, the hand piece itself, sensors such as those described in the references incorporated herein, and any known or yet to be discovered sensors that are sensible from within a patient's mouth and are safe for use in a patient's mouth. It should also be noted that the sensors 230 have associated sensing technology (not shown) for sensing the sensors 230 and communicating and/or interpreting the position of the ablation probe tip 232 and/or the hand piece 106 so that a representation of the ablation probe tip 232 and/or the hand piece 106 is displayed on the display 240. This sensing technology may be any known or yet to be discovered sensing technology capable of sensing the sensors within a patient's mouth (and is safe to use for such a purpose) including sensing technology described in the references incorporated herein.) The operator is able to monitor in real time the relationship of the effective center of ablation 130a of the ablation probe tip 232 as compared to the middle of the tooth bud 130b.

Figure 36:
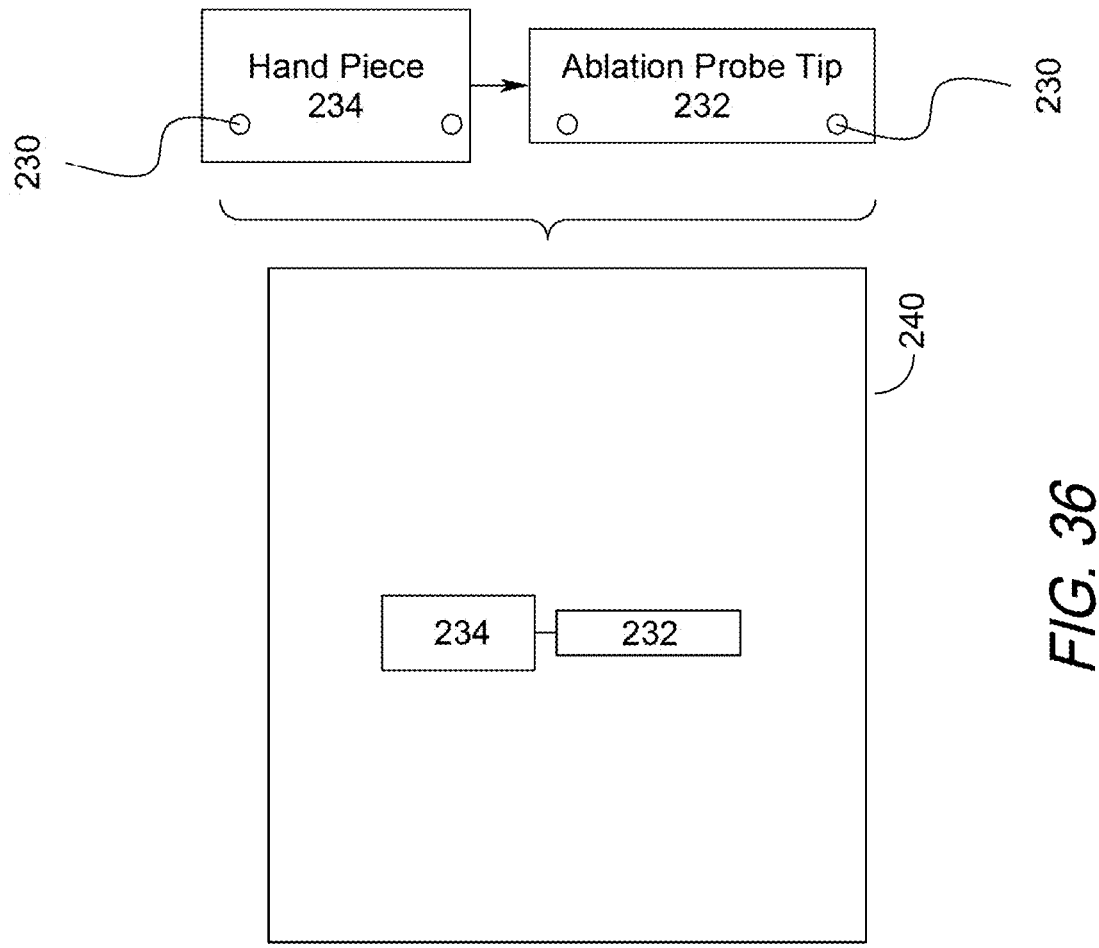
FIG. 36 is a simplified block diagram of a vertical hand piece and ablation probe tip with sensors and a display with a representation of the vertical hand piece and ablation probe tip displayed thereon.
Figure 35:
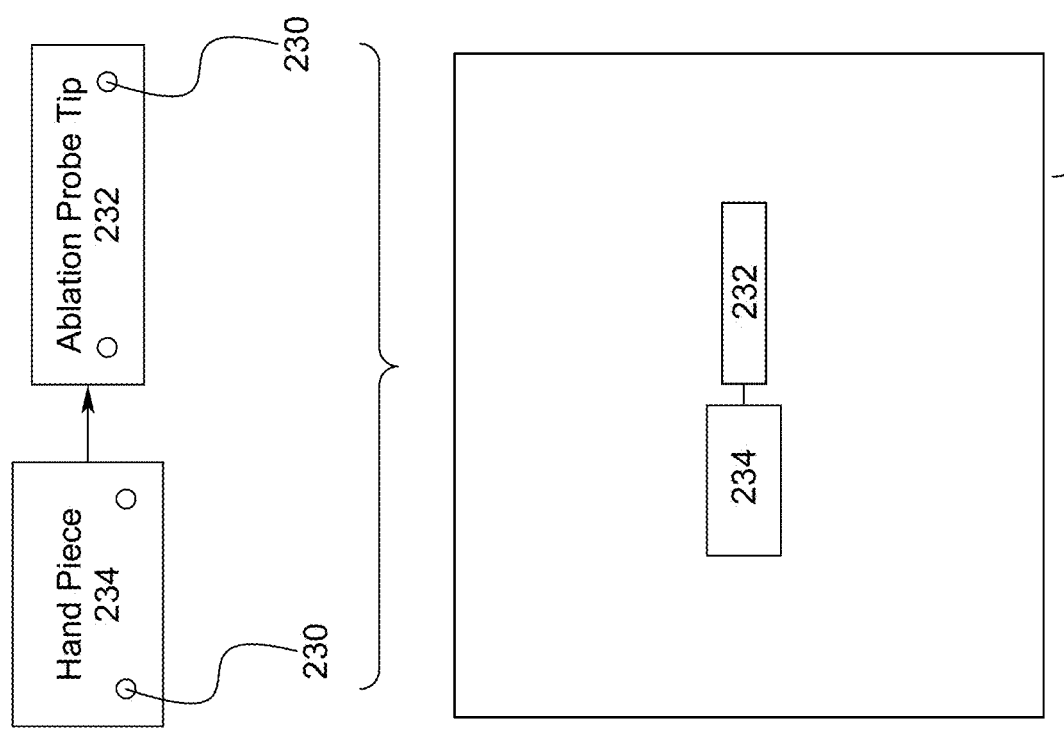
FIG. 35 is a simplified block diagram of a horizontal hand piece and ablation probe tip with sensors and a display with a representation of the horizontal hand piece and ablation probe tip displayed thereon.

FIG. 35 shows a horizontal hand piece 234 and ablation probe tip 232 with sensors 230 and a display 240 with a representation of the horizontal hand piece 234 and ablation probe tip 232 displayed thereon. FIG. 36 shows a vertical hand piece 234 and ablation probe tip 232 with sensors 230 and a display 240 with a representation of the vertical hand piece 234 and ablation probe tip 232 displayed thereon. The sensors 230 would pick up movement of the hand piece 234 and ablation probe tip 232 in real time and would display the movement of the sensored hand piece 234 and sensored ablation probe tip 232 as real-time representations of the hand piece 234 and ablation probe tip 232 on the display 240.

Figure 38:
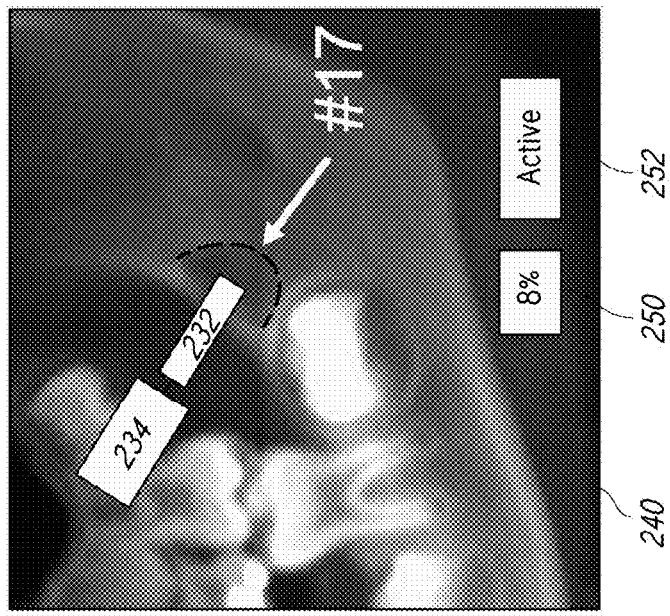
FIG. 38 is a simplified block diagram with an exemplary patient X-ray volume scan shown on a display with a representation of the sensored hand piece and ablation probe tip displayed as well as exemplary indicators of position (in terms of percentage of the average diameter of the tooth bud)
Figure 37:
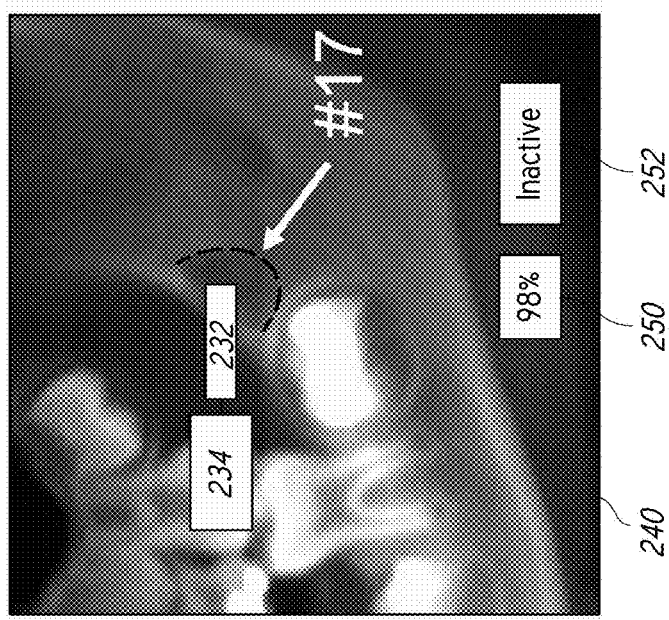
FIG. 37 is a simplified block diagram with an exemplary patient X-ray volume scan shown on a display with a representation of the sensored hand piece and ablation probe tip displayed as well as exemplary indicators of position (in terms of percentage of the average diameter of the tooth bud) and status simultaneously shown on the display in real time, the position shown as 98% (far from the middle of the tooth bud) and the status shown as inactive.

FIGS. 37 and 38 show an exemplary patient X-ray volume scan shown on a display 240 with a representation of the hand piece 234 and/or ablation probe tip 232 displayed as well as exemplary indicators of position (position indicator 250) and status (status indicator 252) shown on the display 240 in real time. FIG. 37 shows the sensed ablation probe tip 232 just barely inserted into the tooth bud such that the center of ablation 130a is relatively far from the middle of the tooth bud 130b. The position indicator 250, therefore, would show a large percentage (shown as 98% which is the percentage of the average diameter of the tooth bud at which the center of ablation 130a is located in this position). The status indicator 252 is shown as "inactive" because the system would not be activated (it is not delivering ablation means 104') so far from the middle of the tooth bud 130b. FIG. 38 shows the ablation probe tip 232 in a relatively optimal position for ablation within the tooth bud. In other words, the center of ablation 130a is relatively close to the middle of the tooth bud 130b. The position indicator 250, therefore, would show a small percentage (shown as 8% which is the percentage of the average diameter of the tooth bud at which the center of ablation 130a is located in this position). The status indicator 252 is shown as "active" because the system might be activated (delivering ablation means 104') this close to the middle of the tooth bud 130b.

FIG. 39 is an enlarged view of the display 240 showing virtual surgical guide angle markings 260, a virtual stop marking 262, and virtual target markings 264. The virtual surgical guide angle markings 260 are based on the three-dimensional path of insertion (defined by the pre-defined angle ($\phi$) and pre-defined depth (x)). Although these markings may be shown using an enlarging setting for the display 240, they may also be present on the regular (non-enlarged) display 240. In preferred embodiments, the system would not be able to be activated if the center of ablation 130a was not in proper relationship to the middle of the tooth bud 130b.

The virtual surgical guide angle markings 260 function in a manner similar to the physical surgical guide 112 (providing angle guidance) as they show the representation of the ablation probe tip 232 in the proper pre-defined angle ($\phi$) in which the operator can guide the ablation probe tip 232 so that its center of ablation 130a is placed into the middle of the tooth bud 130b. The guide angle markings 260 show the proper path so that the user would see the representation of the ablation probe tip 232 outside the path if the sensored ablation probe tip 232 is not on the proper path. Preferably the representation is three-dimensional so that the operator would see a three-dimensional representation of the ablation probe tip 232 and a three-dimensional representation of the path of insertion. Further, the operator may be alerted that the sensored ablation probe tip 232 is not at the proper pre-defined angle using, for example, visual indicators (e.g. two-dimensional or three-dimensional graphical representations, lights on the display 240, warning messages on the display 240, or lights on the hand piece 234 or ablation probe tip 232), audible indicators (e.g. buzzing or an audible warning message), tactile indicators (e.g. the vibrating of the hand piece 234), or a combination thereof.

At least one virtual stop marking 262 is displayable on the display 240 to provide stop information to limit the depth of said sensored ablation probe tip 232 to a pre-defined depth (x). The virtual stop marking 262 functions in a manner similar to the physical stops 140, 150 (which would not technically be needed for the sensored ablation probe tip 232) as the virtual stop marking 262 limits (or at least provides a visual indication of the proper limit for) the representation of the ablation probe tip 232 so that its center of ablation 130a is at the proper pre-defined depth (x) to be placed into the middle of the tooth bud 130b. The operator may be alerted that the center of ablation 130a is not at the proper pre-defined depth (x) using, for example, visual indicators (e.g. lights on the display 240, warning messages on the display 240, or lights on the hand piece 234 or ablation probe tip 232), audible indicators (e.g. buzzing or an audible warning message), tactile indicators (e.g. the vibrating of the hand piece 234), or a combination thereof. It should be noted that the virtual stop marking 262 may not be at the middle of the tooth bud 130b. The virtual stop marking 262 would take into consideration the ablation probe tip 232 and its center of ablation 130a and indicate the proper position for the ablation probe tip 232 such that its center of ablation 130a (which may not be at its ultimate tip) is positioned at the middle of the tooth bud 130b. The virtual stop marking 262 and/or the alerts (e.g. visual indicators, audible indicators, tactile indicators, or a combination thereof) are a type of "stop information," the ablation probe tip 108, 148 being depth limited to the depth indicated by the stop information (which would be the depth at which the center of ablation 130a substantially coincides with or overlaps with the middle of the tooth bud 130b).

The virtual target markings 264 are an optional feature (in that they are not strictly necessary if there are virtual surgical guide angle markings 260 and a virtual stop marking 262). Alternatively, the virtual target markings 264 could replace one or both of the virtual surgical guide angle markings 260 and a virtual stop marking 262. The virtual target markings 264, however, might represent the "middle" of the tooth bud 130b within, for example, approximately 50%, 25%, and 10% of the average diameter of the tooth bud 120. This information could be helpful to the operator. The operator may be alerted that the ablation probe tip 232 is not at the proper position using, for example, visual indicators (e.g. lights on the display 240, warning messages on the display 240, or lights on the hand piece 234 or ablation probe tip 232), audible indicators (e.g. buzzing or an audible warning message), tactile indicators (e.g. the vibrating of the hand piece 234), or a combination thereof.

The sensored hand piece 234 and/or ablation probe tip 232 overlapped on the patient X-ray volume scan on the display 240 and the indicators 250, 252 and/or markings 260, 262, 264 thereon are the major components of a preferred implementation of the virtual stent system in a TBA procedure or with the TBA system. Some versions of the virtual TBA system do not include any physical stent 110, because the virtual stent system guides the sensored hand piece 234 and/or ablation probe tip 232 so that the center of ablation 130a is placed into the middle of the tooth bud 130b.

In a TBA procedure, the virtual stent system may be operated manually, automatically (e.g. computer controlled), or a combination thereof. The sensored hand piece 234 in an automatic system (or a combination system) may be part of a robotic system that physically manipulates the physical sensored hand piece 234 and/or ablation probe tip 232. The automatic system (or a combination system) may also control the generator 104 as described herein. If the system is being operated manually, the system acts as a failsafe in that it may automatically control or have override control of the status (making the system inactive) of the virtual stent system such that if the center of ablation 130a is not in the middle of the tooth bud 130b, the system will not allow ablation or will cease ablation if the center of ablation 130a moves out of the middle of the tooth bud 130b (or if any other problem is sensed). On the other hand, if the system is being operated automatically, the operator acts as a failsafe in that he may manually control or have override control of the status (making the system inactive) of the virtual stent system such that if the center of ablation 130*a* is not in the middle of the tooth bud 130*b*, the system will not allow ablation or will cease ablation if the center of ablation 130*a* moves out of the middle of the tooth bud 130*b* (or if he sees any other problem).

For most of the specific steps set forth below, the operator may watch the step being performed on the display 240 as he manually (physically) manipulates the sensed ablation probe tip 232 to perform the step. In such a case, the system would monitor the progress and alert the operator if there was a problem (e.g. the ablation probe tip 232 is not at the proper pre-defined angle) using, for example, visual indicators, audible indicators, tactile indicators, or a combination thereof. As set forth, during manual operation the system may automatically override the status (making the system inactive) to prevent ablation or further ablation if there is any problem (e.g. if the center of ablation 130*a* moves out of the middle of the tooth bud 130*b*). On the other hand, the operator may monitor the step being performed on the display 240 as the automatically controlled sensed ablation probe tip 232 performs the step automatically (e.g. using a robotics system). As set forth, the operator may manually override the status (making the system inactive) to prevent ablation or further ablation if there is any problem (e.g. if the center of ablation 130*a* moves out of the middle of the tooth bud 130*b*).

As shown in FIG. 40, the following steps are exemplary steps in a TBA procedure using the virtual stent system.

Parameter Setting Step 300: The ablation probe properties (center of ablation, diameter, length, power output properties, etc.) are programmed into the virtual guide software along with the patient's specific ablation parameters (size of tooth bud, power setting, time to ablate, etc). These ablation probe properties are used in steps such as the guiding step and the ablating step. These properties may be obtained using a procedure similar to that shown in FIG. 12 and discussed herein. The major difference between the procedure of FIG. 12 and one used to calculate the parameters for the TBA procedure using the virtual stent system is that the virtual system would not necessarily require the production of a physical stent, but would instead need the calculation of the virtual surgical guide angle markings 260, a virtual stop marking 262, and/or virtual target markings 264 to be displayed on the display 240.

Calibrating Step 302: As set forth above, the sensed hand piece 234 and/or ablation probe tip 232 is represented overlapped on the patient X-ray volume scan on the display 240. In a perfect world, this step would be optional. In the real world, however, an operator would want to verify that the representation of the sensed hand piece 234 and/or ablation probe tip 232 is in the proper position relative to the patient's mouth. This may be accomplished using visual checks such as the operator positioning the physical absolute tip of the ablation probe tip 232 in relation to a known physical point of the patient's mouth. This may be, for example, an easily recognizable point on one of the patient's erupted teeth. The operator then confirms that the virtual absolute tip of the ablation probe tip 232 is in the same relationship with the same point of the patient's mouth shown on the patient X-ray volume scan on the display 240. If these do not match, appropriate adjustments may be made.

Anesthetizing Step 304: The patient is anesthetized using the sensed ablation probe tip 232 or a sensed specialized anesthetic tip (similar to the one shown and discussed in relation to FIG. 26 and having sensors thereon). The virtual stent system may be used as the visual guide (e.g. virtual surgical guide angle markings 260, a virtual stop marking 262, and/or virtual target markings 264) for separately inserting the anesthetic needle and recommending the placement of the needle in the middle of the tooth bud. The sensed anesthetic needle may be of a known length and may be displayed on the display 240 in order to place the sensed anesthetic needle in the middle of the tooth bud 130*b* so as to provide "virtual guided anesthesia" into the tooth bud 120. When the system indicates that the anesthetic needle is properly placed, the anesthetic is administered manually or automatically. The monitoring and override safeguards are preferably used in this step, although damage caused by incorrect placement of the sensed anesthetic needle would be relatively minor.

Introducing Step 306: In this step the sensed ablation probe tip 232 is introduced to the tooth bud 120. The operator may watch the insertion process on the display 240 as he physically manipulates the sensed ablation probe tip 232. Alternatively, the operator may monitor the insertion process on the display 240 as the sensed ablation probe tip 232 is inserted automatically (e.g. using a robotics system). The introducing step may be implemented as a single step if the sensed ablation probe tip 232 is self-introducing. Alternatively, the introducing step may be implemented in two steps if the sensed ablation probe tip 232 is not self-introducing. The two steps would gain access to the tooth bud 120 through the stent surgical guides 112 by creating (introducing) a small surgical access path opening through the gingival tissue 122 approximately 0.1 mm to 2.0 mm (and more particularly 0.5 mm to 1.0 mm) in diameter using sensed tissue trocars or other sharp tools. Then, there is the actual step of introducing the non-self-introducing sensed ablation probe tip 232. The monitoring and override safeguards described herein are preferably used in this step.

Guiding Step 308: In this step the sensed ablation probe tip 232 is guided by the virtual surgical guide angle markings 260 (FIG. 39) and the virtual stop marking 262 (FIG. 39) to a position in which the effective center of ablation 130*a* of the ablation probe tip is in the middle of the tooth bud 130*b*. The operator may watch the insertion process on the display 240 as he physically manipulates the sensed ablation probe tip 232. The virtual target markings 264 (FIG. 39) may also provide an indication that the sensed ablation probe tip 232 is within approximately 50%, 25%, and 10% of the average diameter of the tooth bud 120. The position indicator 250 (FIGS. 37 and 38) provide even more accurate data as to the positioning of the effective center of ablation 130*a* of the ablation probe tip relative to the middle of the tooth bud 130*b*. If the operator were manually manipulating the sensed ablation probe tip 232, the system would monitor the progress and alert the operator that the ablation probe tip 232 is not at the proper position using, for example, visual indicators, audible indicators, tactile indicators, or a combination thereof. Alternatively, the operator may monitor the progress on the display 240 as the sensed ablation probe tip 232 is inserted automatically (e.g. using a robotics system). The monitoring and override safeguards described herein are preferably used in this step.

Readying Step 310: Visual indications on the display 240 (and possibly audible or tactile indications) are used to indicate that the effective center of ablation 130*a* of the ablation probe tip is properly positioned relative to the middle of the tooth bud 130*b*. Such visual indications may include the position indicator 250 reaching a proper number (this may be based on pre-determined tolerances that may be programmed into the system with the other parameters). Other visual indicators could be color changes, flashing, or text (e.g. "ready to ablate") on the visual display 240. The operator may also have to provide a "ready input" indicating that he has independently verified the ready condition and is authorizing the ablation.

Ablating Step 312: When both the operator and the system are "ready" the ablation may be triggered and ablation means 104' is delivered through the properly positioned ablation probe tip 232 to middle of the tooth bud 130*b*. The monitoring and override safeguards described herein may be used and may allow either the system (automatic) or the operator (manual) to cease ablation for any reason. During ablation, a visual indicator (e.g. a countdown reading based upon the programmed parameters) or other indicators preferably provide constant feedback to the operator about the ablation progress. The system preferably delivers the correct ablation energy level for the size of the tooth bud by actively measuring the energy being input (a closed loop system) and continuously correcting the physical position of the effective center of ablation 130*a* of the ablation probe tip relative to the middle of the tooth bud 130*b*. The monitoring and override safeguards described herein are preferably used in this step.

Completing Step 314: Based on constant monitoring and feedback pertaining to the tooth bud and surrounding tissues, the ablation process, the system itself, and/or the pre-determined parameter settings and/or treatment time settings, the operator or the system may cease the delivery of ablation means 104' to the middle of the tooth bud 130*b*. The ablation probe tip 232 may then be removed. The monitoring and override safeguards described herein are preferably used in this step.

It should be noted that the order of these steps is meant to be exemplary and is not meant to be limiting. For example, the parameter setting step 300 may be performed before or after the calibrating step 302 and/or anesthetizing step 304. Similarly, the calibrating step 302 may be performed before or after the anesthetizing step 304. Also, some of the steps are optional or may be performed separate from the TBA procedure. For example, if the patient was anesthetized for another procedure, the anesthetizing step 304 would not be necessary.

Alternative Procedures and Systems

Separate preferred surgical procedures preferably include the ablation of "non-tooth" bud lesions or tumors of the maxilla or mandible. In such a situation, a custom stent would be manufactured or fabricated with guides to guide an ablation probe tip 108 to such a lesion or tumor located at least one lesion or tumor surgical site. The process could then be used to ablate such lesion or tumor.

Separate TBA surgical procedures preferably include the use of ultrasound scanning with combined ultra-high energy ultrasound ablation but without the use of a surgical stent for transgingival tooth bud ablation that results in tooth agenesis. This can be described as direct ultrasound scanning with ultra-high energy ultrasound built into the same scanning head.

Comparison to the Silvestri Study

As set forth in the Background section of this document, the article entitled "Selectively Preventing Development Of Third Molars In Rats Using Electrosurgical Energy" by Silvestri et al. describes a pilot study that tests the hypothesis that third molars can be selectively prevented from developing. The results of the Silvestri study were mixed at best, with only ten rats out of thirty-three showing the desired result of no intraoral or radiographic evidence of third molar development. One reason that the Silvestri process was not successful may have had to do with the fact that the Silvestri process was inexact. For example, the Silvestri process relied on molds taken from molds of the mouths of euthanized rat pups rather than using molds fabricated for the rat pup on which the procedure was to be performed. The present invention uses the patient's mouth on which the procedure is to be performed. Another way in which the Silvestri process was inexact was that the Silvestri process did not locate the forming tooth bud 120. More specifically, the Silvestri process did not locate or determine the location of the forming tooth bud 120 pre-operatively relative to the landmarks that he used. Silvestri even states " . . . when electrosurgical energy is applied near the invisible tooth anlage in the tiny mouth of newborn rats, the effects of the electrosurgical energy cannot be nearly as local or precise. The embryonic tooth-forming tissues of the third molar [lay] fractions of a millimeter below the oral mucosa and cannot be seen. As a result, it was not possible to predictably protect and isolate the vulnerable developing bone from the energy and heat of the electrosurgical energy. The result was a relatively large, unpredictable area of tissue damage during treatment and a wide range of bony developmental effects seen after the rats were euthanized." The TBA procedure 70 described herein can be distinguished from the Silvestri procedure in several ways including for example, that (1) the TBA procedure 70 described herein is a minimally invasive procedure consisting of introducing a surgical access path at each tooth bud surgical site as opposed to the boring, killing, and damaging procedure described by Silvestri, (2) the TBA procedure 70 described herein is performed in such a manner that it can be described as exact (e.g. using the patient's mouth as the mold for manufacturing or fabricating the surgical stent 110, taking exact measurements of the patient's mouth (including the position of the tooth bud 120), and using calculated parameter and time settings 105*b*) as opposed to the Silvestri procedure that can be described as inexact, and (3) the TBA procedure 70 described herein can predictably ablate tooth buds 120 as opposed to the Silvestri procedure that was essentially unpredictable and could never, under any circumstances, be considered for treating human patients.

Flow Charts

FIGS. 4, 11, 12, and 40 are flow charts illustrating processes, methods, and/or systems. It will be understood that at least some of the blocks of these flow charts, components of all or some of the blocks of these flow charts, and/or combinations of blocks in these flow charts, may be implemented by software (e.g. coding, computer program instructions, software programs, subprograms, or other series of computer-executable or processor-executable instructions), by hardware (e.g. processors, memory), by firmware, and/or a combination of these forms. As an example, in the case of software, computer program instructions (computer-readable program code) may be loaded onto a computer (or on a special purpose machine such as a volume scanner or scanning technology) to produce a machine, such that the instructions that execute on the computer create structures for implementing the functions specified in the flow chart block or blocks. These computer program instructions may also be stored in a memory that can direct a computer to function in a particular manner, such that the instructions stored in the memory produce an article of manufacture including instruction structures that implement the function specified in the flow chart block or blocks. The computer program instructions may also be loaded onto a computer (or on a special purpose machine such as a volume scanner or scanning technology) to cause a series of operational steps to be performed on or by the computer to produce a computer implemented process such that the instructions that execute on the computer provide steps for implementing the functions specified in the flow chart block or blocks. The term "loaded onto a computer" also includes being loaded into the memory of the computer or a memory associated with or accessible by the computer (or on a special purpose machine such as a volume scanner or scanning technology). The term "memory" is defined to include any type of computer (or other technology)-readable media including, but not limited to, attached storage media (e.g. hard disk drives, network disk drives, servers), internal storage media (e.g. RAM, ROM), removable storage media (e.g. CDs, DVDs, flash drives, memory cards, floppy disks), and/or other storage media known or yet to be discovered. The term "computer" is meant to include any type of processor, programmable logic device, or other type of programmable apparatus known or yet to be discovered. Accordingly, blocks of the flow charts support combinations of steps, structures, and/or modules for performing the specified functions. It will also be understood that each block of the flow charts, and combinations of blocks in the flow charts, may be divided and/or joined with other blocks of the flow charts without affecting the scope of the invention. This may result, for example, in computer-readable program code being stored in whole on a single memory, or various components of computer-readable program code being stored on more than one memory.

ADDITIONAL INFORMATION

It is to be understood that the inventions, examples, and embodiments described herein are not limited to particularly exemplified materials, methods, and/or structures. Further, all publications, patents, and patent applications cited herein, whether supra or infra, are hereby incorporated by reference in their entirety.

Please note that the terms and phrases may have additional definitions and/or examples throughout the specification. Where otherwise not specifically defined, words, phrases, and acronyms are given their ordinary meaning in the art. The following paragraphs provide some of the definitions for terms and phrases used herein.

The terms "fabricating" and/or "manufacturing" include any suitable means of making a component (e.g. stent 110). Although the terms are used together throughout most of the specification (e.g. "manufacturing or fabricating"), the absence of one term or another is irrelevant because they are used herein synonymously.

The terms "proper," "correct," "optimal," and "ideal," are relative and may become more accurate as technology is developed. For example, when used in terms of the pre-defined angle ($\phi$) and pre-defined depth (x) that are calculated and/or prescribed (e.g. the "proper angle and depth," the "correct angle and depth," the "optimal angle and depth," or the "ideal angle and depth"), these phrases are meant to include the best possible angle and depth that is calculated using the best available information and technology.

The terms "provide" and "providing" (and variations thereof) are meant to include standard means of provision including "transmit" and "transmitting," but can also be used for non-traditional provisions as long as the data is "received" (which can also mean obtained). The terms "transmit" and "transmitting" (and variations thereof) are meant to include standard means of transmission, but can also be used for non-traditional transmissions as long as the data is "sent." The terms "receive" and "receiving" (and variations thereof) are meant to include standard means of reception, but can also be used for non-traditional methods of obtaining as long as the data is "obtained."

It should be noted that the terms "may" and "might" are used to indicate alternatives and optional features and only should be construed as a limitation if specifically included in the claims. It should be noted that the various components, features, steps, phases, or embodiments thereof are all "preferred" whether or not it is specifically indicated. Claims not including a specific limitation should not be construed to include that limitation.

It should be noted that, unless otherwise specified, the term "or" is used in its nonexclusive form (e.g. "A or B" includes A, B, A and B, or any combination thereof, but it would not have to include all of these possibilities). It should be noted that, unless otherwise specified, "and/or" is used similarly (e.g. "A and/or B" includes A, B, A and B, or any combination thereof, but it would not have to include all of these possibilities). It should be noted that, unless otherwise specified, the term "includes" means "comprises" (e.g. a device that includes or comprises A and B contains A and B but optionally may contain C or additional components other than A and B). It should be noted that, unless otherwise specified, the singular forms "a," "an," and "the" refer to one or more than one, unless the context clearly dictates otherwise.

The terms and expressions that have been employed in the foregoing specification are used as terms of description and not of limitation, and are not intended to exclude equivalents of the features shown and described. This application is intended to cover any adaptations or variations of the present invention. It will be appreciated by those of ordinary skill in the art that any arrangement that is calculated to achieve the same purpose may be substituted for the specific embodiment shown. It is also to be understood that the following claims are intended to cover all of the generic and specific features of the invention herein described and all statements of the scope of the invention which, as a matter of language, might be said to fall therebetween.

What is claimed is:

1. A system configured for use in a tooth bud ablation procedure that results in tooth agenesis, said system comprising:
  (a) a movement sensored ablation probe tip having an insertion end and a connection end, said movement sensored ablation probe tip having a center of ablation;
  (b) a virtual stent comprising:
    (i) at least one volume scan to obtain a volume scan image;
    (ii) at least one virtual surgical guide angle, said at least one virtual surgical guide angle providing angle guidance to guide said movement sensored ablation probe tip at a pre-defined angle; and
    (iii) at least one virtual stop, said at least one virtual stop providing stop information to limit the depth of said movement sensored ablation probe tip to a pre-defined depth; and
  (c) said subsequently movement sensored ablation probe tip being guidable in relation to said at least one virtual surgical guide angle and said at least one virtual stop such that said center of ablation is within said tooth bud when said movement sensored ablation probe tip is guided at said pre-defined angle to said pre-defined depth, said pre-defined angle being based on information obtained from said volume scan image, and said pre-defined depth being based on information obtained from said volume scan image.

2. The system of claim 1, further comprising a display, said at least one virtual surgical guide angle being at least one virtual surgical guide angle marking displayed on said display, said at least one virtual stop being at least one virtual stop marking displayed on said display, said movement sensored ablation probe tip having a real-time representation displayed on said display.

3. The system of claim 1, said movement sensored ablation probe tip being manually guidable.

4. The system of claim 1, said movement sensored ablation probe tip being automatically guidable.

5. The system of claim 1, a real-time representation of said movement sensored ablation probe tip being monitorable in relation to said at least one volume scan.

6. A system configured for use in an ablation procedure that results in tissue agenesis, said system comprising:
   (a) a movement sensored ablation probe tip having an insertion end and a connection end, said movement sensored ablation probe tip having a center of ablation;
   (b) a virtual stent comprising:
      (i) at least one volume scan to obtain a volume scan image;
      (ii) at least one virtual surgical guide angle, said at least one virtual surgical guide angle providing angle guidance to guide said movement sensored ablation probe tip at a pre-defined angle; and
      (iii) at least one virtual stop, said at least one virtual stop providing stop information to limit the depth of said movement sensored ablation probe tip to a pre-defined depth; and
   (c) said subsequently movement sensored ablation probe tip being guidable in relation to said at least one virtual surgical guide angle and said at least one virtual stop such that said center of ablation is within said tissue when said movement sensored ablation probe tip is guided at said pre-defined angle to said pre-defined depth, said pre-defined angle being based on information obtained from said volume scan image, and said pre-defined depth being based on information obtained from said volume scan image.

7. The system of claim 6, further comprising a display, said at least one virtual surgical guide angle being at least one virtual surgical guide angle marking displayed on said display, said at least one virtual stop being at least one virtual stop marking displayed on said display, said movement sensored ablation probe tip having a real-time representation displayed on said display.

8. The system of claim 6, said movement sensored ablation probe tip being manually guidable.

9. The system of claim 6, said movement sensored ablation probe tip being automatically guidable.

10. The system of claim 6, a real-time representation of said movement sensored ablation probe tip being monitorable in relation to said at least one volume scan.

11. The system of claim 6, wherein said tissue is a lesion or a tumor.

* * * * *

UNITED STATES PATENT AND TRADEMARK OFFICE
CERTIFICATE OF CORRECTION

PATENT NO. : 11,173,012 B2
APPLICATION NO. : 17/006697
DATED : November 16, 2021
INVENTOR(S) : Leigh E. Colby It is certified that error appears in the above-identified patent and that said Letters Patent is hereby corrected as shown below:

In the Claims

<u>Column 46:</u>
Line 61, delete "said subsequently" and replace with -- subsequently said --.

<u>Column 48:</u>
Line 5, delete "said subsequently" and replace with -- subsequently said --.

Signed and Sealed this
Twenty-fifth Day of February, 2025

Coke Morgan Stewart
*Acting Director of the United States Patent and Trademark Office*